US011390669B2

(12) United States Patent
Timony et al.

(10) Patent No.: US 11,390,669 B2
(45) Date of Patent: Jul. 19, 2022

(54) METHODS OF TREATMENT OF DISEASES IN WHICH IL-13 ACTIVITY IS DETRIMENTAL USING ANTI-IL-13 ANTIBODIES

(71) Applicant: AbbVie Inc., North Chicago, IL (US)

(72) Inventors: Gregg Timony, Carlsbad, CA (US); Sheila Gujrathi, Rancho Santa Fe, CA (US); Robert Peach, San Diego, CA (US); Allan Olson, San Diego, CA (US)

(73) Assignee: Abbvie, Inc., North Chicago, IL (US)

( * ) Notice: Subject to any disclaimer, the term of this patent is extended or adjusted under 35 U.S.C. 154(b) by 179 days.

(21) Appl. No.: 16/092,943

(22) PCT Filed: Apr. 27, 2017

(86) PCT No.: PCT/US2017/029768
§ 371 (c)(1),
(2) Date: Oct. 11, 2018

(87) PCT Pub. No.: WO2017/189805
PCT Pub. Date: Nov. 2, 2017

(65) Prior Publication Data
US 2021/0380674 A1 Dec. 9, 2021

Related U.S. Application Data

(60) Provisional application No. 62/328,539, filed on Apr. 27, 2016.

(51) Int. Cl.
| | |
|---|---|
| *C07K 16/24* | (2006.01) |
| *A61P 37/06* | (2006.01) |
| *A61P 1/00* | (2006.01) |
| *A61K 31/436* | (2006.01) |
| *A61K 31/519* | (2006.01) |
| *A61K 31/58* | (2006.01) |
| *A61K 38/13* | (2006.01) |
| *A61K 39/395* | (2006.01) |
| *A61K 45/06* | (2006.01) |

(52) U.S. Cl.
CPC .......... *C07K 16/244* (2013.01); *A61K 31/436* (2013.01); *A61K 31/519* (2013.01); *A61K 31/58* (2013.01); *A61K 38/13* (2013.01); *A61K 39/3955* (2013.01); *A61K 45/06* (2013.01); *A61P 1/00* (2018.01); *A61P 37/06* (2018.01); *C07K 2317/56* (2013.01)

(58) Field of Classification Search
None
See application file for complete search history.

(56) References Cited

U.S. PATENT DOCUMENTS

| | | |
|---|---|---|
| 2008/0171014 A1 | 7/2008 | Wu et al. |
| 2013/0096096 A1 | 4/2013 | Dohil et al. |
| 2014/0341913 A1 | 11/2014 | Tripp |
| 2015/0017176 A1 | 1/2015 | Kostic et al. |

FOREIGN PATENT DOCUMENTS

| | | | | |
|---|---|---|---|---|
| JP | 2010-502224 | 1/2010 | | |
| JP | 2016-041689 | 3/2016 | | |
| WO | 2008/127271 | 10/2008 | | |
| WO | WO 2008/127271 | * 10/2008 | ............. | C07K 14/00 |
| WO | 2011/050071 | 4/2011 | | |
| WO | 2012/083132 | 6/2012 | | |
| WO | 2013009521 | 1/2013 | | |
| WO | 2015006571 | 1/2015 | | |
| WO | WO 2015/061441 | * 4/2015 | ............... | C12Q 1/68 |

OTHER PUBLICATIONS

Piche-Nicholas et al., MAbs. 2018; 10: 81-94. doi: 10.1080/19420862.2017.1389355 (Year: 2018).*
Schoepfer et al., Gastroenterology 2014;147:1255-126 (Year: 2014).*
Ikuo Hirano, Dig Dis 2014;32:78-83 (Year: 2014).*
Arnim, Dig Dis 2014; 32:126-129 (Year: 2014).*
Google translation of JP2016041689, downloaded on Nov. 19, 2021 from https://patents.google.com/patent/JP2016041689A/en?oq=jp2016041689; 45 pages total (Year: 2021).*
Leslie Adato, posted on May 2015 at the website https://med.stanford.edu/allergyandasthma/news/news-from-our-center/eosinophilic-esophagitis.html; 6 pages total (Year: 2015).*
"Dose Ranging Study of RPC4046 in Eosinophilic Esophagitis", ClinicalTrials.gov, Mar. 28, 2014, pp. 1-3.
Rothenberg, Marc E., et al., "Intravenous Anti-IL-13 mAb QAX576 for the Treatment of Eosinophilic Esophagitis", Journal of Allergy and Clinical Immunology, Feb. 1, 2015, vol. 135, No. 2, pp. 500-507.
Goyal, Aakash, et al., "Recent Discoveries and Emerging Therapeutics in Eosinophilic Esophagitis", World Journal of Gastrointestinal Pharmacology and Therapeutics, Jan. 1, 2016, vol. 7, No. 1, pp. 21-32.
Hirano, I., et al., "A Randomized, Double-Blind, Placebo-Controlled Trial of Anti-Interleukin-13 Monoclonal Antibody RPC4046 in Patients with Eosinophilic Esophagitis", Annals of Allergy, Asthma & Immunology, 2018, vol. 121, No. 5, 1 Page.
Supplemental European Search Report, based on co-pending European Application No. 17790401.8, dated Nov. 11, 2019—9 Pages.
International Preliminary Report on Patentability dated Oct. 30, 2018 based on co-pending PCT International Application No. PCT/US2017/029768, 9 Pages.
Office Action dated May 29, 2020, based on co-pending Chinese Application No. 201780040303.8; 21 pages which includes English Translation.

(Continued)

Primary Examiner — Christina M Borgeest
(74) Attorney, Agent, or Firm — McCarter & English, LLP

(57) ABSTRACT

The present invention is directed to methods for treating diseases in which IL-13 activity is detrimental, including eosinophilic esophagitis (EoE) and asthma, by administering to a subject in need of such treatment, a composition containing an inter leukin-13 (IL-13) antibody, or an antigen binding fragment, thereof.

27 Claims, 18 Drawing Sheets

Specification includes a Sequence Listing.

(56) References Cited

OTHER PUBLICATIONS

Examination Report based on co-pending Australian Patent Application No. 2017258097, dated Jun. 13, 2019—pp. 1-4.
Willis-Karp, Marsha, et al., "Interleukin-13: Central Mediator of Allergic Asthma", Science, Dec. 18, 1998, vol. 282, pp. 2258-2261.
Mueller, Thomas D., et al., "Structure, Binding, and Antagonists in the IL-4/IL-13 Receptor System", Biochimica et Biophysica Acta 1592, 2002, pp. 237-250.
Junttila, Llkka S., et al., "Tuning the Cytokine Responses: An Update on Interleukin (IL)-4 and IL-13 Receptor Complexes", Frontiers in Immunology, Jun. 7, 2018, vol. 9, Article 888, pp. 1-6.
McCormick, Sarah M., et al., "Commentary: IL-4 and IL-13 Receptors and Signaling", Cytokine 75, 2015, pp. 38-50.
Canadian Office Action dated Apr. 21, 2021 relating to co-pending Canadian Application No. 3,021,334, pp. 1-4.
Leech, Michelle, et al., "Regulation of p53 by Macrophage Migration Inhibitory Factor in Inflammatory Arthritis", Arthritis & Rheumatism, Jul. 2003, vol. 48, No. 7, pp. 1881-1889.
Dellon, E.S., et al., "Development and Field Testing of a Novel Patient-Reported Outcome Measure of Dysphagia in Patients with Eosinophilic Esophagitis", Alimentary Pharmacology and Therapeutics, 2013, vol. 38, No. 6, pp. 634-642.
Hirano, Ikuo, "ACG Midwest Postgraduate Course, Eosinophilic Esophagitis", Publication online 2013, Retrieved from the Internet Aug. 30, 2017, pp. 1-28.
Schoepfer, Alain M., et al., "How Do Gastroenterologists Assess Overall Activity of Eosinophilic Esophagitis in Adult Patients?", The American Journal of Gastroenterology, Mar. 3, 2015, vol. 110, No. 3, pp. 402-414.
Collins, Margaret H., et al., "Eosinophilic Esophagitis (EoE) Histologic Changes More Strongly Associate with Treatment Status Than Peak Eosinophil Count (PEC)", Journal of Allergy and Clinical Immunology, 2015, vol. 135, No. 2, col. 1, p. AB39.
International Search Report dated Sep. 15, 2017, based on International Application No. PCT/US2017/029768—6 Pages.
Written Opinion dated Sep. 15, 2017, based on International Application No. PCT/US2017/029768—8 Pages.
Tripp, Catherine S., et al., "RPC4046, A Novel Anti-interleukin-13 Antibody, Blocks IL-13 Binding to IL-13 $\alpha 1$ and $\alpha 2$ Receptors: A Randomized, Double-Blind, Placebo-Controlled, Dose-Escalation First-in-Human Study", Advances in Therapy, Apr. 28, 2017, pp. 1-18.
Gann, Peter H., et al., "An Anti-IL-13 Antibody Reverses Epithelial-Mesenchymal Transition Biomarkers in Eosinophilic Esophagitis: Phase 2 Trial Results", The Journal of Allergy and Clinical Immunology, Aug. 2020, vol. 146, No. 2, pp. 367-380.
Dellon, Evan S., et al., "Long-Term Efficacy and Tolerability of RPC4046 in an Open-Label Extension Trial of Patients with Eosinophilic Esophagitis", Clinical Gastroenterology and Hepatology, 2021, vol. 19, No. 3, pp. 473-483.
Hirano, Ikuo, et al., "RPC4046, a Monoclonal Antibody Against IL 13, Reduces Histologic and Endoscopic Activity in Patients with Eosinophilic Esophagitis", Gastroenterology, Feb. 2019, vol. 156, No. 3, pp. 592-603.
Beveridge, Claire, et al., "Novel Therapuetic Approaches to Eosinophilic Esophagitis", Gastroenterology & Hepatology, Jun. 2020, vol. 16, Issue 6, pp. 294-301.
De Rooji, Willemijn E., et al., "Pharmacotherapies for the Treatment of Eosinophilic Esophagitis: State of the Art Review", Drugs, Jul. 27, 2019, pp. 1-16.

\* cited by examiner

SEQUENCE LISTING

<160> NUMBER OF SEQ ID NOS: 3

<210> SEQ ID NO 1
<211> LENGTH: 132
<212> TYPE: PRT
<213> ORGANISM: Homo sapiens

<400> SEQUENCE: 1

```
Met Ala Leu Leu Leu Thr Thr Val Ile Ala Leu Thr Cys Leu Gly Gly
1               5                   10                  15

Phe Ala Ser Pro Gly Pro Val Pro Pro Ser Thr Ala Leu Arg Glu Leu
            20                  25                  30

Ile Glu Glu Leu Val Asn Ile Thr Gln Asn Gln Lys Ala Pro Leu Cys
        35                  40                  45

Asn Gly Ser Met Val Trp Ser Ile Asn Leu Thr Ala Gly Met Tyr Cys
    50                  55                  60

Ala Ala Leu Glu Ser Leu Ile Asn Val Ser Gly Cys Ser Ala Ile Glu
65                  70                  75                  80

Lys Thr Gln Arg Met Leu Ser Gly Phe Cys Pro His Lys Val Ser Ala
                85                  90                  95

Gly Gln Phe Ser Ser Leu His Val Arg Asp Thr Lys Ile Glu Val Ala
            100                 105                 110

Gln Phe Val Lys Asp Leu Leu Leu His Leu Lys Lys Leu Phe Arg Glu
        115                 120                 125

Gly Arg Phe Asn
    130
```

<210> SEQ ID NO 2
<211> LENGTH: 123
<212> TYPE: PRT
<213> ORGANISM: Artificial Sequence
<220> FEATURE:
<223> OTHER INFORMATION: Synthetic

<400> SEQUENCE: 2

```
Glu Val Thr Leu Arg Glu Ser Gly Pro Gly Leu Val Lys Pro Thr Gln
1               5                   10                  15

Thr Leu Thr Leu Thr Cys Thr Leu Tyr Gly Phe Ser Leu Ser Thr Ser
            20                  25                  30

Asp Met Gly Val Asp Trp Ile Arg Gln Pro Pro Gly Lys Gly Leu Glu
        35                  40                  45

Trp Leu Ala His Ile Trp Trp Asp Asp Val Lys Arg Tyr Asn Pro Ala
    50                  55                  60

Leu Lys Ser Arg Leu Thr Ile Ser Lys Asp Thr Ser Lys Asn Gln Val
65                  70                  75                  80

Val Leu Lys Leu Thr Ser Val Asp Pro Val Asp Thr Ala Thr Tyr Tyr
                85                  90                  95
```

```
Cys Ala Arg Thr Val Ser Ser Gly Tyr Ile Tyr Tyr Ala Met Asp Tyr
            100                 105                 110

Trp Gly Gln Gly Thr Leu Val Thr Val Ser Ser
        115                 120

<210> SEQ ID NO 3
<211> LENGTH: 107
<212> TYPE: PRT
<213> ORGANISM: Artificial Sequence
<220> FEATURE:
<223> OTHER INFORMATION: Synthetic

<400> SEQUENCE: 3

Asp Ile Gln Met Thr Gln Ser Pro Ser Ser Leu Ser Ala Ser Val Gly
1               5                   10                  15

Asp Arg Val Thr Ile Ser Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Phe Tyr Thr Ser Lys Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Ile Ala Thr Tyr Tyr Cys Gln Gln Gly Asn Thr Leu Pro Leu
                85                  90                  95

Thr Phe Gly Gly Gly Thr Lys Val Glu Ile Lys
            100                 105
```

METHODS OF TREATMENT OF DISEASES IN WHICH IL-13 ACTIVITY IS DETRIMENTAL USING ANTI-IL-13 ANTIBODIES

CROSS-REFERENCE TO RELATED APPLICATIONS

This application is a national stage application filed under 35 U.S.C. § 371 of PCT/US2017/029768, filed Apr. 27, 2017, which claims the benefit of U.S. Provisional Application No. 62/328,539, filed Apr. 27, 2016, each of which is incorporated herein, in its entirety, by reference.

SUBMISSION OF SEQUENCE LISTING

The Sequence Listing associated with this application is filed in electronic format via EFS-Web and hereby incorporated by reference into the specification in its entirety. The name of the text file containing the Sequence Listing is sequencelisting.txt. The size of the text file is 4 KB, and the text file was created on Oct. 10, 2018.

BACKGROUND

Eosinophilic disorders constitute a diverse spectrum of disorders that are often characterized by aberration in the number and/or activity of eosinophils (termed hypereosinophilia). This aberration is often observed in conjunction with, and sometimes constitutes the pathological basis for, many allergic conditions involving the gastrointestinal tract. Examples of such eosinophilic gastrointestinal disorders (EGID) that have been recently characterized in medical literature include eosinophilic esophagitis (EoE or EE), eosinophilic gastritis (EoG or EG), eosinophilic duodenitis (ED), eosinophilic jejunitis (EJ), eosinophilic ileitis (EI), and eosinophilic colitis (EC). See, e.g., Rothenberg et al., *Allergy Clin. Immunol.*, 113:11-28 (2004); Furata et al., *Gastroenterology* 133:1342-63 (2007); and Talley et al. *Gut* 31:54-8 (1990).

The EGID that has been studied the most is EoE, partly because the diagnosis is made with increasing frequency (Furata et al., *Gastroenterology* 133:1342-63 (2007)). EoE is characterized most frequently by signs and symptoms related to esophageal dysfunction (Liacouras et al., *J. Allergy Clin. Immunol.* 128:3-20 (2011)). In adults these include dysphagia, chest pain, food impaction, emesis and upper abdominal pain (Croese et al., *Gastrointest. Endosc.*, 58:516-522 (2003)). Clinical manifestations in children vary by age. Infants often present with feeding difficulties and failure to thrive, whereas school-aged children are likely to exhibit increased emesis and chest pain (Liacouras et al., 2011; supra).

EoE is considered to have an allergic etiology with 70% of patients having current or past allergic disease or positive skin prick tests to food or other allergens (Blanchard et al., *Gastrointest. Endosc. Clin. N. Am.*, 18:133-43 (2008)). The symptoms of EoE are generally resistant to proton pump inhibitor (PPI) therapy, although a small subset of patients does demonstrate a clinicopathological response to PPIs (Molina-Infante et al., *Clin. Gastroenterol. Hepatol.*, 9:110-117 (2011)). Topical corticosteroids, used "off-label" in EoE, can be effective at reducing the eosinophilic load of the esophagus. For instance, clinical studies have shown that both fluticasone and budesonide may be effective as induction treatments for reducing eosinophilic load and symptoms in both children and adults with EoE (Schaefer et al., *Clin. Gastroenterol. Hepatol.*, 6:165-173 (2008); Konikoff et al., *Gastroenterology*, 131:1381-1391 (2006); Dohil et al., *Gastroenterology*, 139:418-429 (2010); Straumann et al., *Gastroenterology*, 139:1526-1537 (2010)). However, owing to the chronic nature of EoE and the many side effects of steroid agents, a vast majority of patients, especially children, are forced to remain on proton pump inhibitors despite the medium-to-low level of effectiveness associated with such agents.

Interleukin-13 (IL-13) has been implicated in the aforementioned gastrointestinal disorders. Moreover, inflammatory cytokines, such as IL-13, are also relevant for other allergy/inflammatory diseases. For example, IL-13 is thought to be pivotal in the pathogenesis of human asthma, in that elevated levels of IL-13 are present in the lungs of asthma patients, and these levels correlate with disease severity. Likewise, increased IL-13 is present in both sputum and in lung biopsies of patients with moderate to severe asthma who are treated with inhaled corticosteroids (ICS) or systemic corticosteroids but continue to be symptomatic. Moreover, human IL-13 genetic polymorphisms are associated with asthma and atopy (allergic hypersensitivity).

Due to the role of human IL-13 in a variety of human disorders, therapeutic strategies have been designed to inhibit or counteract IL-13 activity. However, there exists a need in the art for improved IL-13 inhibitors that are useful and effective in treating and ameliorating diseases such as EGID and asthma. Moreover, discovering the optimal dosage and route of administration of therapeutic agents is a complex process which involves inventive input, analysis of large amounts of data and clinical trials with hundreds of patients; a process which is not routine. There is, therefore, an unmet need for identifying therapeutic agents, and optimal dosage regiments, that allow for the effective treatment of eosinophilic disorders, such as EoE, and inflammatory diseases, such as asthma.

SUMMARY

The present disclosure provides a solution to the problem of effectively treating diseases in which IL-13 activity is detrimental, such as asthma and eosinophilic disorders, e.g., eosinophilic esophagitis (EoE or EE), using an anti-IL-13 antibody, or antigen-binding portion thereof. Specifically, the present disclosure provides dosing regimens with improved therapeutic efficacy. For example, the claimed methods of treatment using anti-IL-13 antibodies were shown to surprisingly and significantly reduce esophageal eosinophil count in esophageal biopsies of patients with EoE.

In one aspect, the instant invention provides for a method of treating eosinophilic esophagitis (EoE) in a subject, comprising subcutaneously administering about 180 mg to about 360 mg of an IL-13 antibody, or antigen binding fragment thereof, to the subject weekly, thereby treating EoE in the subject.

In one embodiment, the IL-13 antibody, or antigen-binding fragment thereof binds to IL-13 and prevents interaction between IL-13 and an IL-13 receptor. In one embodiment, the IL-13 antibody, or antigen-binding portion thereof, is a monoclonal antibody, or antigen-binding portion thereof. In one embodiment, the IL-13 antibody, or antigen-binding portion thereof, is a humanized antibody, or antigen-binding portion thereof. In one embodiment, the IL-13 antibody, or antigen-binding portion thereof, is a human antibody, or antigen-binding portion thereof.

In one embodiment, the IL-13 antibody, or antigen-binding fragment thereof, is the antibody 13C5.5, or an antigen binding fragment thereof. In one embodiment, the 13C5.5 antibody, or antigen-binding fragment thereof, comprises a heavy chain variable region comprising SEQ ID NO: 2 and a light chain variable region comprising SEQ ID NO: 3.

In another embodiment, the anti-IL-13 antibody is 6A1, 3G4, tralokinumab, lebrikizumab, QAZ-576, IMA-638 or IMA-026, or an antigen-binding portion thereof.

In one embodiment, the method comprises subcutaneously administering about 180 mg of the IL-13 antibody, or antigen binding fragment thereof, to the subject weekly. In another embodiment, the method comprises subcutaneously administering about 360 mg of the IL-13 antibody, or antigen binding fragment thereof, to the subject weekly.

In one embodiment, the method further comprises a step of selecting a subject who exhibits at least one symptom associated with EoE. In one embodiment, the symptom associated with EoE is selected from the group consisting of eosinophilic infiltration of the esophagus, thickening of the esophageal wall, food refusal, vomiting, abdominal pain, heartburn, regurgitation, dysphagia, and food impaction.

In one embodiment, the method further comprises selecting a subject who also has a disease or disorder selected from the group consisting of atopic dermatitis, asthma, allergic rhinitis, allergic conjunctivitis, and a combination thereof.

In one embodiment, the selection step comprises selecting a subject based on an elevated level of a biomarker associated with eosinophilic esophagitis (EoE). In one embodiment, the biomarker selected from the group consisting of esophagus eosinophils, eotaxin-3, periostin, serum IgE, IL-13, IL-5, serum thymus and activation regulated chemokine (TARC; CCL17), thymic stromal lymphopoietin (TSLP), serum ECP, and eosinophil-derived neurotoxin (EDN) or a combination thereof.

In one embodiment, the selection step comprises selecting a subject based on the mean esophageal eosinophil count in a biopsy sample obtained from the subject during an esophageal endoscopy. In one embodiment, the selection step comprises selecting a subject based on peak eosinophil count of ≥15 per high powered field (HPF) in the esophagus.

In one embodiment, the subject exhibits at least 50% decrease in the number of eosinophils per HPF from the peak level after at least 16 weeks of administration of the IL-13 antibody, or antigen binding fragment thereof.

In one embodiment, the subject is a steroid naïve subject who has not previously undergone steroid therapy. In another embodiment, the subject is a human subject who has previously undergone steroid therapy. In one embodiment, the subject is a human subject who has previously undergone steroid therapy and is non-steroid refractory. In another embodiment, the subject is a human subject who has previously undergone steroid therapy and is steroid refractory.

In one embodiment, the antibody, or antigen-binding portion thereof, is administered to the subject for at least about 16 weeks. In another embodiment, the antibody, or antigen-binding portion thereof, is administered to the subject for the duration of EoE disease.

In one embodiment, the method comprises determining a mean esophageal eosinophil count measured in the 5 most inflamed high powered field (HPF) in the esophagus before administration of the antibody, or antigen-binding portion thereof, to the subject. In another embodiment, the method comprises determining the mean esophageal eosinophil count measured in the 5 most inflamed high powered field (HPF) in the esophagus after administration of the antibody, or antigen-binding portion thereof, to the subject. In one embodiment, a decrease in the mean esophageal eosinophil count after administration of the antibody, or antigen-binding portion thereof, to the subject as compared to the mean esophageal eosinophil count before administration indicates that the antibody, or antigen-binding portion thereof, is effective in treating the subject.

In one embodiment, the method comprises determining dysphagia clinical symptoms before administration of the antibody, or antigen-binding portion thereof, to the subject. In one embodiment, the method comprises determining the dysphagia clinical symptoms after administration of the antibody, or antigen-binding portion thereof, to the subject, wherein a decrease in the dysphagia clinical symptoms after administration of the antibody, or antigen-binding portion thereof, to the subject as compared to the dysphagia clinical symptoms before administration indicates that the antibody, or antigen-binding portion thereof, is effective in treating the subject.

In one embodiment, the method comprises determining eosinophilic esophagitis activity index (EEsAI) and recorded as a daily symptom diary (DSD) before administration of the antibody, or antigen-binding portion thereof, to the subject. In one embodiment, the method comprises determining the eosinophilic esophagitis activity index (EEsAI) and recorded as a daily symptom diary (DSD) after administration of the antibody, or antigen-binding portion thereof, to the subject, wherein a decrease in the EEsAI after administration of the antibody, or antigen-binding portion thereof, to the subject as compared to the EEsAI before administration indicates that the antibody, or antigen-binding portion thereof, is effective in treating the subject.

In one embodiment, the method comprises determining dysphagia symptom questionnaire (DSQ) score before administration of the antibody, or antigen-binding portion thereof, to the subject. In one embodiment, the method comprises determining the DSQ score after administration of the antibody, or antigen-binding portion thereof, to the subject; wherein a decrease in the DSQ score after administration of the antibody, or antigen-binding portion thereof, to the subject as compared to the DSQ score before administration indicates that the antibody, or antigen-binding portion thereof, is effective in treating the subject.

In one embodiment, the method comprises determining endoscopic reference score (EREF) before administration of the antibody, or antigen-binding portion thereof, to the subject. In one embodiment, the method comprises determining the EREF score after administration of the antibody, or antigen-binding portion thereof, to the subject; wherein a decrease in the EREF score after administration of the antibody, or antigen-binding portion thereof, to the subject as compared to the EREF score before administration indicates that the antibody, or antigen-binding portion thereof, is effective in treating the subject.

In one embodiment, the EREF is determined based on the presence of inflammatory markers in the esophagus, the presence of remodeling markers in the esophagus, or a combination thereof. In one embodiment, the EREF is determined based on the presence or absence of plurality of features selected from the group consisting of edema, fixed rings, exudates, furrows and stricture, or a combination thereof.

In one embodiment, the method comprises determining a subject's global assessment of disease severity before administration of the antibody, or antigen-binding portion thereof, to the subject. In one embodiment, the method comprises determining the subject's global assessment of disease severity after administration of the antibody, or antigen-binding portion thereof, to the subject; wherein a decrease in the a subject's global assessment of disease severity after administration of the antibody, or antigen-binding portion thereof, to the subject as compared to the a subject's global assessment of disease severity before administration indicates that the antibody, or antigen-binding portion thereof, is effective in treating the subject.

In one embodiment, the method comprises determining a clinician's global assessment of disease severity before administration of the antibody, or antigen-binding portion thereof, to the subject. In one embodiment, the method comprises determining the clinician's global assessment of disease severity after administration of the antibody, or antigen-binding portion thereof, to the subject; wherein a decrease in the a clinician's global assessment of disease severity after administration of the antibody, or antigen-binding portion thereof, to the subject as compared to the clinician's global assessment of disease severity before administration indicates that the antibody, or antigen-binding portion thereof, is effective in treating the subject.

In one embodiment, the method comprises determining a histology grade and a mean stage-adjusted score (HGMSAS) before administration of the antibody, or antigen-binding portion thereof, to the subject. In one embodiment, the method comprises determining the HGMSAS after administration of the antibody, or antigen-binding portion thereof, to the subject; wherein a decrease in the HGMSAS after administration of the antibody, or antigen-binding portion thereof, to the HGMSAS before administration indicates that the antibody, or antigen-binding portion thereof, is effective in treating the subject.

In one embodiment, the method further comprises administration of an additional agent. In one embodiment, the additional agent is a steroid. In one embodiment, the additional agent is the steroid compound budesonide. In one embodiment, the additional agent is selected from the group consisting of: a therapeutic agent, an imaging agent, a cytotoxic agent, an angiogenesis inhibitor, a kinase inhibitor, a co-stimulation molecule blocker, an adhesion molecule blocker, an anti-cytokine antibody or functional fragment thereof; methotrexate, a cyclosporin, a rapamycin, an FK506, a detectable label or reporter, a TNF antagonist, an anti-rheumatic, a muscle relaxant, a narcotic, a non-steroid anti-inflammatory drug (NSAID), an analgesic, an anesthetic, a sedative, a local anesthetic, a neuromuscular blocker, an antimicrobial, an antipsoriatic, a corticosteroid, an anabolic steroid, an erythropoietin, an immunization, an immunoglobulin, an immunosuppressive, a growth hormone, a hormone replacement drug, a radiopharmaceutical, an antidepressant, an antipsychotic, a stimulant, an asthma medication, a beta agonist, an inhaled steroid, an oral steroid, an epinephrine or analog, a cytokine, and a cytokine antagonist.

In one aspect, the present disclosure provides compositions and methods for treating asthma. In one aspect, the instant disclosure provides for a method of treating asthma in a subject, comprising subcutaneously administering about 180 mg to about 360 mg of an IL-13 antibody, or antigen binding fragment thereof, to the subject weekly, thereby treating asthma in the subject.

In one embodiment, the IL-13 antibody, or antigen-binding fragment thereof binds to IL-13 and prevents interaction between IL-13 and an IL-13 receptor. In one embodiment, the antibody, or antigen-binding portion thereof, is a monoclonal antibody. In one embodiment, the antibody, or antigen-binding portion thereof, is a humanized antibody. In one embodiment, the antibody, or antigen-binding portion thereof, is a human antibody.

In one embodiment, the antibody, or antigen-binding portion thereof, is a 13C5.5 antibody. In one embodiment, the 13C5.5 antibody, or antigen-binding fragment thereof, comprises a heavy chain variable region comprising SEQ ID NO: 2 and a light chain variable region comprising SEQ ID NO: 3.

In another embodiment, the anti-IL-13 antibody is 6A1, 3G4, tralokinumab, lebrikizumab, QAZ-576, IMA-638 or IMA-026, or an antigen-binding portion thereof.

In one embodiment, the method comprises subcutaneously administering about 180 mg of the IL-13 antibody, or antigen binding fragment thereof, to the subject weekly. In one embodiment, the method comprises subcutaneously administering about 360 mg of the IL-13 antibody, or antigen binding fragment thereof, to the subject weekly.

In one embodiment, the asthma is mild to moderate asthma.

In another aspect, the method further comprises selecting a subject who exhibits at least one symptom associated with asthma. In a related embodiment, the at least one symptom associated with asthma selected from the group consisting of secretion or build-up of sticky mucus or phlegm, coughing, wheezing, shortness of breath, chest tightness, chest pain and chest pressure.

In one embodiment, the subject is a human subject. In another embodiment, the subject is a steroid naïve subject who has not previously undergone steroid therapy. In one embodiment, the subject has previously undergone steroid therapy. In one embodiment, the subject is a subject who has previously undergone steroid therapy, and the subject is non-steroid refractory. In another embodiment, the subject is a subject who has previously undergone steroid therapy, and the subject is steroid refractory.

In one embodiment, the antibody, or antigen binding fragment thereof, is administered to the subject weekly for at least about 16 weeks. In another embodiment, the antibody, or antigen binding portion thereof, is administered to the subject weekly for the duration of EoE disease.

In one embodiment, the method further comprises determining a biomarker associated with asthma before and after administration of the IL-13 antibody, or antigen binding fragment thereof, to the subject, wherein a change in the biomarker level indicates the efficacy of the IL-13 antibody, or antigen binding fragment thereof, in treating the subject.

In one embodiment, the method further comprises administration of an additional agen. In one embodiment, the additional agent is a steroid. In another embodiment, the additional agent is budesonide. In yet another embodiment, the additional agent is selected from the group consisting of: a therapeutic agent, an imaging agent, a cytotoxic agent, an angiogenesis inhibitor, a kinase inhibitor, a co-stimulation molecule blocker, an adhesion molecule blocker, an anti-cytokine antibody or functional fragment thereof; methotrexate, a cyclosporin, a rapamycin, an FK506, a detectable label or reporter, a TNF antagonist, an anti-rheumatic, a muscle relaxant, a narcotic, a non-steroid anti-inflammatory drug (NSAID), an analgesic, an anesthetic, a sedative, a local anesthetic, a neuromuscular blocker, an antimicrobial, an antipsoriatic, a corticosteroid, an anabolic steroid, an erythropoietin, an immunization, an immunoglobulin, an immunosuppressive, a growth hormone, a hormone replacement drug, a radiopharmaceutical, an antidepressant, an antipsychotic, a stimulant, an asthma medication, a beta agonist, an inhaled steroid, an oral steroid, an epinephrine or analog, a cytokine, and a cytokine antagonist.

Other features and advantages of the disclosure will be apparent from the following description of the preferred embodiments thereof, and from the claims. References cited are hereby incorporated by reference.

BRIEF DESCRIPTION OF THE DRAWINGS

Various features and advantages of the embodiments herein described can be fully appreciated as the same becomes better understood when considered in light of the accompanying drawings.

BRIEF DESCRIPTION OF THE TABLES

Figure 1:
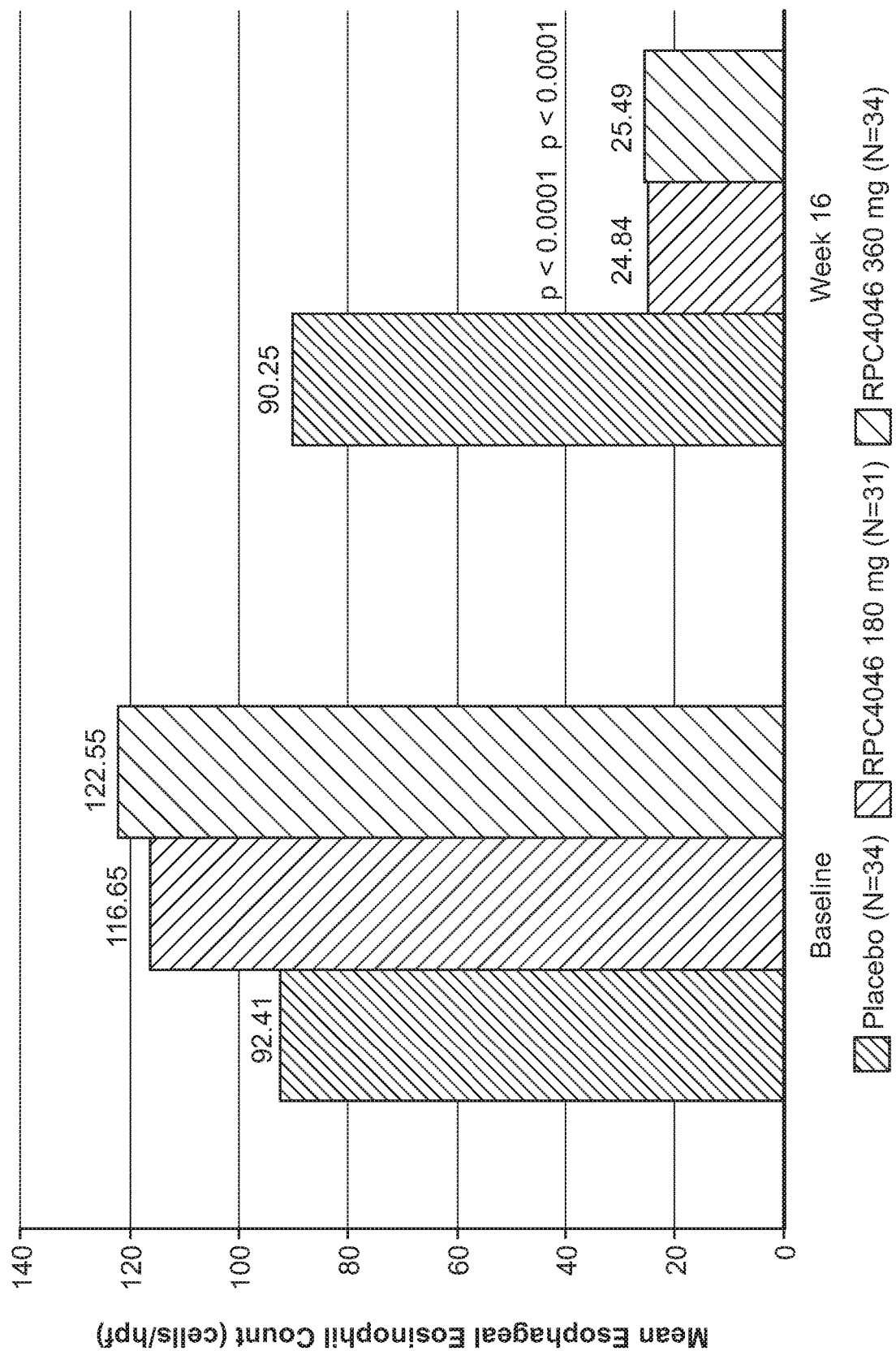
FIG. 1 shows mean esophageal eosinophil counts (cells/hpf) at baseline and at week 16 in the placebo group, low dose (180 mg) treatment group and high dose (360 mg) treatment group. Statistical significance was calculated by measuring p-values from ANCOVA model adjusted for steroid refractory status and baseline mean esophageal eosinophil count.

Table 1 provides a summary of the demographics of the subjects enrolled in the study.

Table 2 provides a sample daily symptom diary (DSD) questionnaire and a method employed to compute a DSD score.

Table 3 shows mean change from baseline to Week 16 in the dysphagia clinical symptom frequency and severity as assessed by the DSD completed over 2 weeks.

Table 4 provides a summary of results from the study evaluating dysphagia symptom composite diary score at week 16 in subjects belonging to the ITT group who were treated with the low dose (180 mg) or high dose (360 mg) of RPC4046.

Table 5 provides a summary of results from the study evaluating dysphagia symptom composite diary score at week 16 in subjects belonging to the ITT group (sub-grouped according to steroid refractory status) who were treated with the low dose (180 mg) or high dose (360 mg) of RPC4046.

Table 6 provides a summary of the results evaluating the efficacy of placebo, oral budesonide, RPC4046 and QAX576 across three different studies.

Table 7 provides a summary of results from the study evaluating mean change in peak esophageal eosinophil count (cells/hpf) at week 16 in placebo versus subjects who were treated with the low dose (180 mg) or high dose (360 mg) of RPC4046.

Table 8 provides a summary of results from the study evaluating mean EEsAI PRO scores at baseline and at week 16 in placebo versus subjects who were treated with the low dose (180 mg) or high dose (360 mg) of RPC4046.

Table 9 provides a summary of results from the study evaluating mean EEsAI PRO scores at baseline and at week 16 in steroid refractory versus non-steroid-refractory subjects who were given placebo or treated with the low dose (180 mg) or high dose (360 mg) of RPC4046.

Table 10 provides a summary of results from the study evaluating subject's global assessment of disease severity at baseline and at week 16 in subjects who were given placebo or treated with the low dose (180 mg) or high dose (360 mg) of RPC4046.

Table 11 provides a summary of results from the study evaluating clinician's global assessment of disease severity at baseline and at week 16 in subjects who were given placebo or treated with the low dose (180 mg) or high dose (360 mg) of RPC4046.

Table 12 provides a summary of treatment-associated adverse events in subjects treated with RPC4046.

DETAILED DESCRIPTION

The present disclosure surprisingly provides methods for treating or ameliorating at least one symptom of an eosinophilic disorder, e.g., EoE, in a subject, using an anti-IL-13 antibody, or antigen-binding portion thereof. Surprisingly, after performing phase II clinical trials in humans with hundreds of patients, the instant invention surprisingly demonstrates that subcutaneous doses of anti-IL-13 antibody administered weekly at dosages of 180 mg to 360 mg were found to be effective in treating EoE, for example, by decreasing dysphagic clinical symptoms. Specific embodiments of the invention are described in more detail in the subsections, below.

I. IL-13 Antibodies, and Antigen-Binding Portions Thereof

The terms "IL-13" and "IL-13 wild type" (abbreviated herein as IL-13, IL-13 wt), as used herein, include a cytokine that is secreted primarily by T helper 2 cells. The terms "IL-13" and "IL-13 wild type" (abbreviated herein as IL-13, IL-13 wt) include a monomeric protein of 13 kDa polypeptide. The structure of IL-13 is described further in, for example, Moy, Diblasio et al., *J Mol Biol* 310 219-30 (2001). The term IL-13 is intended to include recombinant human IL-13 (rh IL-13), which can be prepared by standard recombinant expression methods. Additionally, the term may include orthologs/homologs of IL-13 in other species, for example, dogs, cats, cows, horses, pigs, chicken, etc.

Preferably, the IL-13 polypeptide targets of the instant disclosure include human IL-13 proteins, including, variants, fragments, isoforms, and congeners thereof. The amino acid sequence of human IL-13 is known in the art and is depicted in SEQ ID NO: 1 (NCBI accession No. AF043334.1 (ver. 1, updated Mar. 10, 2010); UNIPROT accession No. P35225 (ver. 170; reviewed Mar. 16, 2016)).

```
Sequence of human IL-13 wild type:
                                       (SEQ ID NO: 1)
MALLLTTVIALTCLGGFASPGPVPPSTALRELIEELVNITQNQKAPLCNGS

MVWSINLTAGMYCAALESLINVSGCSAIEKTQRMLSGFCPHKVSAGQFSSL

HVRDTKIEVAQFVKDLLLHLKKLFREGRFN.
```

The term "IL-13 variant" (abbreviated herein as IL-13v), as used herein, includes any variant of IL-13. An example of a human IL-13 variant is wherein amino acid residue 130 of SEQ ID NO: 1 is changed from Arginine to Glutamine (R130Q). This particular human IL-13 variant sequence is known in the art (NCBI accession No. AAH96141.2 (ver. 2, updated Sep. 23, 2014)).

The receptor portion of the IL-13 ligand/receptor system comprises a multimeric, transmembrane receptor that includes the alpha chain of the IL-4 receptor (IL-4R$\alpha$) and at least one of two known IL-13-specific binding chains (Wynn et al., Annu. Rev. Immunol. 21: 425-56 (2003)). The effects are mediated primarily via a transcription factor, signal transducer and activator of transcription 6 (STAT6).

Particularly, the antibody or an antigen-binding fragment thereof specifically binds to an IL-13 polypeptide, thereby diminishing or neutralizing the binding of the IL-13 ligand to its cognate receptor. Concomitantly, the IL-13 antibody, or antigen-binding portion thereof, may result in the inhibition and/or neutralization of the biological activity of the IL-13 ligand/receptor system.

"Biological activity" as used herein, refers to all inherent biological properties of the cytokine. Biological properties of IL-13 include but are not limited to binding IL-13 receptor to elicit inflammation, enhanced secretion of chemokines, increased migration of allergic effector cells, metaplasia, etc. in the epithelial tissue surrounding the mucosa of the GI tract. Additionally, IL-13 has been shown to induce 20% of the EE transcriptome, and more particularly to induce eotaxin-3 expression in primary esophageal epithelial cells (Blanchard et al., *J Allergy Clin Immunol.*, 120:1292, 2007).

The terms "specific binding" or "specifically binding", as used herein, in reference to the interaction of an antibody, a protein, or a peptide with a second chemical species, mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

The term "antibody", as used herein, broadly refers to any immunoglobulin (Ig) molecule comprised of four polypeptide chains, two heavy (H) chains and two light (L) chains, or any functional fragment, mutant, variant, or derivation thereof, which retains the essential epitope binding features of an Ig molecule. Such mutant, variant, or derivative antibody formats are known in the art. Non-limiting embodiments of which are discussed herein. In one embodiment, the antibody used in the compositions and methods of the disclosure is the anti-IL-13 antibody 13C5.5 described in U.S. Pat. No. 7,915,388, incorporated by reference herein. In another embodiment, the antibody used in the compositions and methods of the disclosure is the antibody 6A1, 3G4, tralokinumab, lebrikizumab, dectrekumab (QAX-576), IMA-638 or IMA-026.

In a full-length antibody, each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, PR3, CDR3, FR4 Immunoglobulin molecules can be of any type (e.g., IgG, IgE, IgM, IgD, IgA and IgY), class (e.g., IgG 1, IgG2, IgG 3, IgG4, IgA1 and IgA2) or subclass.

The term "antigen-binding portion" of an antibody (or simply "antibody portion"), as used herein, refers to one or more fragments of an antibody that retain the ability to specifically bind to an antigen (e.g., IL-13). It has been shown that the antigen-binding function of an antibody can be performed by fragments of a full-length antibody. Such antibody embodiments may also be bispecific, dual specific, or multi-specific formats; specifically binding to two or more different antigens. Examples of binding fragments encompassed within the term "antigen-binding portion" of an antibody include (i) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546, Winter et al., PCT publication WO 90/05144 A1 herein incorporated by reference), which comprises a single variable domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger et al., Proc. Natl. Acad. Sci. USA 90:6444-6448 (1993); Poljak et al., Structure 2:1121-1123 (1994)). Such antibody binding portions are known in the art (Kontermann and Dubel eds., *Antibody Engineering* (2001) Springer-Verlag. New York. 790 pp. (ISBN 3-540-41354-5).

The term "antibody construct" as used herein refers to a polypeptide comprising one or more the antigen binding portions of the disclosure linked to a linker polypeptide or an immunoglobulin constant domain. Linker polypeptides comprise two or more amino acid residues joined by peptide bonds and are used to link one or more antigen binding portions. Such linker polypeptides are well known in the art (see e.g., Holliger et al., *Proc. Natl. Acad. Sci. USA* 90:6444-6448 (1993); Poljak et al., Structure 2:1121-1123 (1994)). An immunoglobulin constant domain refers to a heavy or light chain constant domain. Human IgG heavy chain and light chain constant domain amino acid sequences are known in the art and disclosed in Table 2 of U.S. Pat. No. 7,915,388, the entire contents of which are incorporated herein by reference.

Still further, an antibody or antigen-binding portion thereof may be part of a larger immunoadhesion molecules, formed by covalent or noncovalent association of the antibody or antibody portion with one or more other proteins or peptides. Examples of such immunoadhesion molecules include use of the streptavidin core region to make a tetrameric scFv molecule (Kipriyanov et al., *Human Antibodies and Hybridomas* 6:93-101 (1995)) and use of a cysteine residue, a marker peptide and a C-terminal polyhistidine tag to make bivalent and biotinylated scFv molecules (Kipriyanov et al., Mol. Immunol. 31:1047-1058 (1994)). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein.

An "isolated antibody", as used herein, is intended to refer to an antibody that is substantially free of other antibodies having different antigenic specificities (e.g., an isolated antibody that specifically binds IL-13 is substantially free of antibodies that specifically bind antigens other than IL-13). An isolated antibody that specifically binds IL-13 may, however, have cross-reactivity to other antigens, such as IL-13 molecules from other species. Moreover, an isolated antibody may be substantially free of other cellular material and/or chemicals.

The term "human antibody", as used herein, is intended to include antibodies having variable and constant regions derived from human germline immunoglobulin sequences. The human antibodies of the disclosure may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The term "recombinant human antibody", as used herein, is intended to include all human antibodies that are prepared, expressed, created or isolated by recombinant means, such as antibodies expressed using a recombinant expression vector transfected into a host cell (described further in U.S. Pat. No. 7,915,388, the contents of which are incorporated herein by reference), antibodies isolated from a recombinant, combinatorial human antibody library (Hoogenboom et al., TIB Tech. 15:62-70 (1994); Azzazy et al., *Clin. Biochem.* 35:425-445 (2002); Gavilondo et al., *BioTechniques* 29:128-145 (2002); Hoogenboom et al., Immunology Today 21:371-378 (2000)), antibodies isolated from an animal (e.g., a mouse) that is transgenic for human immunoglobulin genes (see e.g., Taylor et al., *Nucl. Acids Res.* 20:6287-6295 (1992); Kellermann et al., Current Opinion in Biotechnology 13:593-597 (2002); Little et al., *Immunology Today* 21:364-370 (2002)) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo. One embodiment provides fully human antibodies capable of binding human IL-13 which can be generated using techniques well known in the art, such as, but not limited to, using human Ig phage libraries such as those disclosed in Jermutus et al., PCT publication No. WO 2005/007699 A2.

The term "chimeric antibody" refers to antibodies which comprise heavy and light chain variable region sequences from one species and constant region sequences from another species, such as antibodies having murine heavy and light chain variable regions linked to human constant regions. Methods for producing chimeric antibodies are known in the art and discussed in to detail in Example 2.1. See e.g., Morrison, *Science* 229:1202 (1985); Oi et al., *BioTechniques* 4:214 (1986); Gillies et al., (1989) *J. Immunol. Methods* 125:191-202; U.S. Pat. Nos. 5,807,715; 4,816,567; and 4,816,397, which are incorporated herein by reference in their entireties. In addition, "chimeric antibodies" may be produced by art-known techniques. See, Morrison et al., 1984, *Proc. Natl. Acad. Sci.* 81:851-855; Neuberger et al., 1984, *Nature* 312:604-608; Takeda et al., 1985, *Nature* 314:452-454 which are incorporated herein by reference in their entireties.

In one embodiment, the chimeric antibodies for use in the compositions and/or methods of the disclosure are produced by replacing the heavy chain constant region of the murine monoclonal anti human IL-13 antibodies described in section 1 with a human IgG1 constant region. In a specific embodiment the chimeric antibody of the disclosure comprises a heavy chain variable region (VH) comprising the amino acid sequence of SEQ ID NO: 34; SEQ ID NO: 36; SEQ ID NO: 41; SEQ ID NO: 42; or SEQ ID NO: 46 and a light chain variable region (VL) comprising the amino acid sequence of SEQ ID NO: 35; SEQ ID NO: 37; SEQ ID NO: 40; SEQ ID NO: 43; or SEQ ID NO: 47 disclosed in U.S. Pat. No. 7,915,388. Any combination of the aforementioned VH and VL sequences may be employed.

The term "CDR-grafted antibody" refers to antibodies which comprise heavy and light chain variable region sequences from one species but in which the sequences of one or more of the CDR regions of VH and/or VL are replaced with CDR sequences of another species, such as antibodies having murine heavy and light chain variable regions in which one or more of the murine CDRs (e.g., CDR3) has been replaced with human CDR sequences.

The term "humanized antibody" refers to antibodies which comprise heavy and light chain variable region sequences from a non-human species (e.g., a mouse) but in which at least a portion of the VH and/or VL sequence has been altered to be more "human-like", i.e., more similar to human germline variable sequences. One type of humanized antibody is a CDR-grafted antibody, in which human CDR sequences are introduced into non-human VH and VL sequences to replace the corresponding nonhuman CDR sequences. In one embodiment, humanized anti human IL-13 antibodies and antigen binding portions are provided. Such antibodies were generated by obtaining murine anti-IL-13 monoclonal antibodies using traditional hybridoma technology followed by humanization using in vitro genetic engineering, such as those disclosed in Kasaian et al PCT publication No. WO 2005/123126 A2. Human Ig sequences are known in the art. See, e.g., Kabat et al., Sequences of Proteins of Immunological Interest, U.S. Dept. Health (1983), entirely incorporated herein by reference. Such imported sequences can be used to reduce immunogenicity or reduce, enhance or modify binding, affinity, on-rate, off-rate, avidity, specificity, half-life, or any other suitable characteristic, as known in the art.

Framework residues in the human framework regions may be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., *Nature* 332:323 (1988), which are incorporated herein by reference in their entireties.) Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding. Antibodies can be humanized using a variety of techniques known in the art, such as but not limited to those described in Jones et al., *Nature* 321:522 (1986); Verhoeyen et al., *Science* 239:1534 (1988)), Sims et al., *J. Immunol.* 151: 2296 (1993); *Chothia and Lesk, J. Mol. Biol.* 196:901 (1987), Carter et al., *Proc. Natl. Acad. Sci. U.S.A.* 89:4285 (1992); Presta et al., *J. Immunol.* 151:2623 (1993), *Padlan, Molecular Immunology* 28(4/5):489-498 (1991); Studnicka et al., *Protein Engineering* 7(6):805-814 (1994), Roguska. et al., *PNAS* 91:969-973 (1994); PCT publication WO 91/09967, PCT/: US98/16280, US96/18978, US91/09630, US91/05939, US94/01234, GB89/01334, GB91/01134, GB92/01755; WO90/14443, WO90/14424, WO90/14430, EP 229246, EP 592,106; EP 519,596, EP 239,400, U.S. Pat. Nos. 5,565,332, 5,723,323, 5,976,862, 5,824,514, 5,817,483, 5,814,476, 5,763,192, 5,723,323, 5,766886, 5,714,352, 6,204,023, 6,180,370, 5,693,762, 5,530,101, 5,585,089, 5,225,539; 4,816,567, each entirely incorporated herein by reference, included references cited therein.

Other types of libraries may be comprised of antibody fragments from a source of genes that is not explicitly biased for clones that bind to an antigen. Thus, "naïve antibody" or "natural antibody" libraries derive from natural, unimmunized, rearranged V genes. "Synthetic antibody" libraries are constructed entirely by in vitro methods, introducing areas of complete or tailored degeneracy into the CDRs of one or more V genes. "Semi-synthetic libraries" combine natural and synthetic diversity, and are often created to increase natural diversity while maintaining a desired level of functional diversity. Thus, such libraries can, for example, be created by shuffling natural CDR regions (Soderlind et al., *Nat. Biotechnol.* 18:852-856 (2000)), or by combining naturally rearranged CDR sequences from human B cells with synthetic CDR1 and CDR2 diversity (Hoet et al., Nat. Biotechnol. 23:455-38 (2005)). The present disclosure encompasses the use of naïve/natural, synthetic and semi-synthetic antibody libraries, or any combination thereof.

The terms "Kabat numbering", "Kabat definitions and "Kabat labeling" are used interchangeably herein. These terms, which are recognized in the art, refer to a system of numbering amino acid residues which are more variable (i.e. hypervariable) than other amino acid residues in the heavy and light chain variable regions of an antibody, or an antigen binding portion thereof (Kabat et al. (1971) *Ann. NY Acad, Sci.* 190:382-391 and, Kabat, E. A., et al. (1991) Sequences of Proteins of Immunological Interest, Fifth Edition, U.S. Department of Health and Human Services, NIH Publication No. 91-3242). For the heavy chain variable region, the hypervariable region ranges from amino acid positions 31 to 35 for CDR1, amino acid positions 50 to 65 for CDR2, and amino acid positions 95 to 102 for CDR3. For the light chain variable region, the hypervariable region ranges from amino acid positions 24 to 34 for CDR1, amino acid positions 50 to 56 for CDR2, and amino acid positions 89 to 97 for CDR3.

As used herein, the terms "acceptor" and "acceptor antibody" refer to the antibody or nucleic acid sequence providing or encoding at least 80%, at least 85%, at least 90%, at least 95%, at least 96%, at least 97%, at least 98%, at least 99%, or 100% of the amino acid sequences of one or more of the framework regions. In some embodiments, the term "acceptor" refers to the antibody amino acid or nucleic acid sequence providing or encoding the constant region(s). In yet another embodiment, the term "acceptor" refers to the antibody amino acid or nucleic acid sequence providing or encoding one or more of the framework regions and the constant region(s). In a specific embodiment, the term "acceptor" refers to a human antibody amino acid or nucleic acid sequence that provides or encodes at least 80%, preferably, at least 85%, at least 90%, at least 95%, at least 98%, or 100% of the amino acid sequences of one or more of the framework regions. In accordance with this embodiment, an acceptor may contain at least 1, at least 2, at least 3, least 4, at least 5, or at least 10 amino acid residues that does (do) not occur at one or more specific positions of a human antibody. An acceptor framework region and/or acceptor constant region(s) may be, e.g., derived or obtained from a germline antibody gene, a mature antibody gene, a functional antibody (e.g., antibodies well-known in the art, antibodies in development, or antibodies commercially available).

As used herein, the term "CDR" refers to the complementarity determining region within antibody variable sequences. There are three CDRs in each of the variable regions of the heavy chain and the light chain, which are designated CDR1, CDR2 and CDR3, for each of the variable regions. The term "CDR set" as used herein refers to a group of three CDRs that occur in a single variable region capable of binding the antigen. The exact boundaries of these CDRs have been defined differently according to different systems. The system described by Kabat (Kabat et al., Sequences of Proteins of Immunological Interest (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Chothia and coworkers (Chothia & Lesk, *J. Mol. Biol.* 196:901-917 (1987) and Chothia et al., *Nature* 342:877-883 (1989)) found that certain sub-portions within Kabat CDRs adopt nearly identical peptide backbone conformations, despite having great diversity at the level of amino acid sequence. These sub-portions were designated as L1, L2 and L3 or H1, H2 and H3 where the "L" and the "H" designates the light chain and the heavy chains regions, respectively. These regions may be referred to as Chothia CDRs, which have boundaries that overlap with Kabat CDRs. Other boundaries defining CDRs overlapping with the Kabat CDRs have been described by Padlan (*FASEB J.* 9:133-139 (1995)) and MacCallum (*J Mol Biol* 262(5):732-45 (1996)). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although preferred embodiments use Kabat or Chothia defined CDRs.

As used herein, the term "canonical" residue refers to a residue in a CDR or framework that defines a particular canonical CDR structure as defined by Chothia et al. (*J. Mol. Biol.* 196:901-907 (1987); Chothia et al., *J. Mol. Biol.* 227:799 (1992), both are incorporated herein by reference). According to Chothia et al., critical portions of the CDRs of many antibodies have nearly identical peptide backbone confirmations despite great diversity at the level of amino acid sequence. Each canonical structure specifies primarily a set of peptide backbone torsion angles for a contiguous segment of amino acid residues forming a loop.

As used herein, the terms "donor" and "donor antibody" refer to an antibody providing one or more CDRs. In a preferred embodiment, the donor antibody is an antibody from a species different from the antibody from which the framework regions are obtained or derived. In the context of a humanized antibody, the term "donor antibody" refers to a non-human antibody providing one or more CDRs.

As used herein, the term "framework" or "framework sequence" refers to the remaining sequences of a variable region minus the CDRs. Because the exact definition of a CDR sequence can be determined by different systems, the meaning of a framework sequence is subject to correspondingly different interpretations. The six CDRs (CDR-L1, CDR-L2, and CDR-L3 of light chain and CDR-H1, CDR-H2, and CDR-H3 of heavy chain) also divide the framework regions on the light chain and the heavy chain into four sub-regions (FR1, FR2, FR3 and FR4) on each chain, in which CDR1 is positioned between FR1 and FR2, CDR2 between FR2 and FR3, and CDR3 between FR3 and FR4.

Without specifying the particular sub-regions as FR1, FR2, FR3 or FR4, a framework region, as referred by others, represents the combined FR's within the variable region of a single, naturally occurring immunoglobulin chain. As used herein, a FR represents one of the four sub-regions, and FRs represents two or more of the four sub-regions constituting a framework region.

Human heavy chain and light chain acceptor sequences are known in the art. In one embodiment of the disclosure the human heavy chain and light chain acceptor sequences are selected from the sequences described in Table 3 and Table 4 disclosed in U.S. Pat. No. 7,915,388, the contents of which are incorporated herein by reference.

As used herein, the term "germline antibody gene" or "gene fragment" refers to an immunoglobulin sequence encoded by non-lymphoid cells that have not undergone the maturation process that leads to genetic rearrangement and mutation for expression of a particular immunoglobulin. (See, e.g., Shapiro et al., Crit. Rev. Immunol. 22(3): 183-200 (2002); Marchalonis et al., Adv Exp Med. Biol. 484:13-30 (2001)). One of the advantages provided by various embodiments of the present disclosure stems from the recognition that germline antibody genes are more likely than mature antibody genes to conserve essential amino acid sequence structures characteristic of individuals in the species, hence less likely to be recognized as from a foreign source when used therapeutically in that species.

As used herein, the term "key" residues refer to certain residues within the variable region that have more impact on the binding specificity and/or affinity of an antibody, in particular a humanized antibody. A key residue includes, but is not limited to, one or more of the following: a residue that is adjacent to a CDR, a potential glycosylation site (can be either N- or O-glycosylation site), a rare residue, a residue capable of interacting with the antigen, a residue capable of interacting with a CDR, a canonical residue, a contact residue between heavy chain variable region and light chain variable region, a residue within the Vernier zone, and a residue in the region that overlaps between the Chothia definition of a variable heavy chain CDR1 and the Kabat definition of the first heavy chain framework.

As used herein, the term "humanized antibody" is an antibody or a variant, derivative, analog or fragment thereof which immunospecifically binds to an antigen of interest and which comprises a framework (FR) region having substantially the amino acid sequence of a human antibody and a complementary determining region (CDR) having substantially the amino acid sequence of a non-human antibody. As used herein, the term "substantially" in the context of a CDR refers to a CDR having an amino acid sequence at least 80%, preferably at least 85%, at least 90%, at least 95%, at least 96%, at least 97%, at least 98% or at least 99% identical to the amino acid sequence of a non-human antibody CDR. A humanized antibody comprises substantially all of at least one, and typically two, variable domains (Fab, Fab', F(ab')2, FabC, Fv) in which all or substantially all of the CDR regions correspond to those of a non-human immunoglobulin (i.e., donor antibody) and all or substantially all of the framework regions are those of a human immunoglobulin consensus sequence. Preferably, a humanized antibody also comprises at least a portion of an immunoglobulin constant region (Fc), typically that of a human immunoglobulin. In some embodiments, a humanized antibody contains both the light chain as well as at least the variable domain of a heavy chain. The antibody also may include the CH1, hinge, CH2, CH3, and CH4 regions of the heavy chain. In some embodiments, a humanized antibody only contains a humanized light chain. In some embodiments, a humanized antibody only contains a humanized heavy chain. In specific embodiments, a humanized antibody only contains a humanized variable domain of a light chain and/or humanized heavy chain.

The humanized antibody can be selected from any class of immunoglobulins, including IgM, IgG, IgD, IgA and IgE, and any isotype, including without limitation IgG 1, IgG2, IgG3 and IgG4. The humanized antibody may comprise sequences from more than one class or isotype, and particular constant domains may be selected to optimize desired effector functions using techniques well-known in the art.

The framework and CDR regions of a humanized antibody need not correspond precisely to the parental sequences, e.g., the donor antibody CDR or the consensus framework may be mutagenized by substitution, insertion and/or deletion of at least one amino acid residue so that the CDR or framework residue at that site does not correspond to either the donor antibody or the consensus framework. In a preferred embodiment, such mutations, however, will not be extensive. Usually, at least 80%, preferably at least 85%, more preferably at least 90%, and most preferably at least 95% of the humanized antibody residues will correspond to those of the parental FR and CDR sequences. As used herein, the term "consensus framework" refers to the framework region in the consensus immunoglobulin sequence. As used herein, the term "consensus immunoglobulin sequence" refers to the sequence formed from the most frequently occurring amino acids (or nucleotides) in a family of related immunoglobulin sequences (See e.g., Winnaker, From Genes to Clones (Verlagsgesellschaft, Weinheim, Germany 1987). In a family of immunoglobulins, each position in the consensus sequence is occupied by the amino acid occurring most frequently at that position in the family. If two amino acids occur equally frequently, either can be included in the consensus sequence.

In one embodiment of the disclosure, the humanized anti-IL-13 antibody is 13C5.5. 13C5.5 has the sequences SEQ ID NO: 2 (heavy chain variable region) and SEQ ID NO: 3 (light chain variable region). See also U.S. Pat. No. 7,915,388, the entire contents of which are incorporated herein by reference.

```
Heavy Chain Variable Region 13C5.5
                                    (SEQ ID NO: 2)
EVTLRESGPGLVKPTQTLTLTCTLYGFSLSTSDMGVDWIRQPPGKGLEWLA

HIWWDDVKRYNPALKSRLTISKDTSKNQVVLKLTSVDPVDTATYYCARTVS

SGYIYYAMDYWGQGTLVTVSS

Light Chain Variable Region 13C5.5
                                    (SEQ ID NO: 3)
DIQMTQSPSSLSASVGDRVTISCRASQDIRNYLNWYQQKPGKAPKLLIFYT

SKLHSGVPSRFSGSGSGTDYTLTISSLQPEDIATYYCQQGNTLPLTFGGGT

KVEIK
```

13C5.5 is a humanized antibody that binds with great affinity to helices A and D of interleukin 13 (IL-13) (see US patent pub. No. 2014/0341913).

Other representative examples of IL-13 antibodies are known in the art. In one embodiment, the antibody is 6A1, 3G4, tralokinumab, lebrikizumab, QAZ-576, IMA-638 or IMA-026, or an antigen-binding portion thereof. For example, Table 5 of U.S. Pat. No. 7,915,388 (the contents of which are incorporated herein by reference) provides a list of amino acid sequences of VH and VL regions of preferred anti-IL-13 antibodies to be used in the compositions and/or methods of the disclosure. These isolated anti-IL-13 antibody CDR sequences establish a family of IL-13 binding proteins, isolated in accordance with this disclosure, and comprising polypeptides that include the CDR sequences listed in Table 6 of U.S. Pat. No. 7,915,388 (the contents of which are incorporated herein by reference). To generate and to select CDRs of the disclosure having preferred IL-13 binding and/or neutralizing activity with respect to IL-13 and/or IL-13, standard methods known in the art for generating binding proteins of the present disclosure and assessing the IL-13 and or IL-13 binding and/or neutralizing characteristics of those binding protein may be used, including but not limited to those specifically described herein.

The antibodies of the disclosure and their antigen-binding counterparts are neutralizing antibodies. As used herein, the term "neutralizing" refers to neutralization of biological activity of a cytokine when a binding protein specifically binds the cytokine. Preferably a neutralizing binding protein is a neutralizing antibody whose binding to IL-13 and/or IL-13 results in inhibition of a biological activity of IL-13 and/or IL-13. Preferably the neutralizing binding protein binds IL-13 and/or IL-13 and reduces a biologically activity of IL-13 and/or IL-13 by at least about 20%, 40%, 60%, 80%, 85% or more. Inhibition of a biological activity of IL-13 and/or IL-13 by a neutralizing binding protein can be assessed by measuring one or more indicators of IL-13 and/or IL-13 biological activity well known in the art. For example, inhibition of human IL-13 induced production of TARC (CCL-17) by A-549 cells can be measured (see Example 1.1.0 of U.S. Pat. No. 7,915,388, which is incorporated herein by reference).

The term "activity" includes activities such as the binding specificity/affinity of an antibody for an antigen, for example, an anti-IL-13 antibody that binds to an IL-13 antigen and/or the neutralizing potency of an antibody, for example, an anti-IL-13 antibody whose binding to IL-13 inhibits the biological activity of IL-13, e.g. For example inhibition of human IL-13 induced production of TARC (CCL-17) by A-549 cells (see Example 1.1.0 of U.S. Pat. No. 7,915,388, which is incorporated herein by reference).

The term "epitope" includes any polypeptide determinant capable of specific binding to an immunoglobulin or T-cell receptor. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics. An epitope is a region of an antigen that is bound by an antibody. In certain embodiments, an antibody is said to specifically bind an antigen when it preferentially recognizes its target antigen in a complex mixture of proteins and/or macromolecules.

Any known method may be employed to detect antibody-antigen interactions. For example, surface plasmon resonance (SPR) is an optical phenomenon that permits analysis of biospecific interactions by detection of alterations in protein concentrations within a biosensor matrix, for example using the BIACORE system (Pharmacia Biosensor, Piscataway, N.J.). See Jonsson et al. (1993) *Ann. Biol. Clin.* 51:19-26; Jonsson et al. (1991) *Biotechniques* 11:620-627; Johnsson et al. (1995) *J. Mol. Recognit.* 8:125-131; and Johnnson, B., et al. (1991) *Anal. Biochem.* 198:268-277.

The anti-IL-13 antibodies used in the context of the methods of the present disclosure may have pH-dependent binding characteristics. For example, an anti-IL-13 antibody for use in the methods of the present disclosure may exhibit reduced binding to IL-13 at acidic pH as compared to neutral pH. Alternatively, an anti-IL-13 antibody of the disclosure may exhibit enhanced binding to its antigen at acidic pH as compared to neutral pH. The expression "acidic pH" includes pH values less than about 6.2, e.g., about 6.0, 5.95, 5.9, 5.85, 5.8, 5.75, 5.7, 5.65, 5.6, 5.55, 5.5, 5.45, 5.4, 5.35, 5.3, 5.25, 5.2, 5.15, 5.1, 5.05, 5.0, or less. As used herein, the expression "neutral pH" means a pH of about 7.0 to about 7.4. The expression "neutral pH" includes pH values of about 7.0, 7.05, 7.1, 7.15, 7.2, 7.25, 7.3, 7.35, and 7.4.

In certain instances, "reduced binding to IL-13 at acidic pH as compared to neutral pH" is expressed in terms of a ratio of the $K_D$ value of the antibody binding to IL-13 at acidic pH to the $K_D$ value of the antibody binding to IL-13 at neutral pH (or vice versa). For example, an antibody or antigen-binding fragment thereof may be regarded as exhibiting "reduced binding to IL-13 at acidic pH as compared to neutral pH" for purposes of the present disclosure if the antibody or antigen-binding fragment thereof exhibits an acidic/neutral KD ratio of about 3.0 or greater. In certain exemplary embodiments, the acidic/neutral KD ratio for an antibody or antigen-binding fragment of the present disclosure can be about 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 20.0, 25.0, 30.0, 40.0, 50.0, 60.0, 70.0, 100.0, or greater.

Antibodies with pH-dependent binding characteristics may be obtained, e.g., by screening a population of antibodies for reduced (or enhanced) binding to a particular antigen at acidic pH as compared to neutral pH. Additionally, modifications of the antigen-binding domain at the amino acid level may yield antibodies with pH-dependent characteristics. For example, by substituting one or more amino acids of an antigen-binding domain (e.g., within a CDR) with a histidine residue, an antibody with reduced antigen-binding at acidic pH relative to neutral pH may be obtained. As used herein, the expression "acidic pH" means a pH of 6.0 or less.

The aforementioned antibodies may be conjugated to other moieties and/or agents to achieve desired properties, e.g., physiological stability, increased half-life, increased bioavailability, etc. The term "antibody conjugate" refers to a binding protein, such as an antibody, chemically linked to a second chemical moiety, such as a therapeutic or cytotoxic agent. In other instances, the chemical moiety may be a diagnostic agent, e.g., a radio-ligand. The term "agent" is used herein to denote a chemical compound, a mixture of chemical compounds, a biological macromolecule, or an extract made from biological materials. Preferably the therapeutic or cytotoxic agents include, but are not limited to, pertussis toxin, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

The term "regulate" and "modulate" are used interchangeably, and, as used herein, refers to a change or an alteration in the activity of a molecule of interest (e.g., the biological activity of IL-13). Modulation may be an increase or a decrease in the magnitude of a certain activity or function of the molecule of interest. Exemplary activities and functions of a molecule include, but are not limited to, binding characteristics, enzymatic activity, cell receptor activation, and signal transduction.

Correspondingly, the term "modulator," as used herein, is a compound capable of changing or altering an activity or function of a molecule of interest (e.g., the biological activity of IL-13). For example, a modulator may cause an increase or decrease in the magnitude of a certain activity or function of a molecule compared to the magnitude of the activity or function observed in the absence of the modulator. In certain embodiments, a modulator is an inhibitor, which decreases the magnitude of at least one activity or function of a molecule. Exemplary inhibitors include, but are not limited to, proteins, peptides, antibodies, peptibodies, carbohydrates or small organic molecules. Peptibodies are described, e.g., in WO 01/83525.

The term "agonist", as used herein, refers to a modulator that, when contacted with a molecule of interest, causes an increase in the magnitude of a certain activity or function of the molecule compared to the magnitude of the activity or function observed in the absence of the agonist. Particular agonists of interest may include, but are not limited to, IL-13 polypeptides or polypeptides, nucleic acids, carbohydrates, or any other molecules that bind to IL-13.

The term "antagonist" or "inhibitor", as used herein, refer to a modulator that, when contacted with a molecule of interest causes a decrease in the magnitude of a certain activity or function of the molecule compared to the magnitude of the activity or function observed in the absence of the antagonist. Particular antagonists of interest include those that block or modulate the biological or immunological activity of IL-13 and/or IL-13v. Antagonists and inhibitors of IL-13 and/or IL-13v may include, but are not limited to, proteins; nucleic acids, carbohydrates, or any other molecules, which bind to IL-13 or IL-13v.

The term "inhibit binding to the receptor" refers to the ability of the binding protein to prevent the binding of IL-13 to one or more of its receptors. Such inhibition of binding to the receptor would result in diminishing or abolishing the biological activity mediated by binding of IL-13 to its receptor or receptors.

As used herein, the term "effective amount" refers to the amount of an antibody, or antigen-binding portion thereof, which is sufficient to reduce or ameliorate the severity and/or duration of a disorder or one or more symptoms thereof, prevent the advancement of a disorder, cause regression of a disorder, prevent the recurrence, development, onset or progression of one or more symptoms associated with a disorder, detect a disorder, or enhance or improve the prophylactic or therapeutic effect(s) of another therapy (e.g., prophylactic or therapeutic agent).

A. Pharmaceutical Compositions

The present disclosure includes methods which comprise administering an IL-13 antibody, or antigen-binding portion thereof, to a subject wherein the IL-13 antibody, or antigen-binding portion thereof, is contained within a pharmaceutical composition. The pharmaceutical compositions may be formulated with suitable carriers, excipients, and other agents that provide suitable transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

Various delivery systems are known and can be used to administer the pharmaceutical composition, e.g., encapsulation in liposomes, microparticles, microcapsules, recombinant cells capable of expressing the mutant viruses, receptor mediated endocytosis (see, e.g., Wu et al., 1987, J. Biol. Chem. 262: 4429-4432). Methods of administration include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents.

A pharmaceutical composition can be delivered subcutaneously or intravenously with a standard needle and syringe. In addition, with respect to subcutaneous delivery, a pen delivery device readily has applications in delivering a pharmaceutical composition. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

In certain situations, the pharmaceutical composition can be delivered in a controlled release system. In one embodiment, a pump may be used. In another embodiment, polymeric materials can be used; see, Medical Applications of Controlled Release, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by known methods. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc.

Exemplary pharmaceutical compositions comprising an anti-IL-13 antibody that can be used in the context of the present disclosure are disclosed, e.g., in US patent app. Pub. No. 2012/0097565, the entire contents of which are expressly incorporated herein by reference.

The present disclosure provides a pharmaceutical composition comprising one or more of the aforementioned IL-13 antibodies, and antigen-binding portions thereof, and a pharmaceutically acceptable carrier. Additionally, in a related embodiment, the present disclosure provides a diagnostic composition comprising one or more of the aforementioned IL-13 antibodies, and antigen-binding portions thereof, and a plurality of reagents, buffers, and carriers for diagnostic testing. According this aspect, the pharmaceutical composition may be formulated for intravenous administration, subcutaneous administration, intraperitoneal administration, or intramuscular administration. Still further according to this aspect, the pharmaceutical composition may be formulated for subcutaneous administration as a microneedle patch. The pharmaceutical compositions may be formulated for parenteral administration by bolus injection or by gradual perfusion over time. The diagnostic composition may be formulated for in vitro, in vivo, or ex vivo application.

Exemplary agents used in formulating the aforementioned IL-13 antibodies, and antigen-binding portions thereof, into pharmaceutical compositions and/or diagnostic compositions are provided in US patent pub. No. 2014/0341913, which is incorporated by reference herein. Specifically, exemplary agents used in formulating the aforementioned IL-13 antibodies, and antigen-binding portions thereof, into pharmaceutical compositions for the treatment of EoE are provided in US patent pub. No. 2015/0017176, which is incorporated by reference herein.

B. Dosage and Administration

The amount of IL-13 antibody, or antigen-binding portion thereof, administered to a subject according to the methods of the present disclosure is, generally, a therapeutically effective amount. As used herein, the phrase "therapeutically effective amount" means an amount of IL-13 antibody, or antigen-binding portion thereof, that results in one or more of: (a) a reduction in the severity or duration of a symptom of eosinophilic esophagitis; (b) a reduction in the number of eosinophils in esophagus; (c) prevention or alleviation of an allergic reaction; and (d) a reduction in the use or need for conventional allergy therapy (e.g., reduced or eliminated use of antihistamines, decongestants, nasal or inhaled steroids, anti-IgE treatment, epinephrine, etc.).

In the case of an anti-IL-13 antibody, or antigen-binding portion thereof, the instant invention provides the surprising results of a phase II clinical trial demonstrating that a therapeutically effective is about 180 mg to about 360 mg of the antibody, or antigen-binding portion thereof, administered subcutaneously on a weekly dosing regimen. In one embodiment, a therapeutically effective amount is about 180 mg of the antibody, or antigen-binding portion thereof. In another embodiment, the therapeutically effective amount is about 360 mg of the antibody, or antigen-binding portion thereof. In one embodiment, a therapeutically effective amount can be about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg or more of the anti-IL-13 antibody, or antigen-binding portion thereof. In another embodiment, the therapeutically effective amount is about 160 mg to about 200 mg of the antibody, or antigen-binding portion thereof. In another embodiment, the therapeutically effective amount is about 340 mg to about 380 mg of the antibody, or antigen-binding portion thereof. In another embodiment, the therapeutically effective amount is about 160 mg to about 200 mg of the antibody, or antigen-binding portion thereof. In another embodiment, the therapeutically effective amount is about 160 mg to about 200 mg, about 170 mg to about 210 mg, about 180 mg to about 220 mg, about 190 mg to about 230 mg, about 200 mg to about 240 mg, about 210 mg to about 250 mg, about 220 mg to about 260 mg, about 230 mg to about 270 mg, about 240 mg to about 280 mg, about 250 mg to about 290 mg, about 260 mg to about 300 mg, about 270 mg to about 310 mg, about 280 mg to about 320 mg, about 290 mg to about 330 mg, about 300 mg to about 340 mg, about 310 mg to about 350 mg, about 320 mg to about 360 mg, about 330 mg to about 370 mg, or about 340 mg to about 380 mg of the antibody, or antigen-binding portion thereof.

In one embodiment, the composition of the disclosure is administered once. In another embodiment, the composition is administered weekly. In another embodiment, the composition is administered for two weeks. In another embodiment, the composition is administered for three weeks. In another embodiment, the composition is administered for four weeks, five weeks, six weeks, seven weeks, eight weeks, nine weeks, ten weeks, eleven weeks, three months, four months, five months, six months, seven months, eight months, nine months, ten months, eleven months, twelve months, thirteen months, fourteen months, fifteen months, sixteen months, seventeen months, eighteen months, nineteen months, twenty months, twenty-one months, twenty-two months, twenty-three months, two years, three years, four years, five years, ten years, for the duration of the disease, or for the life of the subject.

In one embodiment, the composition is administered subcutaneously. In another embodiment, the composition is administered intravenously. In one embodiment, the composition is administered intravenously for one administration, followed by weekly subcutaneous dosages. In one embodiment, the first administration of the antibody, or antigen-binding portion thereof, is at a dosage of 5 mg/kg intravenously, followed by weekly subcutaneous administration of the antibody, or antigen-binding portion thereof, at a dosage of 180 mg. In another embodiment, the first administration of the antibody, or antigen-binding portion thereof, is at a dosage of 10 mg/kg intravenously, followed by weekly subcutaneous administration of the antibody, or antigen-binding portion thereof, at a dosage of 360 mg.

The dose of the pharmaceutical compositions may be altered depending on the age, sex, health, and weight of the recipient, kind of concurrent treatment, if any, frequency of treatment, and the nature of the effect desired. Formulation used as preclinical and clinical therapeutics or in clinical diagnostics may be produced by those of skill, employing accepted principles of diagnosis and treatment. The dose ranges for the compositions may be large enough to produce the desired effect. Likewise, the dose of the diagnostic composition may be altered depending on the nature of the diagnosis, e.g., in vitro versus in vivo application. Methods of formulating the IL-13 antibodies, and antigen-binding portions thereof, into diagnostic agents, e.g., chelating an antibody to a diagnostic agent selected from a radiolabel, a colorimetric moiety, a fluorescent moiety, a chemiluminescent moiety, an enzymatic moiety, and immunogenic moiety, are known in the art.

The aforementioned compositions and pharmaceutical preparations may be packaged in the form of kits. The term "kit" as used herein refers to a packaged product comprising components with which to administer the anti-IL-13 antibody of the disclosure for treatment of a IL-13 related disorder. The kit preferably comprises a box or container that holds the components of the kit. The box or container is affixed with a label or a Food and Drug Administration approved protocol. The box or container holds components of the disclosure which are preferably contained within plastic, polyethylene, polypropylene, ethylene, or propylene vessels. The vessels can be capped-tubes or bottles. The kit can also include instructions for administering an anti-IL-13 antibody.

C. Combination Therapies

The term "combination therapy", as used herein, refers to the administration of two or more therapeutic substances, e.g., an anti-IL-13 antibody and another agent. The other drug(s) may be administered concomitant with, prior to, or following the administration of the anti-IL-13 antibody. Particularly, the additional agent is an agent that is useful in the diagnosis and/or therapy of eosinophilic disorders. Especially, the additional agent is an agent that is useful in the therapy/diagnosis of eosinophilic gastrointestinal disorders (EGID).

In the context of diagnosis and/or therapy of EGID, the additional agent may be selected from the group consisting of: a therapeutic agent, an imaging agent, a cytotoxic agent, an angiogenesis inhibitor, a kinase inhibitor, a co-stimulation molecule blocker, an adhesion molecule blocker, an anti-cytokine antibody or functional fragment thereof; methotrexate, a cyclosporin, a rapamycin, an FK506, a detectable label or reporter, a TNF antagonist, an antirheumatic, a muscle relaxant, a narcotic, a non-steroid anti-inflammatory drug (NSAID), an analgesic, an anesthetic, a sedative, a local anesthetic, a neuromuscular blocker, an antimicrobial, an antipsoriatic, a corticosteroid, an anabolic steroid, an erythropoietin, an immunization, an immunoglobulin, an immunosuppressive, a growth hormone, a hormone replacement drug, a radiopharmaceutical, an antidepressant, an antipsychotic, a stimulant, an asthma medication, a beta agonist, an inhaled steroid, an oral steroid, an epinephrine or analog, a cytokine, and a cytokine antagonist.

Particularly in the context of therapy of EGID, the additional agent is selected from the group consisting of an IL-113 inhibitor, an IL-5 inhibitor, an IL-9 inhibitor, an IL-17 inhibitor, an IL-25 inhibitor, a TNF-α inhibitor, an eotaxin-3 inhibitor, an IgE inhibitor, a prostaglandin D2 inhibitor, an immunosuppressant, a corticosteroid, a glucocorticoid, a proton pump inhibitor, a NSAID, an agent for allergen removal and an agent aiding diet management.

The term "combination" as in the phrase "a first agent in combination with a second agent" includes co-administration of a first agent and a second agent, which for example may be dissolved or intermixed in the same pharmaceutically acceptable carrier, or administration of a first agent, followed by the second agent, or administration of the second agent, followed by the first agent. The present disclosure, therefore, includes methods of combination therapeutic treatment and combination pharmaceutical compositions.

The term "concomitant" as in the phrase "concomitant therapeutic treatment" includes administering an agent in the presence of a second agent. A concomitant therapeutic treatment method includes methods in which the first, second, third, or additional agents are co-administered. A concomitant therapeutic treatment method also includes methods in which the first or additional agents are administered in the presence of a second or additional agents, wherein the second or additional agents, for example, may have been previously administered. A concomitant therapeutic treatment method may be executed step-wise by different actors. For example, one actor may administer to a subject a first agent and a second actor may to administer to the subject a second agent, and the administering steps may be executed at the same time, or nearly the same time, or at distant times, so long as the first agent (and additional agents) are after administration in the presence of the second agent (and additional agents). The actor and the subject may be the same entity (e.g., human).

II. Disorders in which IL-13 Activity is Detrimental

As used herein, the term "a disorder in which IL-13 activity is detrimental" is intended to include diseases and other disorders in which the presence of IL-13 in a subject suffering from the disorder has been shown to be or is suspected of being either responsible for the pathophysiology of the disorder or a factor that contributes to a worsening of the disorder. In one embodiment, the disorder in which IL-13 activity is detrimental is asthma, e.g., mild asthma or moderate asthma. In another embodiment, the disorder in which IL-13 activity is detrimental is eosinophilic esophagitis (EoE).

Accordingly, a disorder in which IL-13 activity is detrimental is a disorder in which reduction of IL-13 activity is expected to alleviate the symptoms and/or progression of the disorder. Such disorders may be evidenced, for example, by an increase in the concentration of IL-13 in a biological fluid of a subject suffering from the disorder (e.g., an increase in the concentration of IL-13 in serum, plasma, synovial fluid, etc. of the subject), which can be detected, for example, using an anti-IL-13 antibody as described above. Non-limiting examples of disorders that can be treated with the antibodies of the invention include asthma, e.g., mild or moderate asthma, eosinophilic esophagitis, as well as those disorders discussed in the sections below pertaining to pharmaceutical compositions of the antibodies of the invention.

IL-13 has been implicated as having a pivotal role in causing pathological responses associated with asthma and Eoe. However other mediators of differential immunological pathways are also involved in disease pathogenesis, and blocking these mediators, in addition to IL-13, may offer additional therapeutic benefit.

A. Eosinophilic Disorders, Such as Eosinophilic Esophagitis (EoE)

In one embodiment, the eosinophilic disorder that can be treated using the anti-IL-13 antibodies, and antigen-binding portions thereof, disclosed herein, is an eosinophilic gastrointestinal disorder (EGID). Eosinophilic gastrointestinal disorders are defined as disorders that selectively affect the gastrointestinal tract with eosinophil-rich inflammation in the absence of known causes for eosinophilia (e.g., drug reactions, parasitic infections, and malignancy). Examples of EGIDs that are treatable with the compositions of the instant disclosure (collectively termed "disorders of the instant disclosure") include, but are not limited to, eosinophilic esophagitis (EoE), eosinophilic gastritis (EoG), eosinophilic duodenitis (ED), eosinophilic jejunitis (EJ), eosinophilic ileitis (EI), and eosinophilic colitis (EC).

The aforementioned diseases may be individually or collectively presented in subjects. The frequency of diagnosis may vary depending on age, sex, race, and other relevant genetic and/or environmental factors. For instance, eosinophilic esophagitis (allergic esophagitis) is perhaps the most common EGID, affecting roughly 1% of the population. EoE is an allergic inflammatory condition of the esophagus that involves infiltration of eosinophils (Arora et al., *Gastroenterology and Hepatology*, vol. 2, no. 7, pp. 523-530 (2004)). On the other hand, eosinophilic gastroenteritis (EG) is a rare and heterogeneous condition characterized by patchy or diffuse eosinophilic infiltration of gastrointestinal tissue, e.g., tissues lining the stomach, small intestine and colon (Whitaker et al., *Eur J Gastroenterol Hepatol.*, 16(4):407-9 (2004)). Eosinophilic duodenitis (ED) is most frequently observed in pediatric patients and is characterized by eosinophilic inflammation of the small bowel that results in the production of leukotrienes (Gaertner et al., *Gastroenterology Research and Practice*, Article ID 857508 (2011)). Eosinophilic ileitis (EI) is characterized by mass infiltration of eosinophils and mast cells into the ileum and is frequently characterized by perforation and remodeling of intestinal wall (Lombardi et al., *Allergy*, 62, 1343-1345 (2011)). Eosinophilic jejunitis (EJ) is a rare disorder characterized by infiltration of eosinophils in the intestine and is characterized by abdominal pain and obstructive symptoms concomitant with weight loss (Caliskan et al., *Langenbecks Arch Surg.*, 395:99-101 (2010)).

"Eosinophilic Esophagitis" (EoE), as used herein, refers to an inflammatory disease characterized by abnormal eosinophilic inflammation within the esophagus and esophageal dysfunction. The primary symptoms of EoE include, but are not limited to, chest and abdominal pain, dysphagia, heartburn, food refusal, vomiting and food impaction. The clinicopathology of EoE is characterized by presence of ridges or trachea-like rings in the esophageal wall and eosinophilic infiltration in the esophageal mucosa. EoE is presently diagnosed by endoscopy of the esophagus followed by microscopic and biochemical analysis of the esophageal mucosal lining. EoE may be classified as allergic or non-allergic depending upon the status of the subject. In one embodiment, the methods disclosed herein are useful for treating allergic EoE. In another embodiment, the methods disclosed herein are useful for treating non-allergic EoE.

As used herein, the terms "treat", "treating", or the like, mean to alleviate symptoms, eliminate the causation of symptoms either on a temporary or permanent basis, or to prevent or slow the appearance of symptoms of eosinophilic inflammation in the esophagus. In certain embodiments, the present methods are useful for reducing the incidence of symptoms or indications associated with an eosinophilic disorder, e.g., EoE. Particular embodiments of the disclosure relate to methods for treating or ameliorating at least one symptom or indication associated with an eosinophilic disorder.

In these embodiments, the present methods are useful for treating or ameliorating at least one symptom or indication of eosinophilic gastrointestinal disorder (EGID). The EGID is particularly selected from the group consisting of eosinophilic esophagitis (EoE), eosinophilic gastritis (EoG), eosinophilic duodenitis (ED), eosinophilic jejunitis (EJ), eosinophilic ileitis (EI) and eosinophilic colitis (EC). The symptoms or indications that are treatable in accordance with this embodiment include, but are not limited to, eosinophilic infiltration, remodeling of GI tract, perforation, inflammation, obstruction of bowel movement, constipation, abdominal pain, weight loss and the like.

Specifically, the present methods are useful for treating or ameliorating at least one symptom or indication of eosinophilic esophagitis (EoE). The symptoms or indications associated with EoE that are treatable in accordance with this embodiment include, but are not limited to, inflammation of the esophagus, thickening of the esophageal wall, appearance of trachea-like rings or ridges in the esophagus, chest and abdominal pain, food refusal, vomiting, dysphagia and food impaction.

In these embodiments, the therapeutic compositions of the instant disclosure are administered to subjects in need of such compositions. As used herein, the expression "a subject in need thereof" means a human or non-human mammal that exhibits one or more symptoms or indications of eosinophilic disorder and/or who has been diagnosed with eosinophilic disorder. Particularly, the subject exhibits one or more symptoms or indications associated with an EGID, wherein the EGID is selected from the group consisting of EoE, EG, ED, EI, EJ, and EC. Especially, the subject exhibits one or more symptoms or indications associated with eosinophilic esophagitis (EoE).

In certain embodiments, the methods of the present disclosure may be used to treat subjects that show elevated levels of one or more EGID-associated markers. For example, the methods of the present disclosure comprise treating subjects with elevated levels of serum IgE (allergen specific IgE or global pool of IgE or both) or elevated eotaxin-3 levels. In other embodiments, the subjects may display other physiological markers, such as, e.g., overexpression of pro-inflammatory mediators such as mast cells, enhanced eosinophilic infiltration of the mucosal membrane, thickening of the epithelial lining, dysphagia, food impaction, chest and abdominal pain, or a combination thereof. In one embodiment, the elevated level is a two-fold increase in marker expression as compared to a control level of the marker in a subject not having EoE. In one embodiment, the elevated level is a 3-fold, 4-fold, or 5-fold increase in marker expression as compared to a control level of the marker in a subject not having EoE.

In embodiments directed to therapy of EoE, the methods of the present disclosure comprise treating subjects with elevated levels of EoE-associated markers. Examples of EoE-associated markers include, but are not limited to, for example, a molecule is selected from the group consisting of esophagus eosinophils, eotaxin-3, periostin, serum IgE, IL-13, IL-5, serum thymus and activation regulated chemokine (TARC), thymic stromal lymphopoietin (TSLP), serum eosinophilic cationic protein (ECP), and eosinophil-derived neurotoxin (EDN). Other relevant EoE-associated markers include, for example, a count of ≥15 eosinophils per high power field (HPF) in the esophagus, elevated peripheral eosinophil counts (>300 cells/µL) or elevated serum IgE (>150 kU/L), or a combination thereof. In one embodiment, the elevated level is a two-fold increase in marker expression as compared to a control level of the marker in a subject not having EoE. In one embodiment, the elevated level is a 3-fold, 4-fold, or 5-fold increase in marker expression as compared to a control level of the marker in a subject not having EoE.

In one embodiment, the subject or patient is an animal, preferably a mammal or a bird. Particularly preferably, the subject is selected from the group consisting of humans, dogs, cats, pigs, cows, buffalo and horses. Most preferably, the subject is a human subject.

In some embodiments, the methods herein may be used to treat eosinophilic disorder (e.g., EoE) in child subjects who are less than 3 years old. For example, the present methods may be used to treat infant subjects who are less than 1 month, 2 months, 3 months, 4 months, 5 months, 6 months, 7 months, 8 months, 9 months, 10 months, 11 months or less than 12 months old. In other embodiments, the methods of the present disclosure may be used to treat children who are more than 3 years old, more than 4 years, 5 years, 6 years, 7 years, 8 years, 9 years, 10 years, 11 years, 12 years, 13 years, 14 years, or more than 15 years old (including all ages in between).

In related embodiments, the methods herein may be used to treat EoE in adult subjects. By "adults," it is meant that the subject is at least 16 years old, which includes, a subject whose age is, for example, 16 years, 17 years, 18 years, 19 years, 20 years, 25 years, 30 years, 40 years, 50 years, 60 years, 70 years, 80 years, 90 years, or greater (including all ages in between).

In one embodiment, disclosed herein are methods for treating or ameliorating at least one symptom of eosinophilic disorders in a subject in need thereof, comprising first selecting a subject who exhibits at least one symptom associated with an eosinophilic disorder, and administering a therapeutically effective amount of an interleukin-13 antibody, or antigen-binding portion thereof, to the subject.

I. Selection of Subjects

In one embodiment, the method comprises first selecting a subject who has EoE. In one embodiment, the method comprises first selecting a subject who has been diagnosed with EoE. Particularly, the subject is a human subject who displays at least one symptom or indication associated with EGID. Especially, the subject is a human subject who displays at least one symptom or indication associated with an EGID that is selected from the group consisting of EoE, EG, ED, EI, EJ, and EC. The second step comprises administering a composition of the instant disclosure comprising an IL-13 antibody, or antigen-binding portion thereof.

In the context of the present embodiment, the selection step may be used to identify a subset of population which is more susceptible to the eosinophilic disorder. In these embodiments, the subject may display a particular trait or condition associated with the eosinophilic disorder. For example, "a subject in need thereof" may include a subject suffering from an atopic disease or disorder such as food allergy, atopic dermatitis, asthma, allergic rhinitis and allergic conjunctivitis. In certain embodiments, the term "a subject in need thereof" includes a subject who, prior to or at the time of therapy for eosinophilic disorder, has been or is diagnosed with atopic dermatitis, asthma, allergic rhinitis or allergic conjunctivitis. In other embodiments, the term "a subject in need thereof" may include a subset of subjects with inherited connective tissue disorders.

In other embodiments, the selection step may be used to identify a subset of population which is more likely to benefit from the therapy with the IL-13 antibody, or antigen-binding portion thereof. An example of such a subset of population is EoE patients who have previously undergone therapy with at least one steroid agent, but who are deemed unresponsive, refractory or as having relapsed from the therapy with the steroid agent.

In the therapeutic embodiments additionally including selection of a susceptible subject population, the methods may comprise implementing one or more reagents and/or tools for detecting disease-specific markers associated with EGID. For instance, EGID-associated markers may include protein markers such as elevated IgE levels or elevated eotaxin-3 levels. In other embodiments, the EGID-associated marker may include physiological markers, e.g., esophageal overexpression of pro-inflammatory mediators, enhanced level of eosinophilic infiltration of the mucosal lining, thickening of the epithelium, dysphagia, food impaction, chest and abdominal pain, or a combination thereof. A combination of the aforementioned markers, e.g., a biomarker and a physiological marker, may also be employed.

In the context of treating EoE-specific subjects, the methods of the present disclosure may involve first identifying a subset of subjects suffering from EoE based on detection of an EoE-specific marker. Examples of EoE-specific markers include biomarkers, e.g., protein markers, and physiological markers. For example, an EoE-specific biomarker may be a molecule is selected from the group consisting of esophagus eosinophils, eotaxin-3, periostin, serum IgE, IL-13, IL-5, serum thymus and activation regulated chemokine (TARC), thymic stromal lymphopoietin (TSLP), serum eosinophilic cationic protein (ECP), and eosinophil-derived neurotoxin (EDN). Examples of EoE-associated physiological markers include, for example, a count of ≥15 eosinophils per high power field (HPF) in the esophagus, elevated peripheral eosinophil counts (>300 cells/μL) or elevated serum IgE (>150 kU/L), or a combination thereof. A combination of the aforementioned markers, e.g., a biomarker and a physiological marker, may also be employed.

The selection step may involve, alternately or additionally, determination of eosinophilic infiltration, remodeling of GI tract, perforation, inflammation, obstruction of bowel movement, constipation, abdominal pain, weight loss and the like. With regard to EoE, the selection step may involve determining inflammation of the esophagus, thickening of the esophageal wall, appearance of trachea-like rings or ridges in the esophagus, chest and abdominal pain, food refusal, vomiting, dysphagia and food impaction. A positive identification may involve presence of at least 1, at least 2, at least 3 or more of the aforementioned markers.

Particularly, the subjects that are selected for treatment in accordance with the instant disclosure include subjects who display at least one of the aforementioned traits, e.g., food allergy, atopic dermatitis, asthma, allergic rhinitis and allergic conjunctivitis and who also test positive for an EGID-associated biomarker, e.g., IgE, eotaxin-3, periostin, IL-5, or IL-13.

In related embodiments, "a subject in need thereof" includes a subject susceptible to an allergen. For example, "a subject in need thereof" includes a subject who may exhibit one of the following characteristics: (a) is prone to allergic reactions or responses when exposed to one or more allergens; (b) has previously exhibited an allergic response or reaction to one or more allergens; (c) has a known history of allergies; and/or (d) exhibits a sign or symptom of an allergic response or anaphylaxis. In certain embodiments, the subject is allergic to an allergen associated with EGID or that renders the subject susceptible or prone to developing EGID. Particularly, the subject is allergic to an allergen associated with EOE or that renders the subject susceptible or prone to developing EOE.

The term "allergen," as used herein, includes any substance, chemical, particle or composition which is capable of stimulating an allergic response in a susceptible individual. Allergens may be contained within or derived from a food item such as, e.g., dairy products (e.g., cow's milk), egg, wheat, soy, corn, rye, fish, shellfish, peanuts and tree nuts. Alternatively, an allergen may be contained within or derived from a non-food item such as, e.g., dust (e.g., containing dust mite), pollen, insect venom (e.g., venom of bees, wasps, mosquitoes, etc.), mold, animal dander, latex, medication, drugs, ragweed, grass and birch.

In certain embodiments, the term "a subject in need thereof" includes a subset of population which exhibits an allergic reaction to a food allergen. For example, "a subject in need thereof" may include a subject who has an allergy to an allergen contained in a food item including, but not limited to, a dairy product, egg, wheat, soy, corn, rye, fish, shellfish, peanut, a tree nut, beef, chicken, oat, barley, pork, green beans, and fruits such as apple and pineapple.

In certain embodiments, the term includes a subject allergic to a non-food allergen such as allergens derived from dust, mold, insects, plants including pollen, and pets such as cats and dogs. Examples of non-food allergens (also known as environmental allergens or aeroallergens) include, but are not limited to, house dust mite allergens, pollen allergens, animal dander allergens, insect venom, grass allergens, and latex.

As used herein, the phrases "allergic response," "allergic reaction," "allergic symptom," and the like, include one or more signs or symptoms selected from the group consisting of urticaria (e.g., hives), angioedema, rhinitis, asthma, vomiting, sneezing, runny nose, sinus inflammation, watery eyes, wheezing, bronchospasm, reduced peak expiratory flow (PEF), gastrointestinal distress, flushing, swollen lips, swollen tongue, reduced blood pressure, anaphylaxis, and organ dysfunction/failure. An "allergic response," "allergic reaction," "allergic symptom," etc., also includes immunological responses and reactions such as, e.g., increased IgE production, increased allergen-specific immunoglobulin production and/or eosinophilia.

Embodiments of the disclosure is directed to treatment of treatment-naïve as well as previously-treated subjects. The subjects may include responders, non-responders, refractory or relapsed subjects.

The term "treatment-naïve" is meant to include subjects who have never been actively treated for any eosinophilic disorder. Existing modes of therapy of EGIDs include, e.g., dietary therapy (i.e., staying away from particular foods), mechanical intervention (e.g., dilation of the esophagus, colon, or small intestines, including surgery) or pharmacological therapy (i.e., use of pharmaceutical agents).

Particularly, under this embodiment, there is provided a method for treating subjects suffering from eosinophilic disorders who have previously undergone pharmacological therapy. In the context of EGID, pharmacological therapy may include, for instance, use of acid suspending agents such as proton pump inhibitors, treatment with glucocorticoids such as fluticasone, budesonide, and ciclesonide, use of prostaglandin D2 receptor antagonists such as Ser. No. 00/000,459, systemic or local use of antihistamines and/or mast cell stabilizers such as cromolyn, and therapy with antibodies such as mepolizumab, reslizumab, omalizumab, infliximab or experimental agents such as MONTELU-KAST. Especially, under this embodiment, the subject is non-responsive to or has relapsed from therapy with the one or more of the aforementioned pharmacological agents.

Accordingly, embodiments of the disclosure relate to methods for treating, reducing the incidence of, preventing, or ameliorating at least one symptom or indication of EGID in a subject who has previously undergone therapy for the EGID and who is deemed non-responsive to or have refracted or relapsed from the EGID therapy, comprising administering a therapeutically effective amount of an interleukin-13 antibody, or antigen-binding portion thereof, to the subject. The subject is preferably a human subject who displays at least one symptom or indication associated with EoE, EG, ED, EI, EJ, or EC. Particularly, in these embodiments, the subject has relapsed from or is refractory to steroid therapy, e.g., therapy with fluticasone, budesonide, and ciclesonide, including related molecules, e.g., tautomers, analogs, derivatives of the aforementioned steroid agents. Representative examples of congeners of fluticasone, budesonide, and ciclesonide, and the like are known, e.g., via the PUBCHEM compound database.

Methods for identifying refractory subjects are known in the art. For example, subjects who do not have a meaningful clinical response to glucocorticoids up to 20 to 80 mg/day (particularly between 40 to 60 mg/day) within 30 days for oral therapy or 7 to 10 days for IV therapy are considered to be steroid-refractory. Meaningful clinical response of the steroid agent in treating eosinophilic disorders may be determined pathologically, histologically, or clinically. Such methods may involve laboratory studies, endoscopic analysis, stool analysis, imaging studies (e.g., via computed tomography (CT) enterography, magnetic resonance (MR) enterography, or dedicated small bowel series) or the like.

2. Determination of Treatment Efficacy

According to other aspects of the disclosure, methods for treating EoE are tied to determination of effectiveness of treatment. Under this embodiment, the subject is administered a composition comprising a therapeutically effective amount of an IL-13 antagonist and a change in the EoE-associated marker is monitored before and/or after therapy. The therapy is deemed effective if at least one EoE-associated marker (e.g., esophagus eosinophil count, eotaxin-3, IgE, etc.) is reduced at a time after administration of the composition, as compared to the level of the marker in the subject prior to the administration. Under this embodiment, a reduction of at least 40%, at least 50%, at least 60%, at least 70%, at least 80%, at least 90%, at least 95% or more in the level of the marker after treatment with the composition containing the IL-13 antibody, or antigen-binding portion thereof, compared to the level of the marker before treatment with the composition (or treatment with a placebo) signifies that the treatment is effective.

In one embodiment, the methods of the present disclosure comprise determining an EoE-associated parameter selected from: (a) dysphagia clinical symptom frequency/severity as assessed by a daily symptom diary (DSD) score; (b) peak esophageal eosinophil count (cells/hpf); (c) mean EEsAI PRO scores; (d) subject's global assessment of disease severity; (e) clinician's global assessment of disease severity; and (f) number and/or severity of treatment-associated adverse events (TEAE), each of which are described in more detail below.

In one embodiment, the mean esophageal eosinophil count is determined in a subject both before and after treatment with the antibody, or antigen-binding portion thereof, in order to determine response to treatment. Eosinophil count may be assessed using any methods known to one of skill in the art, for example, but not limited to histology, flow cytometry. See, US patent app. pub. Nos. 2013/0096096 and 2009/0181099 and Rodrigo et al. (*The American Journal of Gastroenterology* 103, 435-442 (2008)), the disclosures in which are incorporated by reference herein. In one embodiment, a mean esophageal eosinophil count is measured from at least one, at least two, at least 3, at least 4, at least 5, at least 6, at least 7, at least 8, at least 9, at least 10, at least 15, at least 20, at least 25, at least 30, or more inflamed high powered fields in the esophagus. In one embodiment, the eosinophil count may be measured by any one of the commercially available kits.

In one embodiment, the mean esophageal eosinophil count in at least 5 inflamed high powered fields (HPF) in the esophagus is determined in a subject, before treatment with the antibody, or antigen-binding portion thereof. In one embodiment, a count of >15 cells/HPF indicates that the subject has EoE. Typically, the mean esophageal eosinophil count in EoE subjects is between 50-200 cells/HPF, between 80-150 cells/HPF, and especially between 90-125 cells/HPF. In a related embodiment, a count between 15-40 cells/HPF indicates mild grade/severity of EoE, a count between 41-80 cells/HPF indicates moderate grade/severity of EoE, and a count >80 cells/HPF indicates high grade/severity of EoE.

In one embodiment, the mean esophageal eosinophil count in at least 5 inflamed high powered fields (HPF) in the esophagus is determined in a subject, both before treatment (baseline) and after treatment (post-treatment) with the antibody, or antigen-binding portion thereof, in order to determine response to treatment. In one embodiment, a reduction in the mean esophageal eosinophil count in the post-treatment level compared to the pre-treatment level is indicative of the efficacy of treatment. In these embodiments, the baseline mean esophageal eosinophil count in EoE subjects is between 50-200 cells/HPF, between 80-150 cells/HPF, or preferably between 90-125 cells/HPF. In one embodiment, a post-treatment mean esophageal eosinophil count of between 0-85 cells/HPF, preferably between 10-60 cells/HPF and especially preferably between 15-40 cells/HPF, is indicative of a response to treatment.

In one embodiment, the peak esophageal eosinophil count in at least 5 inflamed high powered fields (HPF) in the esophagus is determined in a subject, both before administration of the antibody, or antigen-binding portion thereof (baseline), and after administration (post-treatment), wherein a reduction in the peak esophageal eosinophil count post-treatment compared to the baseline is indicative of the efficacy of treatment. In one embodiment, the baseline peak esophageal eosinophil count in EoE subjects is between 18-389 cells/HPF, between 40-160 cells/HPF, or between 70-140 cells/HPF. In one embodiment, a post-treatment peak esophageal eosinophil count of between 0-157 cells/HPF, preferably between 10-70 cells/HPF and especially preferably between 14-40 cells/HPF, is indicative of a response to treatment.

In another embodiment, scoring of dysphagia clinical symptoms in a subject both before administration of the antibody, or antigen-binding portion thereof (baseline), and after administration (post-treatment), is performed, wherein a reduction in the dysphagia clinical symptoms post-treatment compared to the baseline is indicative of the efficacy of treatment. Dysphagia clinical symptoms include, for example, having pain while swallowing (odynophagia) being unable to swallow, having the sensation of food getting stuck in the throat or chest or behind the breastbone (sternum), drooling, regurgitation, frequent heartburns, acid reflux, unexpected weight loss, coughing or gagging when swallowing, hoarse/inaudible speech, etc. Dysphagia clinical symptoms may be assessed using any methods known to one of skill in the art. See, Cheung et al. (*J. Pediatr. Gastroenterol. Nutr.*, 37:498-503 (2003)) and Furata et al. (*Gastroenterology;* 133:1342-1363 (2007)), the disclosures in which are incorporated by reference herein. In one embodiment, the dysphagia clinical symptoms are assessed by a patient's dysphagia symptom questionnaire (DSQ) score. Methods of determining DSQ scores are known in the art. See, e.g., US patent app. pub. No. 2016/0078186 and Delton et al. (*Aliment Pharmacol Ther.*, 38(6):634-642 (2013)), the disclosures in which are incorporated by reference herein. A representative method for determining DSQ is provided below in the Examples section.

In another embodiment, scoring of a mean dysphagia symptom composite diary score in a subject both before administration of the antibody, or antigen-binding portion thereof (baseline), and after administration (post-treatment), is performed, wherein a reduction in the mean dysphagia symptom composite diary score post-treatment compared to the baseline is indicative of the efficacy of treatment. In one embodiment, a mean dysphagia symptom composite diary score of >5 indicates that the subject has EoE. In one embodiment, the mean dysphagia symptom composite diary score in EoE subjects prior to treatment is between 5-50, between 19-40, or between 25-35. In one embodiment, a baseline score of between 5-15 indicates mild grade/severity EoE, a score between 16-25 indicates moderate grade/severity EoE, and a score >25 indicates high grade/severity EoE. In one embodiment, a post-treatment score of between 0 and 40, preferably between 6 and 32 and especially preferably between 10 and 20, is indicative of an effective treatment. In subjects having EoE who are steroid refractory, the baseline score may be between 5-50, between 19-40, or 25-35; and a post-treatment score of between 0-40, preferably between 10-24, and especially preferably between 14-18, is indicative of response to treatment.

In another embodiment, scoring of eosinophilic esophagitis activity index (EEsAI or EoEAI) may be measured both pre-treatment and post-treatment. EEsAI may be assessed using any methods known to one of skill in the art. See, US patent pub. No. 2015/0017176 and Schoepfer et al. (*Gastroenterology*, 147(6):1255-66 (2014)). See also the review article by Schoepfer et al. (*Digestive Diseases, Vol.* 32, No. 1-2 (2014)), which describes a multi-parametric approach to determining EEsAI, involving, determination of (a) symptoms, (b) quality of life, (c) endoscopy, (d) histology, (e) blood markers, and (f) technological assessment, e.g., ENDOFLIP. A similar technique is exemplified below in the Examples section.

In one embodiment, a baseline score of >10 indicates that the subject has EoE. Typically, the EEsAI in EoE subjects is between 5-100, between 30-90, or between 40-70. In one embodiment, an EEsAI score of between 0-20 indicates mild grade/severity EoE, a score between 21-40 indicates moderate grade/severity EoE, and a score >41 indicates high grade/severity EoE.

In another embodiment, determining the EEsAI in a subject both before administration of the antibody, or antigen-binding portion thereof (baseline), and after administration (post-treatment), is performed, wherein a reduction in the EEsAI post-treatment compared to the baseline is indicative of the efficacy of treatment. In these embodiments, a post-treatment level of between 5 and 90, preferably between 10 and 60, and especially preferably between 20 and 40 is indicative of a response to treatment. In EoE subjects who are steroid refractory, the baseline level is between 5-100, between 30-90, or preferably between 40-70, and a post-treatment level of between 5 and 90, preferably between 20 and 50 and especially preferably between 30 and 40, is indicative of response to treatment. Generally, a decrease in EEsAI below 40 indicates significantly effective treatment.

In another embodiment, the endoscopic reference score (EREFS) is determined. EREF score may be assessed using any methods known to one of skill in the art, for example, but not limited to measurement of inflammatory and remodeling esophageal features. See, US patent pub. No. 2015/0017176 and van Rhijn et al. (*Endoscopy* 46(12):1049-55 (2014)). A representative method for the measurement of EREF score is provided below in the Examples section. A baseline EREF score in EoE subjects is between 4-10, between 5-10, or between 7-9. In one embodiment, an EREF score of between 0-4 indicates mild grade/severity EoE, a score between 4-7 indicates moderate grade/severity EoE, and a score >7 indicates high grade/severity EoE.

In another embodiment, determining the EREF in a subject both before administration of the antibody, or antigen-binding portion thereof (baseline), and after administration (post-treatment), is performed, wherein a reduction in the EREF post-treatment compared to the baseline is indicative of the efficacy of treatment. In these embodiments, the baseline level is between 4-10, between 5-10, or preferably >9. In one embodiment, a post-treatment level of between 3 and 8, preferably between 4 and 7 and especially preferably <5.5 is indicative of a response to treatment.

In one embodiment, the baseline level of inflammation-specific EREF is between 4-8, between 5-8, or >5. In another embodiment, a post-treatment level of inflammation-specific EREF between 1 and 6, preferably between 2 and 5, and especially preferably <3.0, is indicative of a response to treatment. In another embodiment, the baseline level of remodeling-specific EREF is between 2-5, between 3-4, or >2.5. In one embodiment, a post-treatment level of inflammation-specific EREF between 2 and 4, preferably between 2.2 and 3.1, and especially preferably <3.0 is indicative of a response to treatment.

In another embodiment, a subject's global assessment of disease severity is determined.

In another embodiment, a clinician's global assessment of disease severity is determined. In yet another embodiment, a combination of subject's global assessment of disease severity and a clinician's global assessment of disease severity is determined. Global assessments of EoE disease therapy are well known in the art. For example, Schoepfer et al. (*The American Journal of Gastroenterology* 110, 402-414 (2015)) describe a method involving assessments by gastroenterologists (PhysGA), which involved analysis of biopsy samples after esophagogastroduodenoscopy, with scores being issued on Likert scale ranging from 0 to 10 based on patient history and endoscopic and histologic findings. A second global assessment of EoE symptom severity by patients (PatGA) was performed in parallel, which was also scored on a Likert scale ranging from 0 (inactive) to 10 (most active). Linear regression and analysis of variance was used to quantify the extent to which variations in severity of EoE symptoms and endoscopic and histologic findings attributed to the overall assessment, which was reported as individual scores. A similar technique is exemplified below in the Examples section.

In another embodiment, determining the subject's assessment of disease severity is determined in a subject both before administration of the antibody, or antigen-binding portion thereof (baseline), and after administration (post-treatment), is performed, wherein a reduction in the subject's assessment of disease severity compared to the baseline is indicative of the efficacy of treatment. In one embodiment, a baseline score of >1 indicates that the subject has EoE. In one embodiment, a baseline score of between 2-9, between 3-8, or >5 indicates that the subject has EoE. In one embodiment, a subject's score of between 1-3 indicates mild grade/severity EoE, a score between 4-7 indicates moderate grade/severity EoE, and a score >7 indicates high grade/severity EoE. In one embodiment, a post-treatment level of between 0 and 9, preferably between 2 and 6, and especially preferably <3 indicates a response to treatment.

In another embodiment, determining the clinician's assessment of disease severity is determined in a subject both before administration of the antibody, or antigen-binding portion thereof (baseline), and after administration (post-treatment), is performed, wherein a reduction in the clinician's assessment of disease severity compared to the baseline is indicative of the efficacy of treatment. In one embodiment, a clinician's score of >2 indicates that the subject has EoE. In one embodiment, the baseline clinician's score in EoE subjects is between 3-10, between 3-9, or >6. In one embodiment, a clinician's score of between 1-3 indicates mild grade/severity EoE, a score between 4-7 indicates moderate grade/severity EoE, and a score >7 indicates high grade/severity EoE. In one embodiment, a post-treatment level of between 0 and 8, preferably between 2 and 6, and especially preferably <3.3 is indicative of a response to treatment.

In related embodiments, a composite (composite score) of a subject's score and a clinician's score before administration of the composition (baseline level) and after administration of the composition (post-treatment level) is determined, wherein a reduction in the composite score post-treatment compared to the baseline is indicative of the efficacy of treatment. In one embodiment, a baseline composite score is between 2-20, between 6-18, or >11. In another embodiment, a post-treatment level of between 0 and 17, preferably between 4 and 12, and preferably <6.3, is indicative of an efficacious response to treatment.

As will be appreciated by a person of ordinary skill in the art, an increase or decrease in an EoE-associated biomarker can be determined by comparing (i) the level of the biomarker measured in a subject at a defined time point after administration of the composition comprising an IL-13 antibody, or antigen-binding portion thereof, to (ii) the level of the biomarker measured in the patient prior to the administration of the composition comprising an IL-13 antibody, or antigen-binding portion thereof (i.e., the "baseline measurement"). The defined time point at which the biomarker is measured can be, e.g., at about 4 hours, 8 hours, 12 hours, 1 day, 2 days, 3 days, 4 days, 5 days, 6 days, 7 days, 8 days, 9 days, 10 days, 15 days, 20 days, 35 days, 40 days, 50 days, 55 days, 60 days, 65 days, 70 days, 75 days, 80 days, 85 days, or more, after administration of the of the composition comprising an IL-13 antibody, or antigen-binding portion thereof.

According to certain embodiments of the present disclosure, a subject may exhibit a decrease in the level of one or more of IgE and/or eotaxin-3 following administration of a composition comprising an IL-13 antibody, or antigen-binding portion thereof. For example, at about day 1, day 4, day 8, day 15, day 22, day 25, day 29, day 36, day 43, day 50, day 57, day 64, day 71 or day 85, following administration of a first, second, third or fourth dose of a composition comprising about 75 mg to about 600 mg of an anti-IL-13 antibody (e.g., RPC4046), the subject, according to the present disclosure, may exhibit a decrease in eotaxin-3 of about 1%, 2%, 5%, 10%, 15%, 20%, 25%, 30%, 35%, 40%, 45%, 50%, 55%, 60%, 65%, 70%, 75%, 80%, 85%, 90%, 95% or more from baseline (wherein "baseline" is defined as the level of eotaxin-3 in the subject just prior to the first administration). Similarly, at about day 1, day 4, day 8, day 15, day 22, day 25, day 29, day 36, day 43, day 50, day 57, day 64, day 71 or day 85, following administration of a first, second, third or fourth dose of a composition comprising about 75 mg to about 600 mg of an anti-IL-13 antibody (e.g., RPC4046), the subject, according to the present disclosure, may exhibit a decrease in IgE of about 1%, 2%, 5%, 10%, 15%, 20%, 25%, 30%, 35%, 40%, 45%, 50%, 55%, 60%, 65%, 70%, 75%, 80%, 85%, 90%, 95% or more from baseline (wherein "baseline" is defined as the level of IgE in the subject just prior to the first administration).

The present disclosure also includes methods for determining whether a subject is suitable for the therapy with a composition comprising an IL-13 antibody, or antigen-binding portion thereof. For example, if an individual, prior to receiving a composition comprising an IL-13 antibody, or antigen-binding portion thereof, exhibits a level of an EoE-associated biomarker which signifies the disease state, the individual is therefore identified as a suitable patient for whom administration of a composition of the disclosure (a composition comprising an anti-IL-13 antibody) would be beneficial. In related embodiments, the present disclosure includes methods for treating suitable subjects, wherein a suitable subject may be more susceptible to EoE, for example, due to food allergy, or an atopic disease. For example, the present disclosure includes methods comprising administering an IL-13 antibody, or antigen-binding portion thereof, to subjects who have food allergy, atopic dermatitis, asthma, allergic rhinitis or allergic conjunctivitis. In another example, the present disclosure includes methods comprising administering an IL-13 antibody, or antigen-binding portion thereof, to subjects who have, Mendelian-inherited connective tissue disorders, e.g., Marfan syndrome, Loeys-Dietz syndrome, hypermobile Ehlers Danlos syndrome (EDS) or joint hypermobility syndrome (JHS). Such subject populations may have an elevated level of an EoE-associated biomarker.

According to certain exemplary embodiments, an individual may be identified as a good candidate for anti-IL-13 therapy if the individual exhibits one or more of the following: (i) an eotaxin-3 level greater than about 30 pg/ml, greater than about 40 pg/ml, greater than about 50 pg/ml, greater than about 100 pg/ml, greater than about 1500 pg/ml, greater than about 200 pg/ml, greater than about 250 pg/ml, greater than about 300 pg/ml, greater than about 350 pg/ml, greater than about 400 pg/ml, greater than about 450 pg/ml, or greater than about 500 pg/ml; or (ii) a serum IgE level greater than about 114 kU/L, greater than about 150 kU/L, greater than about 500 kU/L, greater than about 1000 kU/L, greater than about 1500 kU/L, greater than about 2000 kU/L, greater than about 2500 kU/L, greater than about 3000 kU/L, greater than about 3500 kU/L, greater than about 4000 kU/L, greater than about 4500 kU/L, or greater than about 5000 kU/L; or (iii) 15 eosinophils per high power field in the esophagus of the subject. Additional criteria, such as other clinical indicators of EoE (e.g., thickening of the esophageal wall, and food allergy indicative of EoE), may be used in combination with any of the foregoing EoE-associated biomarkers to identify an individual as a suitable candidate for anti-IL-13 therapy as described elsewhere herein.

In other embodiments, the diagnostic methods may be aided by the power of gene expression assays. Chips used in gene expression analysis and markers that are specific to EGIDs are known in the art, e.g., US patent pub. Nos. 2015/0045334 and 2014/0286896, the contents of which are incorporated by reference herein in their entirety.

As used herein, "eosinophilic infiltration" refers to the presence of eosinophils in an organ or tissue including blood, esophagus, stomach, duodenum, ileum, colon of a subject. In the context of the disclosure, the term "eosinophilic infiltration" refers to presence of eosinophils in the mucosal lining of a region of the gastro-intestinal tract including, but not limited to, esophagus, stomach, ileum, duodenum, colon, etc. Eosinophilic infiltration may be analyzed, for example, in a tissue biopsy of a subject suffering from the eosinophilic disorder. Particularly, the diagnosis is made from a tissue biopsy of a subject suffering from an EGID selected from the group consisting of EoE, EG, ED, EJ, EI and EC. The tissues that are useful in the biopsy include, for example, esophagus, gut, duodenum, jejunum, ileum, colon, or a combination thereof. Other tissue samples, e.g., organs and linings of the GI tract, may also be optionally and/or additionally employed.

According to particular embodiments, "eosinophilic infiltration" refers to the presence of ≥15 eosinophils per high power field (HPF) in the esophagus. The term "high power field" refers to a standard total magnification of 200-times (or greater) by a microscope used to view eosinophils in a tissue, e.g., from the esophagus of a subject. Particularly, HPF refers to standard total magnification of 400-times by a microscope.

In certain embodiments, "eosinophilic infiltration" includes infiltration into a tissue by leucocytes, for example, lymphocytes, neutrophils and mast cells. The leucocyte infiltration into, e.g., esophageal tissue can be detected by cell surface markers such as eosinophil-specific markers (e.g., CD11cLow/Neg, SiglecF+, F4/80+, EMR1+, Siglec 8+, and MBP2+), macrophage-specific markers (e.g., CD11b+, F4/80+, CD14+, EMR1+, and CD68+), neutrophil-specific markers (e.g., CD11b+, Ly6G+, Ly6C+, CD11b+, and CD66b+), and T-cell-specific markers (e.g., CD3+CD4+CD8+).

As used herein, a reduction in eosinophils means that the number of eosinophils and other leucocytes measured in the particular tissue/site of interest, e.g., esophagus, gut, duodenum, jejunum, ileum, and/or colon of a subject with EGID, is reduced in treated subjects compared to the same or equivalent subject who has not been treated with an IL-13 inhibitor, e.g., IL-13 antibody, or antigen-binding portion thereof. In these embodiments, treatment with the compositions of the instant disclosure results in a net reduction in the number of eosinophils and/or leucocytes in the tissue/situs of at least 5%, at least 10%, at least 20%, at least 50%, at least 70%, at least 80%, at least 90%, or at least 99% compared to that of the untreated subjects.

Particularly, wherein the EGID is EoE, treatment with the compositions of the instant disclosure results in a net reduction in the number of eosinophils and/or leucocytes in the esophagus of at least 5%, at least 10%, at least 20%, at least 50%, at least 70%, at least 80%, at least 90%, or at least 99% compared to that of the untreated subjects.

In certain embodiments, reducing eosinophilic infiltration means detecting fewer than 50 eosinophils per high power field, particularly fewer than 30 eosinophils, fewer than 20 eosinophils, fewer than 15 eosinophils, fewer than 10 eosinophils, fewer than 8 eosinophils, or fewer than 6 eosinophils per high power field (HPF) in a biopsy of the tissue/site of interest. In embodiments related to therapy of EGID, reducing eosinophilic infiltration means detecting fewer than 15 eosinophils, fewer than 12 eosinophils, fewer than 10 eosinophils, fewer than 8, or fewer than 6 eosinophils per HPF in a biopsy of the GI tissue, e.g., epithelial mucosa lining the esophagus. In certain embodiments, a reduction in eosinophilic infiltration means that no eosinophils are detected in the esophageal mucosa of a subject.

In one embodiment, a subject who has been treated with the IL-13 antibody, or antigen-binding portion thereof, is assessed at various time points using a plurality of specific and global markers. The specific marker may be a biomarker or a physiological marker described previously. As described in detail in the Examples section, a modulation in the mean and/or peak levels of the marker between baseline (t=0) and the time-point of interest (t=ti) allows for the prognostication and recommendation for follow up. For example, the prognosis of therapy may be described as good or favorable depending on the reduction of EoE-specific markers. Under this scenario, based on an observed level of reduction of at least 30%, at least 40%, at least 50%, at least 60%, at least 70%, at least 80%, at least 90%, at least 95% or more in the level of the marker after treatment, the subject would be recommended to continue therapy with the therapeutic agent.

Additionally, related embodiments of the disclosure provide methods for monitoring of subjects undergoing therapy for eosinophilic disorders comprising determining a parameter before and after therapy. More specifically, the eosinophilic disorder is an EGID selected from EoE, EG, EJ, EI, ED, and EC. Representative examples of such parameters include reduction in the aforementioned physiological markers or biomarkers of EGID. In other embodiments, the parameter is selected from a subject's global assessment of disease severity; a clinician's global assessment of disease severity; a subject's global impression (e.g., based on wellness scoring); histology grades and stage-adjusted scores of the disease; number and severity of treatment-emergent adverse events (TEAE) (collectively termed "macroscopic assessments").

In the aforementioned embodiments relating to monitoring of therapy of EGID (e.g., EoE) based on macroscopic assessments, a post-treatment reduction of at least 30%, at least 40%, at least 50%, at least 60%, at least 70%, at least 80%, at least 90%, at least 95% or more in the subject's/clinician's assessment of disease severity, histology/stage scores, or TEAE numbers compared to pre-treatment levels is indicative of effective therapy. Likewise, a post-treatment increase of at least 30%, least 40%, at least 50%, at least 60%, at least 70%, at least 80%, at least 90%, at least 1-fold, at least 1.2-fold, at least 1.5-fold, at least 1.8-fold, at least 2.0-fold, at least 2.5-fold, at least 3.0-fold or more in the betterment and/or wellness scores compared those obtained prior to treatment is indicative of effective therapy.

B. Asthma

Asthma is a chronic inflammatory disorder of the airways characterized by wheezing, breathlessness, chest tightness, and cough. Asthma affects approximately 20 million people in the US, and about 75% of asthma patients are adults. Of the adult asthma patients, approximately 60% of asthma patients have mild disease, about 20% have moderate disease and the remaining 20% have severe disease.

Interleukin-13 (IL-13) is thought to be pivotal in the pathogenesis of human asthma, in that elevated levels of IL-13 are present in the lungs of asthma patients, and these levels correlate with disease severity. Likewise, increased IL-13 is present in both sputum and in lung biopsies of patients with moderate to severe asthma who are treated with inhaled corticosteroids (ICS) or systemic corticosteroids and continue to be symptomatic. Moreover, human IL-13 genetic polymorphisms are associated with asthma and atopy (allergic hypersensitivity). IL-13 binds to two receptors, IL 13Rα1 and IL 13Rα2. IL 13 is a well-validated target for asthma as efficacy has been demonstrated using various means of IL-13 antagonism in multiple, pre-clinical models of asthma.

Examples of asthma that are treatable in accordance with the present invention include, but are not limited to, allergic and non-allergic asthma (e.g., asthma due to infection with, e.g., respiratory syncytial virus (RSV), e.g., in younger children)), chronic obstructive pulmonary disease (COPD), and other conditions involving airway inflammation, eosinophilia, fibrosis and excess mucus production, e.g., cystic fibrosis and pulmonary fibrosis.

In other embodiments, this application provides a method of treating (e.g., reducing, ameliorating) or preventing one or more symptoms associated with a respiratory disorder, e.g., asthma (e.g., allergic and nonallergic asthma); allergies; chronic obstructive pulmonary disease (COPD); a condition involving airway inflammation, eosinophilia, fibrosis and excess mucus production, e.g., cystic fibrosis and pulmonary fibrosis. For example, symptoms of asthma include, but are not limited to, wheezing, shortness of breath, bronchoconstriction, airway hyperreactivity, decreased lung capacity, fibrosis, airway inflammation, and mucus production. The method comprises administering to the subject an IL-13 antagonist, e.g., an IL-13 antibody or a fragment thereof, in an amount sufficient to treat (e.g., reduce, ameliorate) or prevent one or more symptoms. The IL-13 antibody can be administered therapeutically or prophylactically, or both. The IL-13 antagonist, e.g., the anti-IL-13 antibody, or antigen-binding portion thereof, can be administered to the subject, alone or in combination with other therapeutic modalities as described herein. Preferably, the subject is a mammal, e.g., a human suffering from an IL-13-associated disorder, such as asthma, as described herein.

In accordance with the foregoing, embodiments of the instant invention relate to treatment of patients with asthma comprising administering to a subject in need thereof, an IL-13 antibody or an antigen-binding fragment thereof, including, compositions containing such antibodies. It is contemplated that the dosages and the types of compositions that are found effective for the treatment of EoE are also effective in treating asthma.

Furthermore, embodiments of the instant invention relate to methods for evaluating the efficacy of such anti-IL-13 antibodies or antigen-binding fragments thereof, in reducing the severity or grade of asthma in subjects. It is contemplated that the methods and assays that are effective in evaluating the efficacy of treatment of EoE are also applicable for determining the efficacy of such agents in treating asthma.

Antibodies of the invention, or antigen binding portions thereof can be used alone or in combination to treat such diseases. It should be understood that the antibodies of the invention or antigen binding portion thereof can be used alone or in combination with an additional agent, e.g., a therapeutic agent, said additional agent being selected by the skilled artisan for its intended purpose. For example, the additional agent can be a therapeutic agent art-recognized as being useful to treat the disease or condition being treated by the antibody of the present invention. The additional agent also can be an agent that imparts a beneficial attribute to the therapeutic composition e.g., an agent which effects the viscosity of the composition.

It should further be understood that the combinations which are to be included within this invention are those combinations useful for their intended purpose. The agents set forth below are illustrative for purposes and not intended to be limited. The combinations, which are part of this invention, can be the antibodies of the present invention and at least one additional agent selected from the lists below. The combination can also include more than one additional agent, e.g., two or three additional agents if the combination is such that the formed composition can perform its intended function.

The combination therapy can include one or more IL-13 inhibitors, e.g., anti-IL-13 antibodies or fragments thereof, coformulated with, and/or coadministered with, one or more additional therapeutic agents, e.g., one or more cytokine and growth factor inhibitors, immunosuppressants, anti-inflammatory agents (e.g., systemic anti-inflammatory agents), anti-fibrotic agents, metabolic inhibitors, enzyme inhibitors, and/or cytotoxic or cytostatic agents, as described in more herein.

Examples of preferred additional therapeutic agents that can be coadministered and/or coformulated with one or more IL-13 antagonists, e.g., anti-IL-13 antibodies or fragments thereof, include, but are not limited to, one or more of: inhaled steroids; beta-agonists, e.g., short-acting or long-acting beta-agonists; antagonists of leukotrienes or leukotriene receptors; combination drugs such as ADVAIR; IgE inhibitors, e.g., anti-IgE antibodies (e.g., XOLAIR); phosphodiesterase inhibitors (e.g., PDE4 inhibitors); xanthines; anticholinergic drugs; mast cell-stabilizing agents such as cromolyn; IL-4 inhibitors; IL-5 inhibitors; eotaxin/CCR3 inhibitors; antagonists of histamine or its receptors including H1, H2, H3, and H4, and antagonists of prostaglandin D or its receptors (DP1 and CRTH2). Such combinations can be used to treat asthma and other respiratory disorders. Additional examples of therapeutic agents that can be coadministered and/or coformulated with one or more anti-IL-13 antibodies or fragments thereof include one or more of: TNF antagonists (e.g., a soluble fragment of a TNF receptor, e.g., p55 or p75 human TNF receptor or derivatives thereof, e.g., 75 kD TNFR-IgG (75 kD TNF receptor-IgG fusion protein, ENBREL)); TNF enzyme antagonists, e.g., TNF converting enzyme (TACE) inhibitors; muscarinic receptor antagonists; TGF-beta antagonists; interferon gamma; perfenidone; chemotherapeutic agents, e.g., methotrexate, leflunomide, or a sirolimus (rapamycin) or an analog thereof, e.g., CCI-779; COX2 and cPLA2 inhibitors; NSAIDs; immunomodulators; p38 inhibitors, TPL-2, MK-2 and NFkB inhibitors, among others.

Other preferred combinations are cytokine suppressive anti-inflammatory drug(s) (CSAIDs); antibodies to or antagonists of other human cytokines or growth factors, for example, IL-1, IL-2, IL-3, IL-4, IL-5, IL-6, IL-7, IL-8, IL-15, IL-16, IL-18, IL-21, IL-31, interferons, EMAP-II, GM-CSF, FGF, EGF, PDGF, and edothelin-1, as well as the receptors of these cytokines and growth factors. Antibodies of the invention, or antigen binding portions thereof, can be combined with antibodies to cell surface molecules such as CD2, CD3, CD4, CD8, CD25, CD28, CD30, CD40, CD45, CD69, CD80 (B7.1), CD86 (B7.2), CD90, CTLA or their ligands including CD154 (gp39 or CD40L).

Preferred combinations of therapeutic agents may interfere at different points in the inflammatory cascade; preferred examples include TNF antagonists like chimeric, humanized or human TNF antibodies, D2E7, (PCT Publication No. WO 97/29131), CA2 (Remicade™), CDP 571, and soluble p55 or p75 TNF receptors, derivatives, thereof, (p75TNFR1gG (Enbrel™) or p55TNFR1gG (Lenercept), and also TNF converting enzyme (TACE) inhibitors; similarly IL-1 inhibitors (Interleukin-1-converting enzyme inhibitors, IL-1RA etc.) may be effective for the same reason. Other preferred combinations include Interleukin 4. Yet another preferred combination are other key players of the asthmatic response which may act parallel to, dependent on or in concert with IL-13 function; especially preferred are IL-9 antagonists including IL-9 antibodies. It has been shown that IL-13 and IL-9 have overlapping but distinct functions and a combination of antagonists to both may be most effective. Yet another preferred combination are anti-IL-5 antibodies. Yet other preferred combinations include antagonists of chemokines including MCP-1, MCP-4, eotaxins, RANTES, MDC, CCL-12 and CCL-17 (TARC) and chemokine receptors including CCR2, CCR3, CCR4, and CXCR4. Yet combinations can include antagonists to asthma mediators including acid mammalian chitinase, CRHT2, chymase, S1P1, S1P2, Tyk2, ROCKII, Stat6, p38, NFkB, phosphodiesterase 4 (PDE-4), mast cell trytase, NO, adenosine, IKK2, GATA3, ICAM-1, VCAM-1, and ICOS.

The totality of disclosure in US patent app. pub. No. 2008/0171014, including all references cited herein are incorporated by reference in their entirety.

This disclosure is further illustrated by the following examples which should not be construed as limiting. The entire contents of all references, patents and published patent applications cited throughout this application, as well as the Figures and the Sequence Listing, are hereby incorporated herein by reference.

EXAMPLES

Example 1: Study of the Efficacy of a Recombinant Humanized, High-Affinity, Selective, Anti-Interleukin-13 Monoclonal Antibody, for Eosinophilic Esophagitis Introduction Interleukin (IL)-13 stimulation of primary human oesophageal epithelial cells induces expression of eotaxin-3, an eosinophil chemo-attractant protein, and periostin, an extracellular matrix adhesion protein. These IL-13-induced proteins are over-expressed in esophageal tissue of patients with eosinophilic esophagitis (EoE), and strongly promote allergic inflammation. An anti-IL-13 antibody, RPC4046 (also referred to as 13C5.5), binds to human type IL-13 and an IL-13 sequence variant, R110Q. These cytokines have been shown to enhance human allergic inflammation. RPC4046 is highly selective for IL-13 and does not bind to other cytokines.

Objectives

The efficacy and safety of RPC4046 was evaluated in a phase 2 study in patients with EoE. The primary objective of the trial was to characterize the effect of RPC4046 on eosinophil counts in esophageal biopsy samples from subjects with symptomatic eosinophilic esophagitis (EoE). The secondary objectives of the study were to characterize the effects of RPC4046 on clinical symptoms of EoE; characterize the effects of RPC4046 on EoE endoscopic score; characterize the effects of RPC4046 on esophageal histologic findings; and characterize the safety and tolerability of RPC4046, including the development of anti-RPC4046 antibodies.

Study Design

A double-blind, placebo-controlled, dose-finding study was conducted at 40 canters in North America and Switzerland. Patients with EoE (n=100, aged 18-65) were randomized to 180 mg (low dose; LD) or 360 mg (high dose; HD) RPC4046 or PBO (1:1:1) in a Day 1 intravenous loading dose, followed by weekly subcutaneous doses for 15 weeks. Table 1 provides a summary of patient demographics. Esophageal eosinophil counts were measured from biopsies during screening, at week 16, and at early termination, if applicable. The frequency and severity of dysphagia clinical symptoms were assessed using the Eosinophilic Esophagitis Activity Index (EEsAI) and recorded in a daily symptom diary (DSD), which contained answers to a standard questionnaire, from which a score was computed (Table 2). Safety was monitored throughout the study. The primary endpoint was change from baseline (BL) to week 16 in mean oesophageal eosinophil count. The study was powered for the primary endpoint. Secondary endpoints included mean change from BL to week 16 in dysphagia clinical symptom frequency and severity.

TABLE 1

Summary of patient demographics.

|  | Placebo (N = 34) n (%) | RPC4046 180 mg (N = 31) n (%) | RPC4046 360 mg (N = 34) n (%) |
|---|---|---|---|
| Number of Subjects Randomized | 34 (100) | 32 (100) | 34 (100) |
| Not Dosed[a] | 0 | 1 (3.1) | 0 |
| ITT Population[a] [b] | 34 (100) | 31 (96.9) | 34 (100) |
| Per Protocol Population[a] [c] | 34 (100) | 29 (90.6) | 34 (100) |
| Safety Population[a] [d] | 34 (100) | 31 (96.9) | 34 (100) |
| Number of Subjects Who Completed the Double-Blind Treatment Period | 32 (94.1) | 28 (87.5) | 30 (88.2) |
| Who Discontinued the Double-Blind Treatment Period | 2 (5.9) | 4 (12.5) | 4 (11.8) |

[a]Percentages are based on the number of randomized subjects.
[b] The ITT population consists of all randomized subjects who received at least one dose of study drug, with treatment assignment designated according to randomized treatment.
[c] The Per Protocol population is a subset from the ITT population with high treatment compliance and without any exclusionary protocol deviations.
[d] The Safety population consists of all subjects receiving any double-blind study drug. Safety analyses will be carried out on this population according to the highest SC dose of RPC4046 actually received.

The double-blind phase was subsequently followed up with an open-label extension (52 weeks), wherein all subjects were treated at the high dose of RPC4046.

Subject Selection:
Subjects were selected/excluded based on the following criteria:
Inclusion Criteria:
 1. Documented diagnosis of EoE after at least 8 weeks of high-dose PPI therapy prior to screening;
 2. Histologic evidence of EoE with a peak eosinophil count of ≥15/HPF, from 2 of 3 (proximal, mid-, and/or distal) levels of the esophagus at the screening endoscopy;
 3. Subject must have experienced dysphagia on a minimum of 4 days and completed the DSQ on ≥70% of days in any 2 consecutive weeks of the screening period and in the 2 weeks prior to the baseline visit;
 4. History of on average at least 2 episodes of dysphagia (with intake of solids off anti-inflammatory therapy) per week in the 4 weeks prior to screening and on average at least 2 episodes of documented dysphagia per week in the weeks between screening and baseline; dysphagia is defined as trouble swallowing solid food, or having solid food stick, by patient report;
 5. Must remain on a stable diet ≥3 months prior to the screening visit and continue any dietary therapy and/or medical regimens in effect at the screening visit;
Exclusion Criteria:
 1. Prior participation in a RPC4046 clinical trial;
 2. Subject has any condition or abnormality that would compromise the safety of the subject or interfere; with or complicate the assessment of signs or symptoms of EoE;
 3. Subject has used immunomodulatory therapy within 8 weeks prior to screening;
 4. Subject has been using swallowed topical corticosteroid for EoE or systemic corticosteroid for any condition within the 4 weeks prior to the qualifying EGD, or anticipates use during the treatment period;
 5. Subject has been on inhaled or intranasal steroids and not on stable treatment for greater than 3 months prior to screening visit or anticipates change during the study;
 6. Subject has initiated, discontinued, or changed dosage regimen of PPIs, H2 antagonists, antacids, antihistamines, or leukotriene inhibitors for any condition;
 7. Subject has an esophageal stricture that does not allow passage of a diagnostic adult upper endoscope or has had esophageal dilation within the 3 months prior to screening;
 8. Treatment with an investigational drug within 2 months or within 5 half-lives (if known), whichever is longer, prior to screening.

Endpoints

A key primary endpoint of the study is the change from Baseline to Week 16 in the mean esophageal eosinophil count measured in the 5 most inflamed high powered field (HPF) from the esophageal biopsies. A key secondary endpoint of the study is the mean change from Baseline to Week 16 in the dysphagia clinical symptom frequency and severity as assessed by a daily symptom diary completed over two weeks. Additionally, various safety and tolerability endpoints are also measurable. Safety and tolerability parameters are evaluated by the incidence, severity, and relationship of adverse events (AEs), serious AEs (SAEs), clinical laboratory abnormalities, changes in vital signs, physical examination abnormalities, and the presence of anti-drug antibodies. Subjects were also requested to enter answers to various symptom-related questions in a diary, which was used in the computation of a composite diary score (CDS) (Table 2).

TABLE 2

Sample daily symptom diary (DSD) questionnaire
and method employed to compute the CDS.

| Question | Text | Response/Action | Score |
|---|---|---|---|
| 1 | Did you try to eat solid food today? | Yes (go to Question #2)<br>No (go to Question #1a) | N/A |
| 1a | What is the primary reason you did not try to eat solid food today? | EoE symptoms<br>Reason other than EoE symptoms | N/A |
| 2 | During any meal today, did food go down slowly or get stuck in your throat or chest? | Yes<br>No | 1<br>0 |
| 3 | For the most difficult time you had swallowing today, did you have to do anything to make the food go down or to get relief? | If Question #2 is no<br>If Question #2 is yes:<br>No, it got better or cleared up on its own<br>Yes, I had to drink liquid to get relief<br>Yes, I had to cough and or gag to get relief<br>Yes, I had to vomit to get relief<br>Yes, the stuck food had to be removed by a doctor | 0<br>1<br>2<br>3<br>4<br>5 |
| 4 | Did you have any pain associated with swallowing food today? | Yes<br>No | N/A |
| 4a | How would you rate your pain associated with swallowing food today? | Range 1 (minimal pain)-10 (worst pain imaginable) | N/A |

Composite Diary Score =

$$\frac{(\text{Sum of } Q2 \text{ and } Q3 \text{ scores over period})}{\text{Number of days without missing data}} \times \text{Length of Period}$$

Sampling

To maximize consistency, biopsies were obtained from proximal and distal esophagus (i.e., 4 biopsy fragments from each level) at screening. Additional biopsies from mid-esophagus was encouraged and effort was made to obtain subsequent biopsies from the same levels. The biopsies were blinded and read by single central pathologist. To be eligible for trial, subjects were evaluated for peak eosinophil count of ≥15/HPF, from 2 of 3 (proximal, mid-, and/or distal) levels of the esophagus at the screening endoscopy.

Summary of Results 90 patients completed the initial 16 week study. Demographic/disease characteristics were comparable between treatment arms. At baseline, mean oesophageal eosinophil count was 92.4 (placebo; PBO), 116.6 (low dose; LD), and 122.6 (high dose; HD). Mean oesophageal eosinophil count measured in the 5 most inflamed high-powered fields from the oesophageal biopsies were significantly reduced from baseline (BL) for both doses of RPC4046 over the 16-week treatment period (mean change PBO: −4.4, LD: −94.8; and HD: −99.9 [both p<0.0001 versus placebo]). At baseline, mean dysphagia symptom composite diary score was 29.4 (PBO), 27.63 (LD), and 29.03 (HD). Decreases in dysphagia clinical symptoms were observed among patients treated with RPC4046 LD and HD compared to PBO based on composite diary score (PBO: −6.4; LD: −5.3 [p=0.9959 vs PBO), and HD: −13.3 [p=0.0733 versus PBO]). Subgroup analysis by steroid refractory status at 16 week showed improvement in dysphagia as reported by DSD. RPC4046 was well-tolerated with a favorable safety profile. The net change in dysphagia over the 16-week treatment period as measured by $DSD^a$ is shown in Table 3.

TABLE 3

Mean change from baseline to Week 16 in the dysphagia clinical symptom frequency and severity as assessed by the DSD completed over 2 weeks.

| | Non-steroid-refractory pts | | | Steroid-refractory pts | | |
| | | RPC4046 | | | RPC4046 | |
| | PBO (n = 18) | LD (n = 12) | HD (n = 16) | PBO (n = 14) | LD (n = 14) | HD (n = 12) |
|---|---|---|---|---|---|---|
| Dysphagia Change from BL | −10.8 | −10.0 | −14.0 | −0.8 | −1.3 | −12.3 |

Detailed Results

Figure 2A:
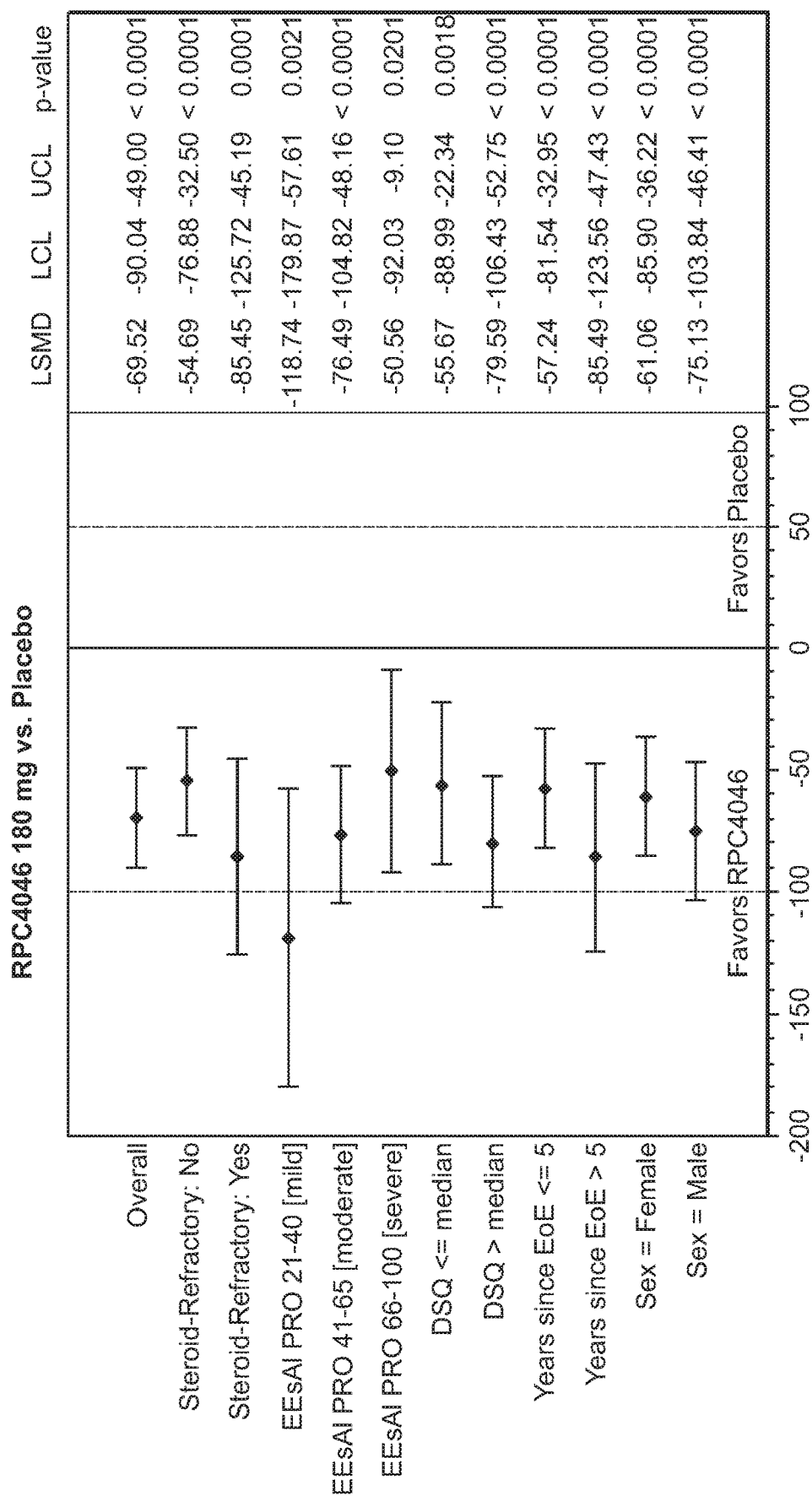
FIG. 2(a) shows mean esophageal eosinophil counts (cells/hpf) at week 16 in placebo versus subjects who were treated with the low (180 mg) dose of RPC4046.
Figure 2B:
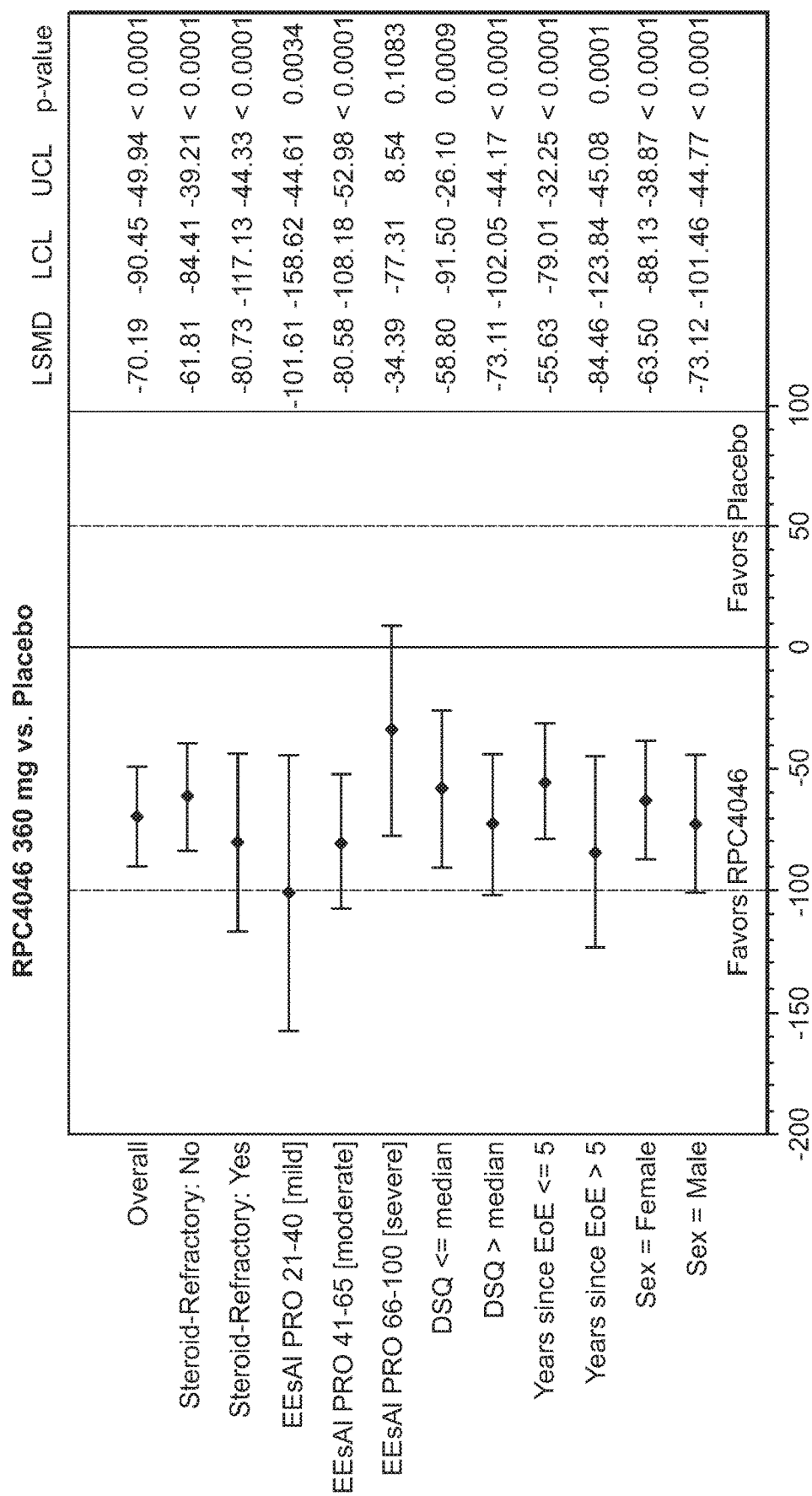
FIG. 2(b) shows mean esophageal eosinophil counts (cells/hpf) at week 16 in in placebo versus subjects who were treated with the high (360 mg) dose of RPC4046.

In a first study, subjects were provided with placebo or a low or high dose of the therapeutic agent. The mean esophageal eosinophil counts (cells/hpf) was calculated at baseline and at week 16. It was found that treatment with both the low dose (180 mg) and the high dose (360 mg) RPC4046 resulted in a statistically significant reduction in the mean esophageal eosinophil count at week 16 compared to the controls. The results are presented in FIG. 1. FIG. 2(a) shows mean esophageal eosinophil counts (cells/hpf) at week 16 in placebo versus subjects who were treated with the low (180 mg) dose of RPC4046 (further highlight cell counts within various subgroups of patients). FIG. 2(b)

shows mean esophageal eosinophil counts (cells/hpf) at week 16 in in placebo versus subjects who were treated with the high (360 mg) dose of RPC4046 (further highlight cell counts within various subgroups of patients).

Figure 3:
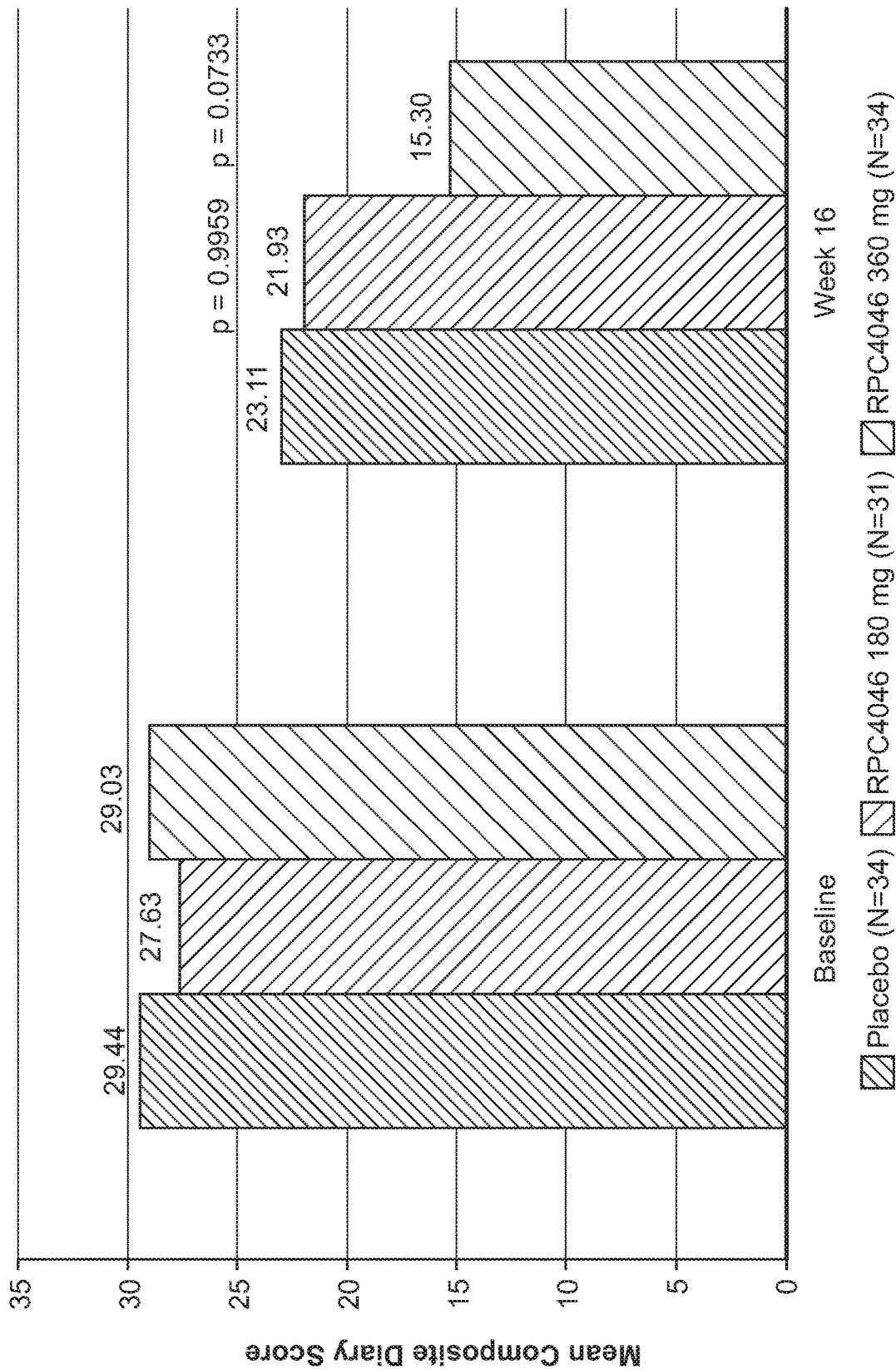
FIG. 3 shows mean dysphagia symptom composite diary score (a key secondary endpoint) at week 16 in subjects belonging to the ITT group (randomized subjects who received at least one dose of RPC4046) who were treated with the low dose (180 mg) or high dose (360 mg) of RPC4046. Statistical significance was computed by measuring p-values from ANCOVA model adjusted for steroid refractory status and baseline composite diary score. The results are summarized in Table 4.

In a second study, subjects were provided with placebo or a low or high dose of the therapeutic agent. The mean dysphagia symptom composite diary score (a key secondary endpoint) was calculated at baseline and at week 16. It was found that treatment with both the low dose (180 mg) and the high dose (360 mg) RPC4046 resulted in a reduction in the mean dysphagia symptom composite diary score at week 16 compared to the controls. The results are presented in FIG. 3. A summary of the results is provided in Table 4.

TABLE 4

Summary of results from the study evaluating dysphagia symptom composite diary score at week 16 in subjects belonging to the ITT group who were treated with the low dose (180 mg) or high dose (360 mg) of RPC4046. The various statistical parameters, e.g., least squares mean difference (LSMD), confidence interval (CI), means and medians were computed from the dataset. Statistical significance was determined via p-values from ANCOVA model adjusted for steroid refractory status and baseline composite diary score.

|  | Placebo (N = 34) | RPC4046 180 mg (N = 31) | RPC4046 360 mg (N = 34) |
| --- | --- | --- | --- |
| Baseline |  |  |  |
| n | 32 | 26 | 28 |
| Mean (SD) | 29.4 (10.70) | 27.6 (13.18) | 29.0 (10.13) |
| Median | 28.4 | 28.5 | 27.5 |
| Min, Max | 11, 51 | 6.6, 52 | 11, 49 |
| Week 16 |  |  |  |
| n | 34 | 30 | 32 |
| Mean (SD) | 23.1 (19.12) | 21.9 (17.29) | 15.3 (17.14) |
| Median | 21 | 26.1 | 6.2 |
| Min, Max | 0, 52.9 | 0, 46.7 | 0, 45.5 |
| Change to Week 16 |  |  |  |
| n | 32 | 26 | 28 |
| Mean (SD) | −6.4 (15.4) | −5.3 (12.26) | −13.3 (15.26) |
| LSMD (95% CI) |  | 0.02 (−7.29, 7.33) | −6.50 (−13.63, 0.63) |
| p-value |  | 0.9959 | 0.0733 |

Figure 4:
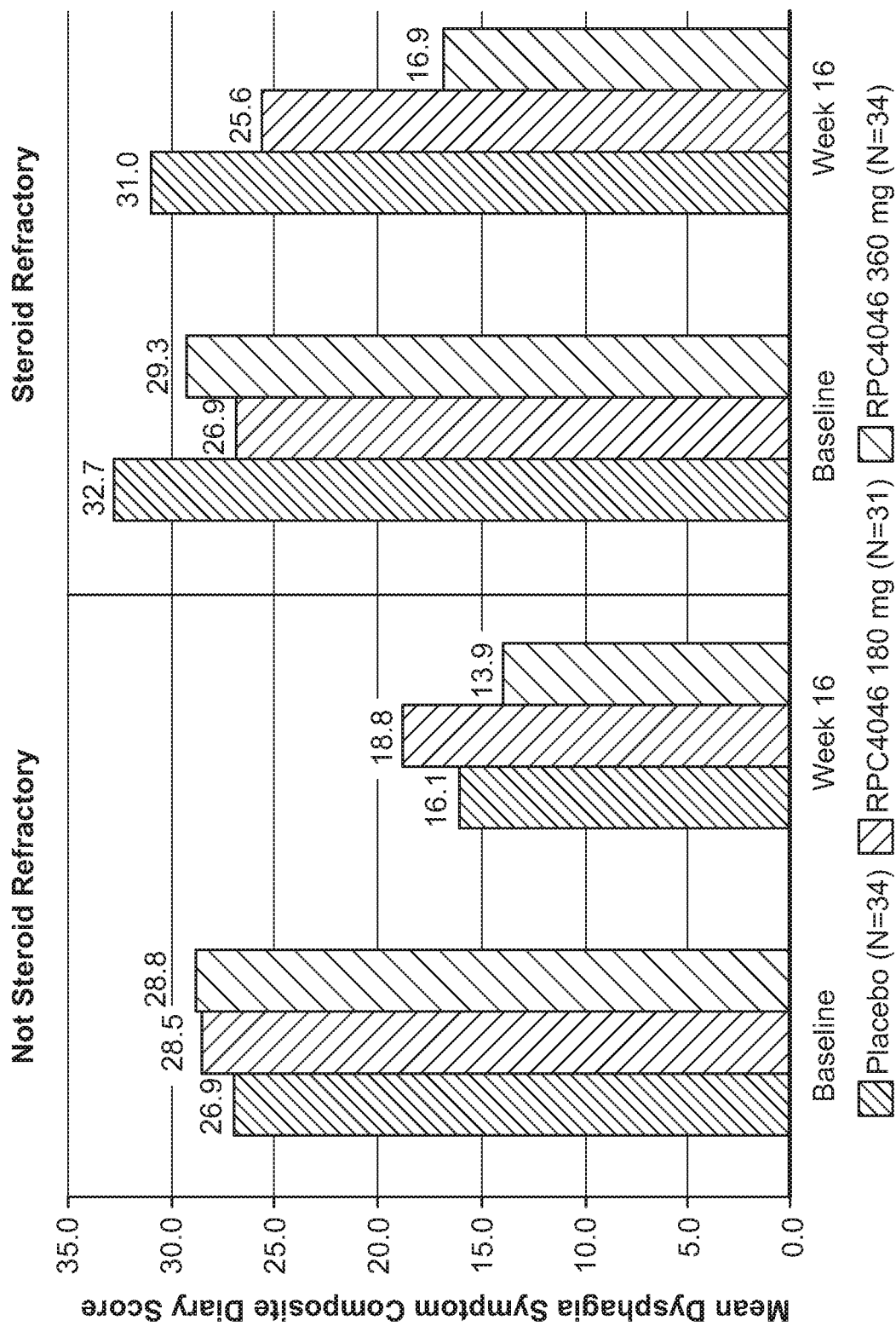
FIG. 4 shows mean dysphagia symptom composite diary score (a key secondary endpoint) at week 16 in subjects belonging to the ITT group (sub-grouped according to steroid refractory status) who were treated with the low dose (180 mg) or high dose (360 mg) of RPC4046. The results are summarized in Table 5.

A subgroup analysis (based on steroid-refractory status) of the subjects was performed, the results of which is shown in FIG. 4. A dose-dependent reduction in mean dysphagia symptom composite diary score was observed in steroid-refractory subjects. The results are summarized in Table 5.

TABLE 5

Summary of results from the study evaluating dysphagia symptom composite diary score at week 16 in subjects belonging to the ITT group (sub-grouped according to steroid refractory status) who were treated with the low dose (180 mg) or high dose (360 mg) of RPC4046. The various statistical parameters, e.g., least squares mean difference (LSMD), confidence interval (CI), means and medians were computed from the dataset. Statistical significance was determined via p-values from ANCOVA model adjusted for baseline composite diary score.

| Steroid Refractory Status | Timepoint | Placebo (N = 34) | RPC4046 180 mg (N = 31) | RPC4046 360 mg (N = 34) |
| --- | --- | --- | --- | --- |
| NO | Change to Week 16 |  |  |  |
|  | n | 18 | 12 | 16 |
|  | Mean change (SD) | −10.8 (15.45) | −10.0 (8.63) | −14.0 (13.57) |
|  | LSMD (95% CI) |  | 0.93 (−9.2, 11.1) | −3.1 (−12.5, 6.25) |
|  | p-value |  | 0.8541 | 0.5042 |
| YES | Change to Week 16 |  |  |  |
|  | n | 14 | 14 | 12 |
|  | Mean Change (SD) | −0.8 (13.9) | −1.3 (13.75) | −12.3 (17.86) |
|  | LSMD (95% CI) |  | −1.3 (−13.2, 10.7) | −12.0 (−24.3, 0.3) |
|  | p-value |  | 0.8284 | 0.0547 |

Figure 5:
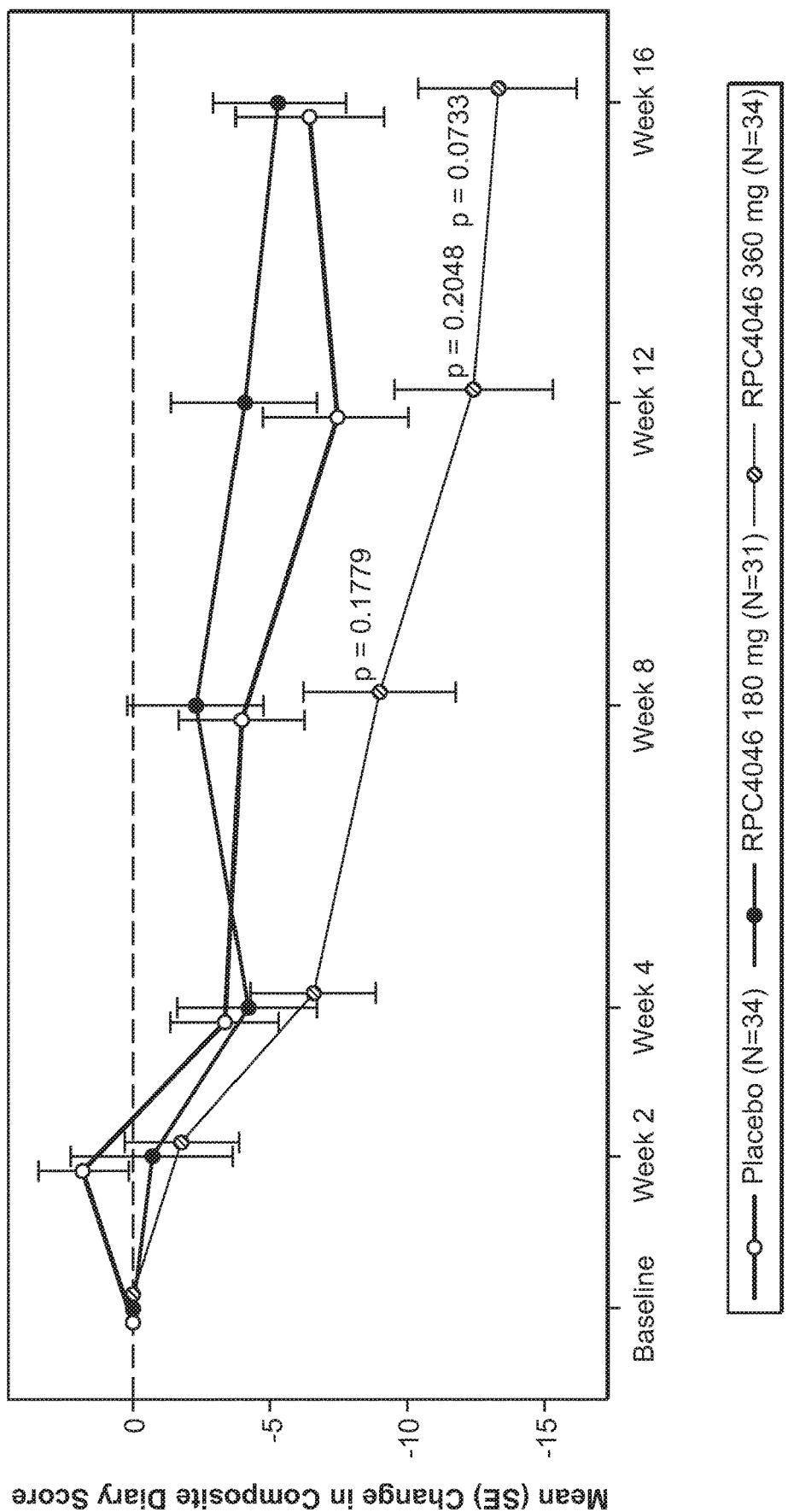
FIG. 5 shows mean dysphagia symptom composite diary score (over time) in subjects belonging to the ITT group who were treated with the low dose (180 mg) or high dose (360 mg) of RPC4046. Statistical significance was determined via p-values from ANCOVA model adjusted for steroid refractory status and baseline composite diary score. p-values were not adjusted for multiple comparisons.
Figure 6:
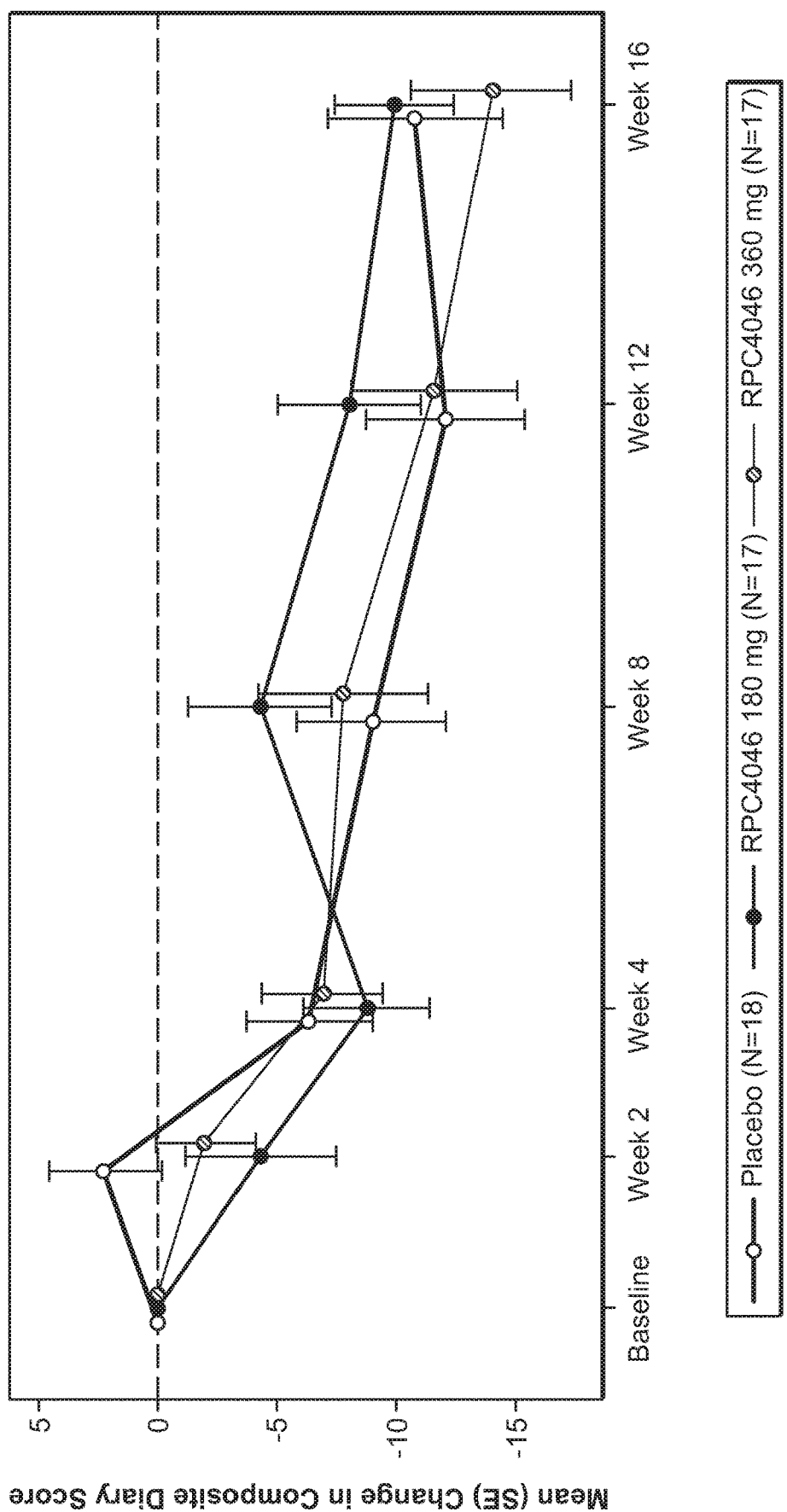
FIG. 6 shows mean dysphagia symptom composite diary score (over time) in subjects belonging to the non-steroid refractory sub-group who were treated with the low dose (180 mg) or high dose (360 mg) of RPC4046. Statistical significance was determined via p-values from ANCOVA model adjusted for steroid refractory status and baseline composite diary score. p-values were not adjusted for multiple comparisons.
Figure 7:
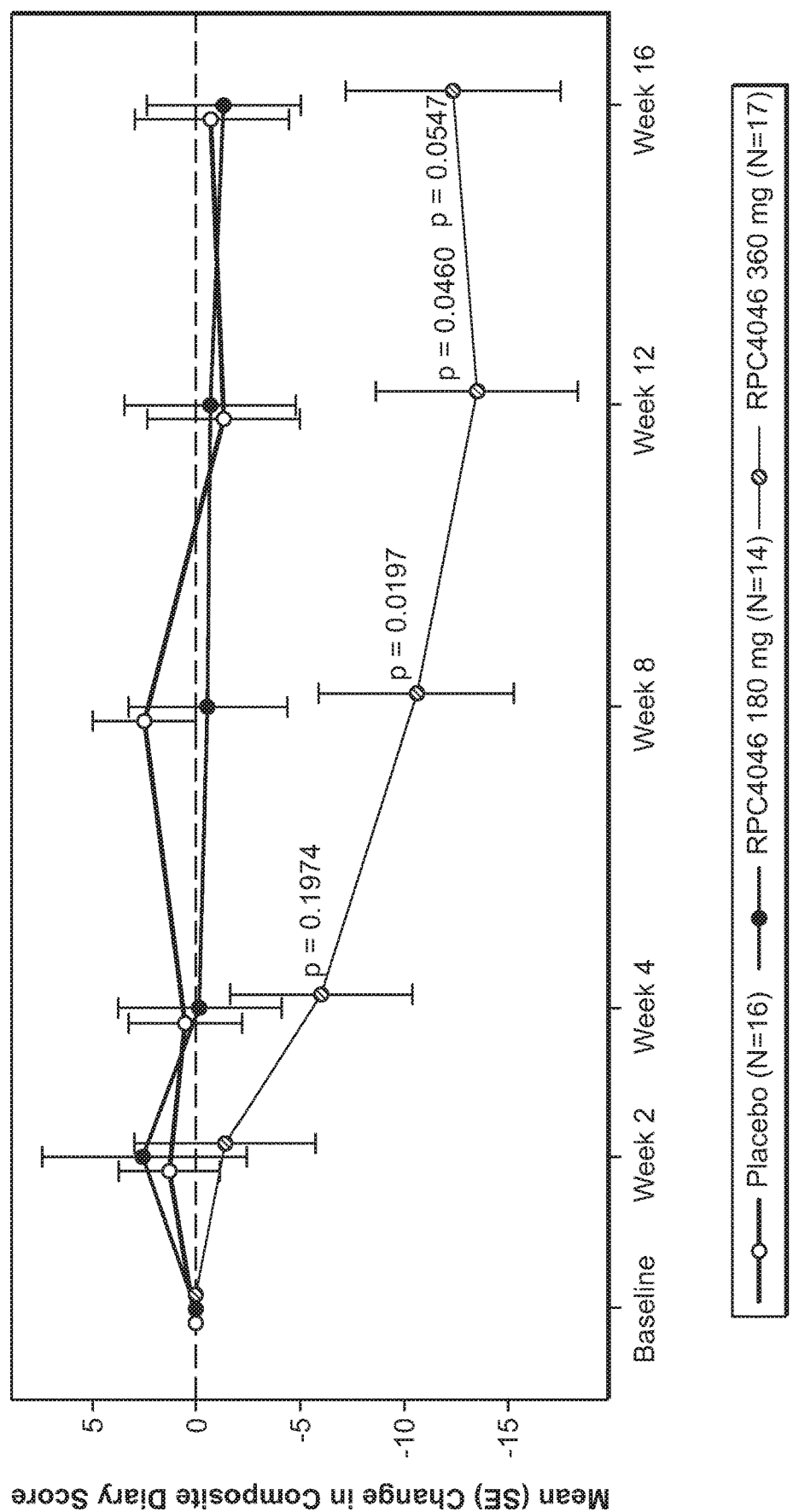
FIG. 7 shows (over time) in subjects belonging to the steroid refractory sub-group who were treated with the low dose (180 mg) or high dose (360 mg) of RPC4046. Statistical significance was determined via p-values from ANCOVA model adjusted for steroid refractory status and baseline composite diary score. p-values were not adjusted for multiple comparisons.

The mean dysphagia symptom composite diary scores (over a 16 week period; monitoring once every two weeks) in subjects provided with a placebo or who were treated with the low dose (180 mg) or high dose (360 mg) of RPC4046 are shown in FIG. 5. It can be seen that treatment with a higher dose (360 mg) of RPC4046 results in net reduction in mean dysphagia symptom composite diary score at week 16 compared to placebo, which approached statistical significance (p=0.0733). In the subgroup analysis (based on steroid-refractory status of the subjects), it was found that the steroid refractory sub-group benefited more (FIG. 7) than the non-steroid-refractory subgroup (FIG. 6).

Figure 8:
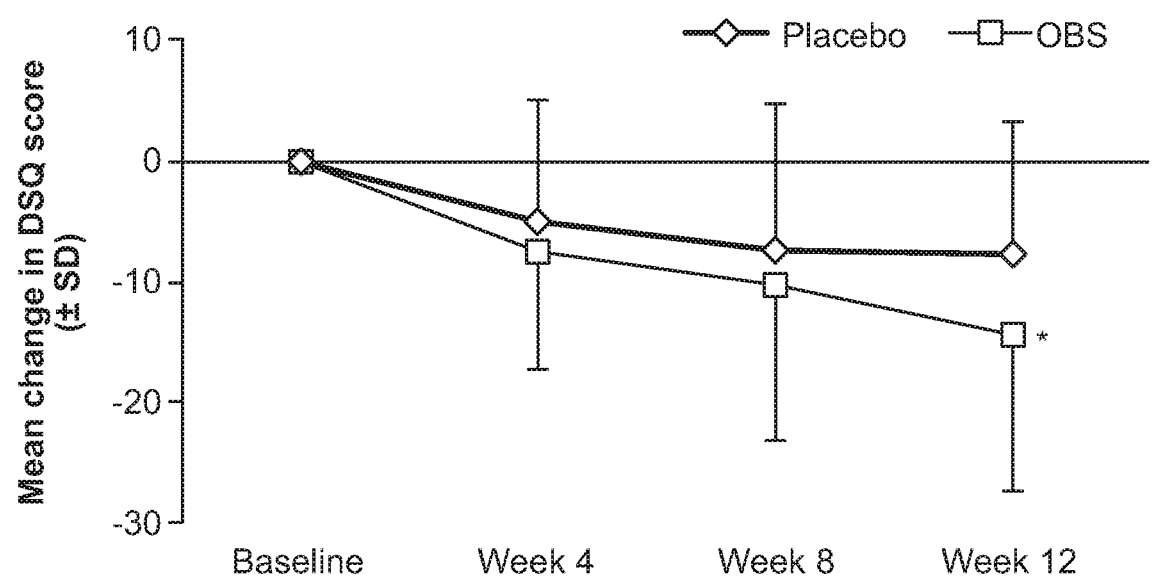
FIG. 8 shows mean change in dysphagia symptom questionnaire (DSQ) scores from baseline in subjects treated with oral budesonide suspension (ODS) versus placebo. The bars indicate standard deviations (SD). Table 6 shows a summary of the results.

The results of a parallel study evaluating the efficacy of oral budenoside suspension (OBS) in subjects diagnosed with eosinophilic esophagitis (EoE) is shown in FIG. 8. A side by side comparison between the efficacy of oral budenoside suspension, RPC4046 and QAX576 is shown in Table 6.

TABLE 6

A summary of the results evaluating the efficacy of placebo, oral budesonide, RPC4046 and QAX576 across three different studies.

| | Oral Budesonide | | RPC4046 | | | QAX576 | |
|---|---|---|---|---|---|---|---|
| Sample Size | Pbo N = 42 | OBS N = 51 | Pbo N = 34 | 180 mg N = 31 | 360 mg N = 34 | Pbo N = 8 | Qax N = 17 |
| Age | 22 | | 37 | | | 30 | |
| EEOC Peak BL | 130 | 156 | 105.4 | 131.9 | 139.4 | 91.3 | 88.2 |
| EEOC Peak post | 113 | 39 | 104.8 | 28.9 | 31.3 | NR | NR |
| EEOC Mean BL | NR | NR | 92.4 | 116.7 | 122.6 | 39.1 | 35.4 |
| EEOC Mean post | NR | NR | 90.3 | 24.8 | 25.5 | 48.1 | 14.6 |
| Dysphagia score BL | 29 | 29.3 | 29.4 | 27.6 | 29 | NA | NA |
| Dysphagia score post | 21.5 (−7.5) | 15 (−14.3) p − 0.0096 | 23.1 (−6.4) | 21.9 (−5.3) | 15.3 (−13.3) p = 0.0733 | NA | NA |

Figure 9:
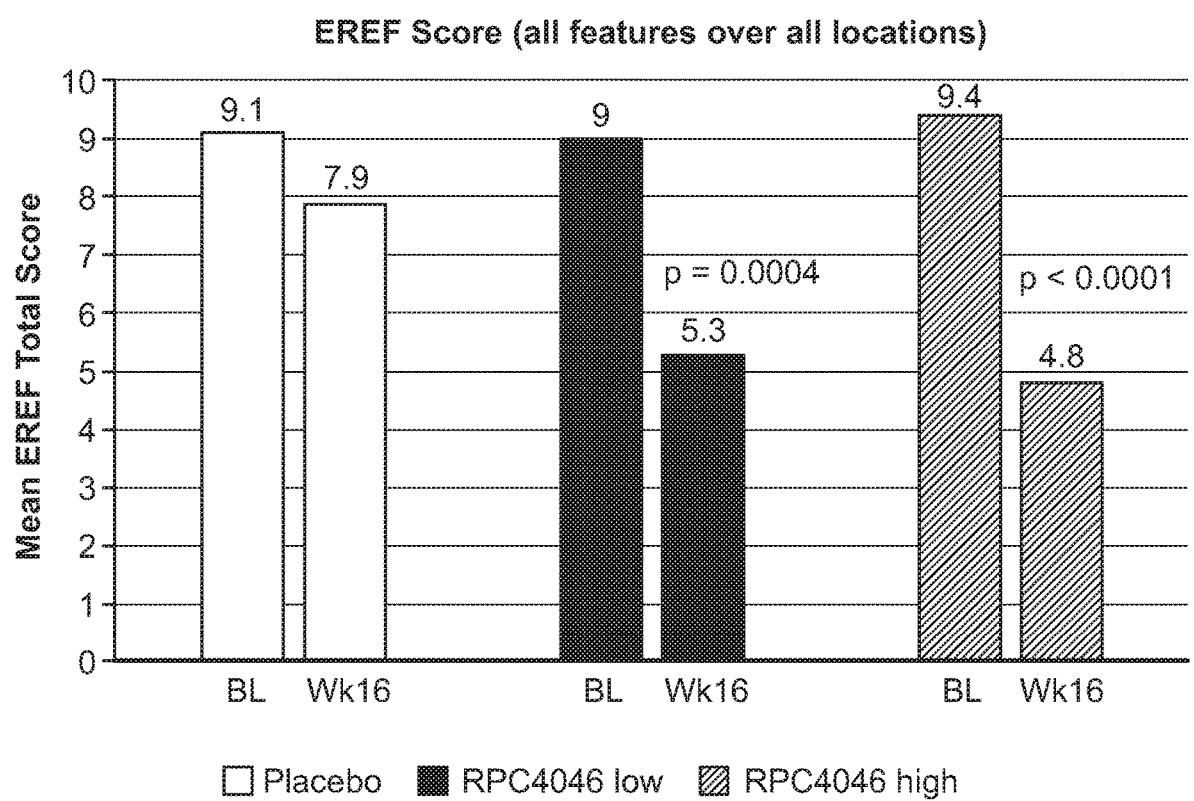
FIG. 9 shows mean eosinophilic esophagitis (EoE) endoscopic reference score (an additional secondary endpoint) in subjects at week 16. The EREF total score was computed from analysis of (EREFS features) in subjects at baseline and at week 16. Statistical significance was determined at p-value<0.05.

In further analysis, the mean eosinophilic esophagitis endoscopic reference score (EREF) in subjects at week 16 was analyzed for placebo and the two treatment arms. The EREF score is an additional secondary endpoint that is evaluated based on the presence of inflammatory markers (e.g., being positive for edema, exudates and/or furrows) and/or remodeling markers (e.g., being positive for fixed rings and/or strictures). The results (showing total score) are presented in FIG. 9. It can be seen that treatment with RPC4046 resulted in a net lowering of EREF score at week 16, with the reduction achieved with the higher dose of RPC4046 (360 mg) being statistically significant (p<0.0001).

Figure 10:
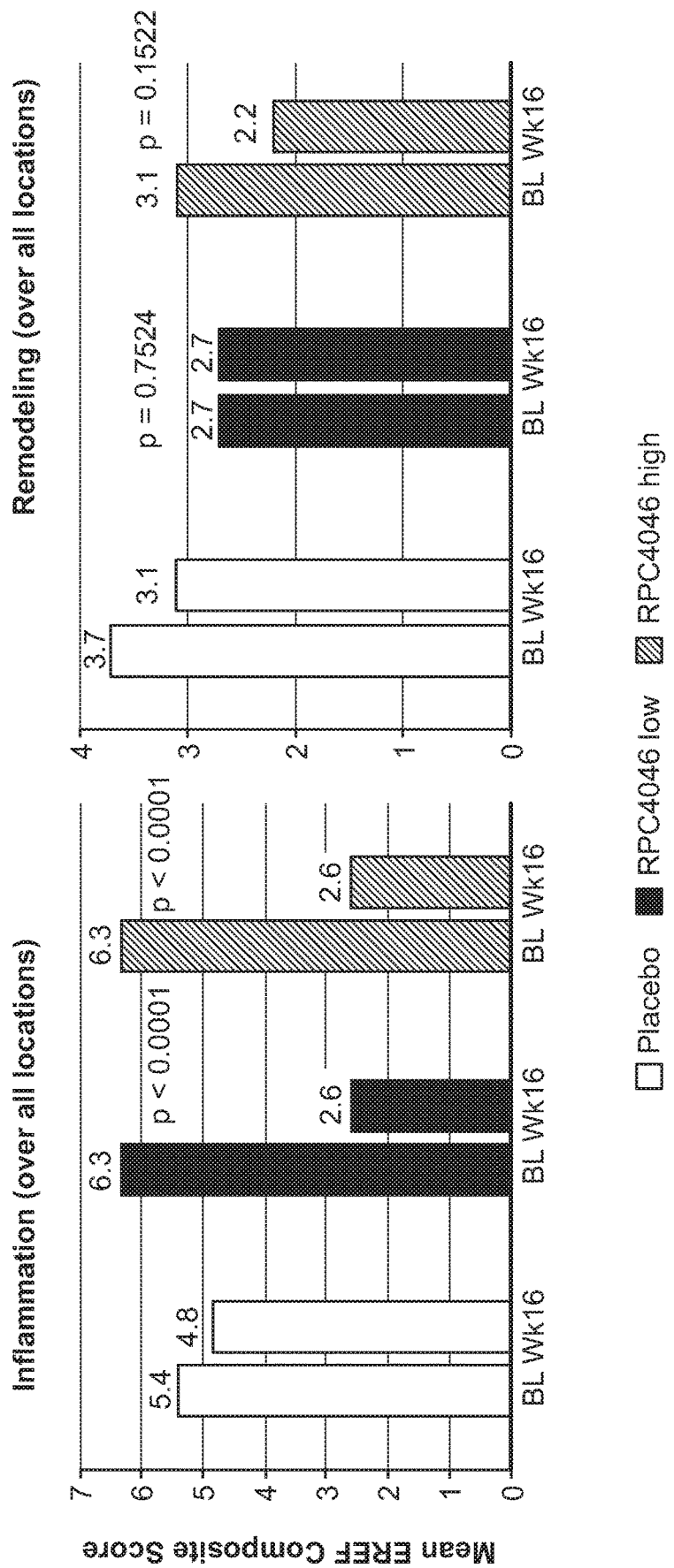
FIG. 10 shows mean eosinophilic esophagitis (EoE) endoscopic reference score in subjects at week 16, as evaluated for the presence of inflammatory markers (being positive for edema, exudates and/or furrows) or remodeling markers (e.g., being positive for fixed rings and/or strictures). Statistical significance was determined at p-value<0.05.

The results of the EREF study was further inspected by analyzing composite EREF score for inflammatory markers or remodeling markers. It was found that the higher dose of RPC4046 (360 mg) achieved statistically significant reduction in composite EREF score for inflammation (p<0.0001). The results are shown in FIG. 10.

Figure 11:
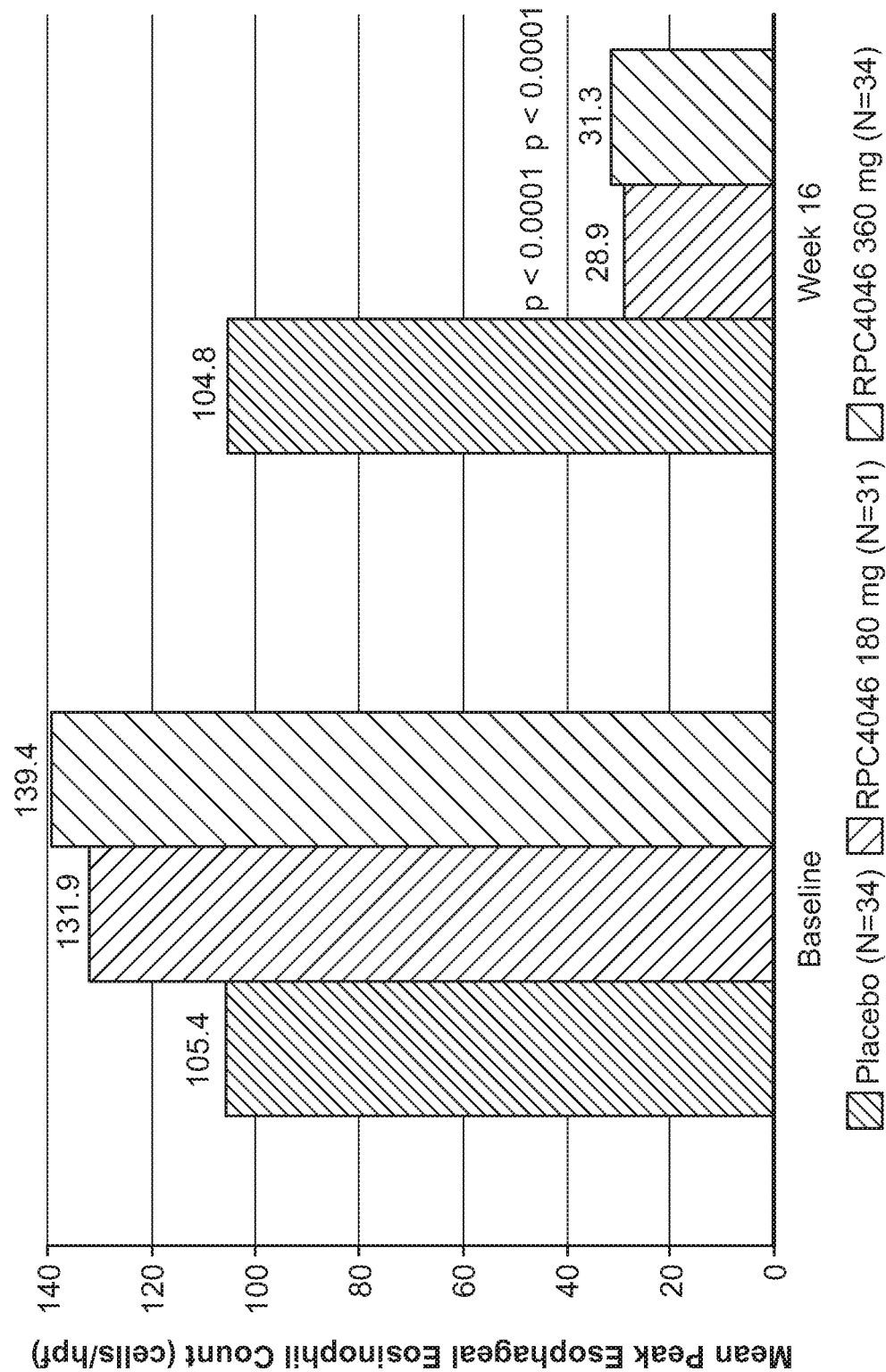
FIG. 11 shows mean esophageal eosinophil counts (cells/hpf) at baseline and at week 16 in the placebo group, low dose (180 mg) treatment group and high dose (360 mg) treatment group. Statistical significance was evaluated by determining p-values from ANCOVA model adjusted for steroid refractory status and baseline peak hpf esophageal eosinophil count. Table 7 shows a summary of the results.

Next, the effectiveness of RPC4046 (over placebo) in lowering peak esophageal eosinophil count in EoE subjects at week 16 was analyzed. It was found that treatment with both low (180 mg) and high dose (360 mg) of RPC4046 achieved statistical significance with regard to lowering of mean esophageal eosinophil counts. The results are shown in FIG. 11 and further summarized in Table 7.

TABLE 7

Summary of results from the study evaluating mean change in peak esophageal eosinophil count (cells/hpf) at week 16 in placebo versus subjects who were treated with the low dose (180 mg) or high dose (360 mg) of RPC4046. The various statistical parameters, e.g., least squares mean difference (LSMD), confidence interval (CI), means and medians were computed from the dataset. Statistical significance was determined via p-values from ANCOVA model adjusted for steroid refractory status and baseline peak hpf esophageal eosinophil count.

| | Placebo (N = 34) | RPC4046 180 mg (N = 31) | RPC4046 360 mg (N = 34) |
|---|---|---|---|
| Baseline | | | |
| n | 34 | 31 | 34 |
| Mean (SD) | 105.4 (60.42) | 131.9 (84.55) | 139.4 (79.94) |
| Median | 109.5 | 113.0 | 132.0 |
| Min, Max | 18, 212 | 24, 304 | 26, 389 |

TABLE 7-continued

Summary of results from the study evaluating mean change in peak esophageal eosinophil count (cells/hpf) at week 16 in placebo versus subjects who were treated with the low dose (180 mg) or high dose (360 mg) of RPC4046. The various statistical parameters, e.g., least squares mean difference (LSMD), confidence interval (CI), means and medians were computed from the dataset. Statistical significance was determined via p-values from ANCOVA model adjusted for steroid refractory status and baseline peak hpf esophageal eosinophil count.

|  | Placebo (N = 34) | RPC4046 180 mg (N = 31) | RPC4046 360 mg (N = 34) |
|---|---|---|---|
| Week 16 | | | |
| n | 33 | 28 | 30 |
| Mean (SD) | 104.8 (61.36) | 28.9 (39.75) | 31.3 (37.69) |
| Median | 103.0 | 15.0 | 15.0 |
| Min, Max | 16, 302 | 0, 159 | 0, 157 |
| Change to Week 16 | | | |
| n | 33 | 28 | 30 |
| Mean (SD) | −3.3 (70.05) | −106.6 (71.2) | −111.3 (90.07) |
| LSMD (95% CI) | | −80.6 (−104.5, −56.7) | −79.8 (−103.4, −56.2) |
| p-value | | <0.0001 | <0.0001 |

Figure 12:
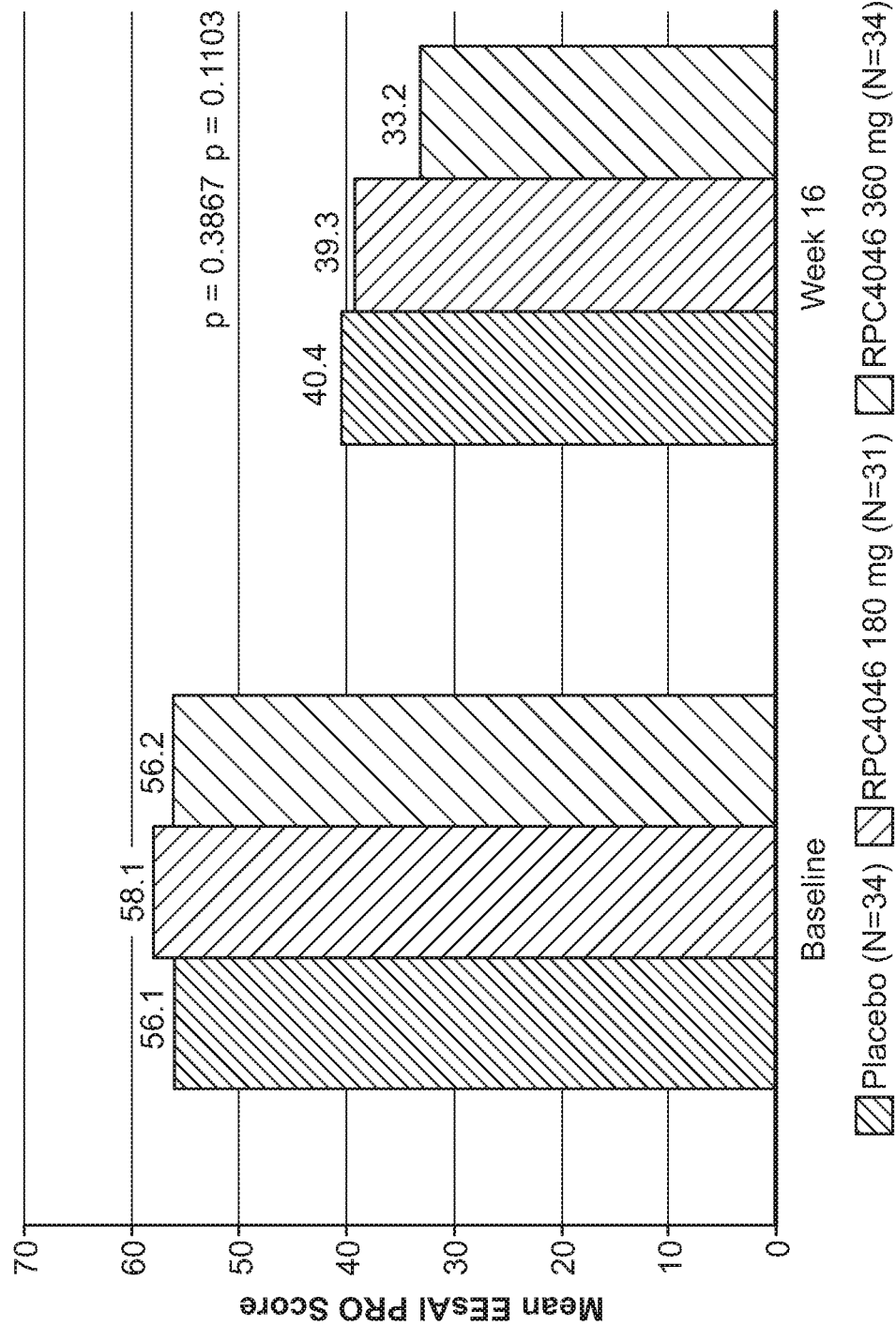
FIG. 12 shows mean EEsAI PRO scores at baseline and at week 16 in placebo versus subjects who were treated with the low dose (180 mg) or high dose (360 mg) of RPC4046. Statistical significance was determined via p-values from ANCOVA model adjusted for steroid refractory status and baseline EEsAIPRO score. Table 8 shows a summary of the results.

Additionally, a comparison of the mean EEsAI PRO scores at baseline and at week 16 between the placebo group and the treatment group was conducted. The results are shown in FIG. 12 and further summarized in Table 8.

TABLE 8

Summary of results from the study evaluating mean EEsAI PRO scores at baseline and at week 16 in placebo versus subjects who were treated with the low dose (180 mg) or high dose (360 mg) of RPC4046. The various statistical parameters, e.g., least squares mean difference (LSMD), confidence interval (CI), means and medians were computed from the dataset. Statistical significance was determined via p-values from ANCOVA model adjusted for steroid refractory status and baseline EEsAIPRO score.

|  | Placebo (N = 34) | RPC4046 180 mg (N = 31) | RPC4046 360 mg (N = 34) |
|---|---|---|---|
| Baseline | | | |
| n | 34 | 30 | 34 |
| Mean (SD) | 56.1 (13.19) | 58.1 (12.22) | 56.2 (13.21) |
| Median | 53.0 | 61.0 | 58.0 |
| Min, Max | 34, 94 | 27, 92 | 34, 94 |
| Week 16 | | | |
| n | 34 | 31 | 34 |
| Mean (SD) | 40.4 (22.19) | 39.3 (22.03) | 33.2 (26.37) |
| Median | 30.5 | 49.0 | 30.5 |
| Min, Max | 0, 78 | 0, 76 | 0, 94 |
| Change to Week 16 | | | |
| n | 34 | 30 | 34 |
| Mean (SD) | −15.8 (17.71) | −19.8 (18.58) | −23.0 (21.08) |
| LSMD (95% CI) | | −4.0 (−13.3, 5.2) | −7.2 (−16.2, 1.7) |
| p-value | | 0.3867 | 0.1103 |

Figure 13:
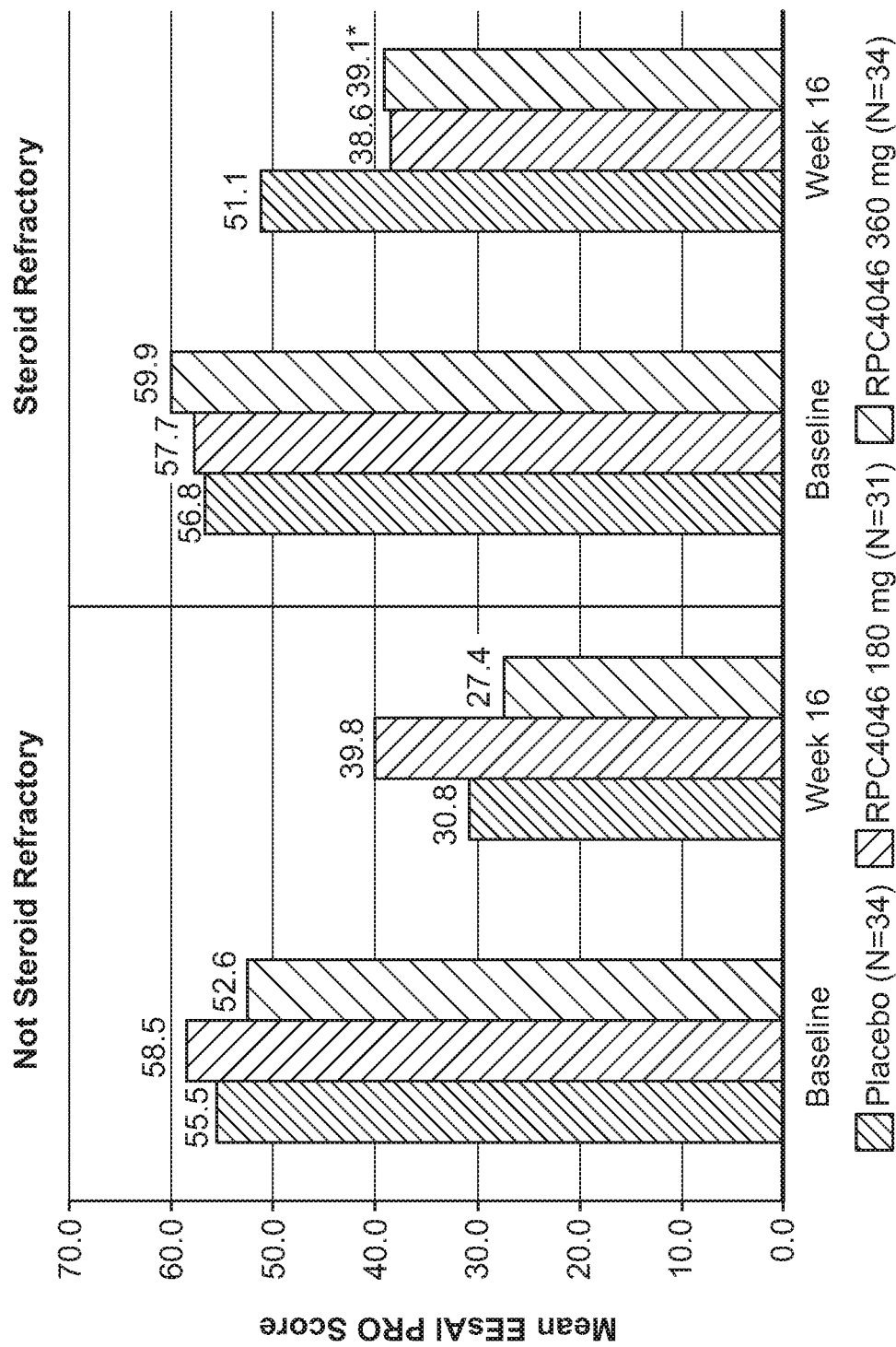
FIG. 13 shows mean EEsAI PRO scores at baseline and at week 16 in subjects who were sub-grouped according to steroid refractory status. Each subgroup was given placebo or treated with the low dose (180 mg) or high dose (360 mg) of RPC4046. Statistical significance was determined at p<0.05. * indicates p<0.05. The results are summarized in Table 9.

A dose-dependent reduction in mean EEsAI PRO was observed at week 16. In further sub-group analysis (based on steroid-refractory status), it was found that a statistically significant reduction in the mean EEsAI PRO score was observed in the steroid refractory sub-group. The results are shown in FIG. 13 and further summarized in Table 9.

TABLE 9

Summary of results from the study evaluating mean EEsAI PRO scores at baseline and at week 16 in steroid refractory versus non-steroid-refractory subjects who were given placebo or treated with the low dose (180 mg) or high dose (360 mg) of RPC4046. The various statistical parameters, e.g., least squares mean difference (LSMD), confidence interval (CI), means and medians were computed from the dataset. Statistical significance was determined via p-values from ANCOVA model adjusted for steroid refractory status and baseline EEsAIPRO score.

| Steroid Refractory Status | Timepoint | Placebo (N = 34) | RPC4046 180 mg (N = 31) | RPC4046 360 mg (N = 34) |
|---|---|---|---|---|
| NO | Change to Week 16 | | | |
| | n | 18 | 16 | 17 |
| | Mean change (SD) | −24.7 (16.36) | −20.4 (15.76) | −25.2 (16.76) |
| | LSMD (95% CI) | | 4.9 (−6.4, 16.3) | −1.2 (−12.4, 9.9) |
| | p-value | | 0.3875 | 0.8237 |
| YES | Change to Week 16 | | | |
| | n | 16 | 14 | 17 |
| | Mean Change (SD) | −5.8 (13.58) | −19.1 (21.96) | −20.8 (25.00) |
| | LSMD (95% CI) | | −13.5 (28.9, 1.9)– | −15.5 (−30.2, −0.8) |
| | p-value | | 0.0852 | 0.0393 |

Figure 14:
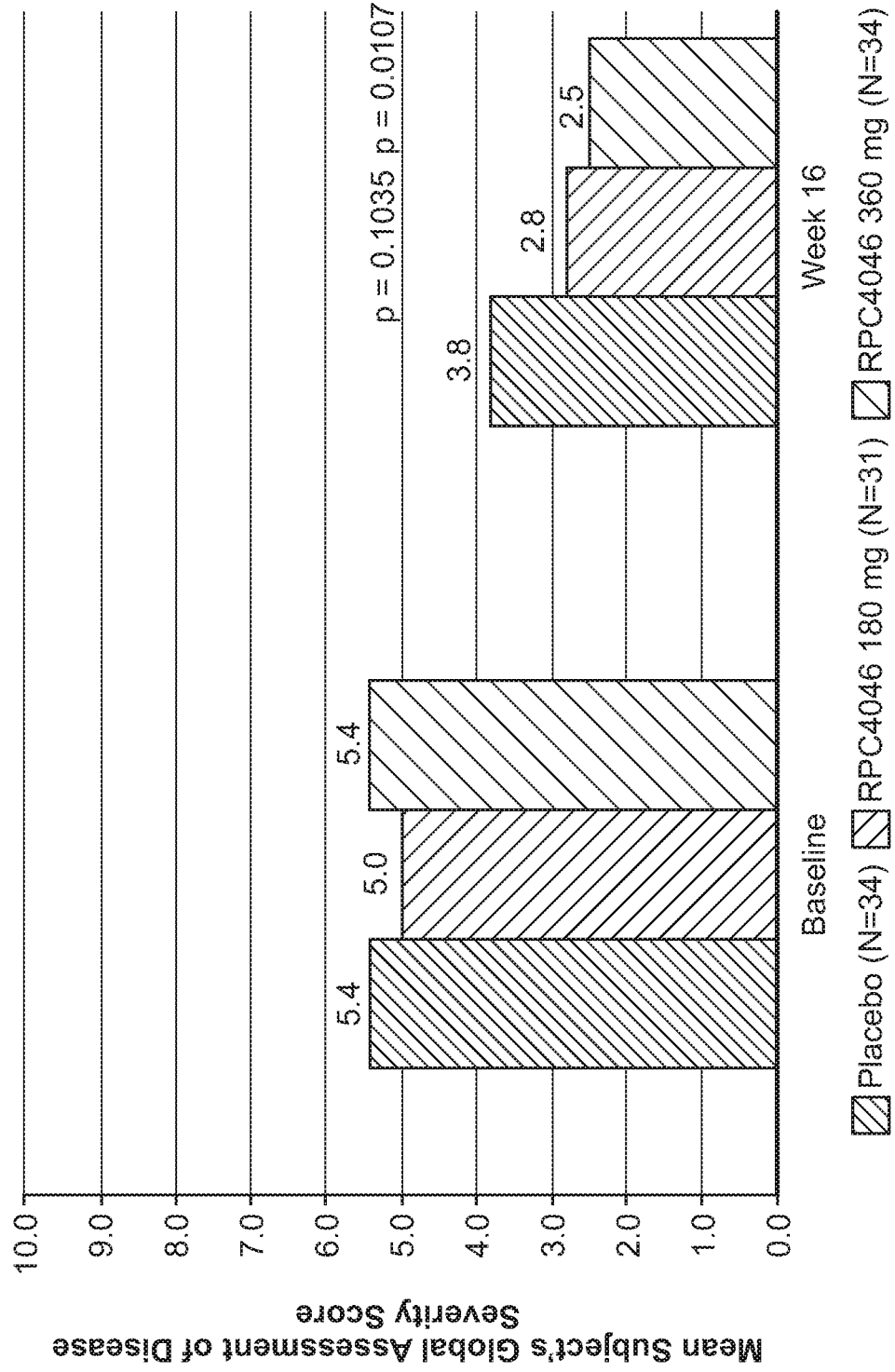
FIG. 14 shows mean subject's global assessment of disease severity at baseline and at week 16 in subjects who were given placebo or treated with the low dose (180 mg) or high dose (360 mg) of RPC4046. Statistical significance (at p<0.05) was determined by computing p-values from ANCOVA model adjusted for steroid refractory status and baseline global assessment of disease severity score. The results are summarized in Table 10.

Still further, the effectiveness of RPC4046 (over placebo) in lowering a subject's global assessment of disease severity at week 16 was analyzed. A dose-dependent reduction was observed in the treatment arm at week 16, with the reduction achieved within subjects treated with a higher dose (360 mg) RPC4046 achieving statistical significance over placebo. The results are shown in FIG. 14 and further summarized in Table 10.

TABLE 10

Summary of results from the study evaluating subject's global assessment of disease severity at baseline and at week 16 in subjects who were given placebo or treated with the low dose (180 mg) or high dose (360 mg) of RPC4046. The various statistical parameters, e.g., least squares mean difference (LSMD), confidence interval (CI), means and medians were computed from the dataset. Statistical significance (at $p < 0.05$) was determined by computing p-values from ANCOVA model adjusted for steroid refractory status and baseline global assessment of disease severity score.

| | Placebo (N = 34) | RPC4046 180 mg (N = 31) | RPC4046 360 mg (N = 34) |
|---|---|---|---|
| Baseline | | | |
| n | 32 | 30 | 32 |
| Mean (SD) | 5.4 (2.14) | 5.0 (2.20) | 5.4 (1.92) |
| Median | 6.0 | 5.0 | 5.0 |
| Min, Max | 1, 10 | 2, 9 | 2, 9 |
| Week 16 | | | |
| n | 33 | 28 | 31 |
| Mean (SD) | 3.8 (2.73) | 2.8 (1.90) | 2.5 (2.29) |
| Median | 3.0 | 3.0 | 2.0 |
| Min, Max | 0, 10 | 0, 7 | 0, 9 |
| Change to Week 16 | | | |
| n | 31 | 27 | 30 |
| Mean (SD) | −1.5 (1.95) | −2.0 (1.68) | −2.8 (2.71) |
| LSMD (95% CI) | | −0.9 (−1.9, 0.2) | −1.3 (−2.4, −0.3) |
| p-value | | 0.1035 | 0.0107 |

Figure 15:
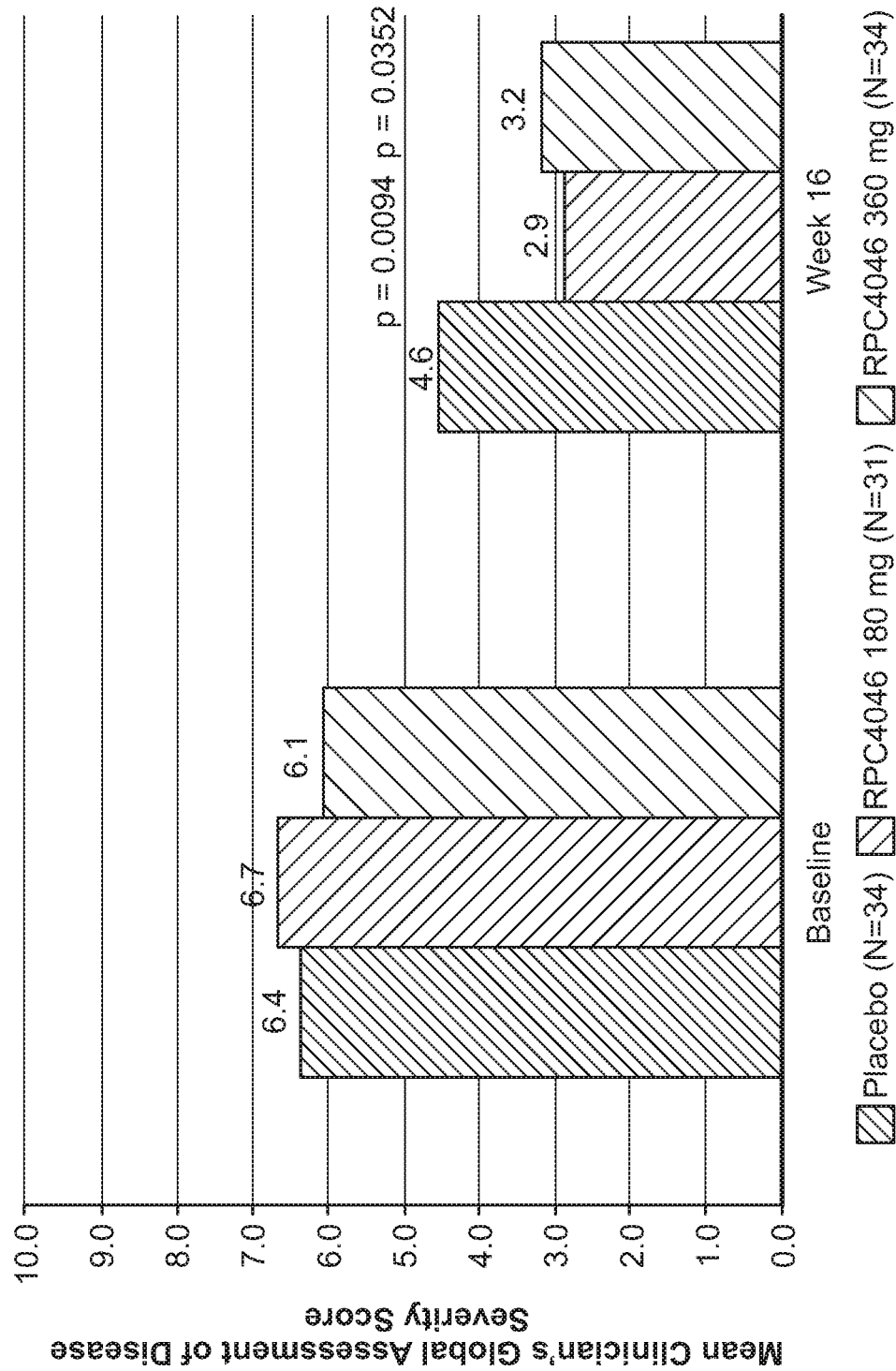
FIG. 15 shows mean clinician's global assessment of disease severity at baseline and at week 16 in subjects who were given placebo or treated with the low dose (180 mg) or high dose (360 mg) of RPC4046. Statistical significance (at p<0.05) was determined by computing p-values from ANCOVA model adjusted for steroid refractory status and baseline global assessment of disease severity score. The results are summarized in Table 11.

In the clinician's global assessment of disease severity at week 16, both the low as well as the high dose of RPC4046 achieved statistical significance. The results are shown in FIG. 15 and further summarized in Table 11.

TABLE 11

Summary of results from the study evaluating clinician's global assessment of disease severity at baseline and at week 16 in subjects who were given placebo or treated with the low dose (180 mg) or high dose (360 mg) of RPC4046. The various statistical parameters, e.g., least squares mean difference (LSMD), confidence interval (CI), means and medians were computed from the dataset. Statistical significance (at $p < 0.05$) was determined by computing p-values from ANCOVA model adjusted for steroid refractory status and baseline global assessment of disease severity score.

|  | Placebo (N = 34) | RPC4046 180 mg (N = 31) | RPC4046 360 mg (N = 34) |
|---|---|---|---|
| Baseline | | | |
| n | 34 | 30 | 33 |
| Mean (SD) | 6.4 (1.97) | 6.7 (1.82) | 6.1 (1.92) |
| Median | 7.0 | 7.0 | 6.0 |
| Min, Max | 2, 10 | 3, 10 | 2, 10 |
| 9 | | | |
| Week 16 | | | |
| n | 33 | 28 | 31 |
| Mean (SD) | 4.6 (3.02) | 2.9 (2.65) | 3.2 (2.44) |
| Median | 4.0 | 2.0 | 3.0 |
| Min, Max | 0, 10 | 0, 8 | 0, 8 |
| Change to Week 16 | | | |
| n | 33 | 27 | 30 |
| Mean (SD) | −1.8 (2.68) | −3.6 (2.71) | −2.9 (2.70) |
| LSMD (95% CI) | | −1.7 (−2.9, −0.4) | −1.3 (−2.5, −0.1) |
| p-value | | 0.0094 | 0.0352 |

Figure 16:
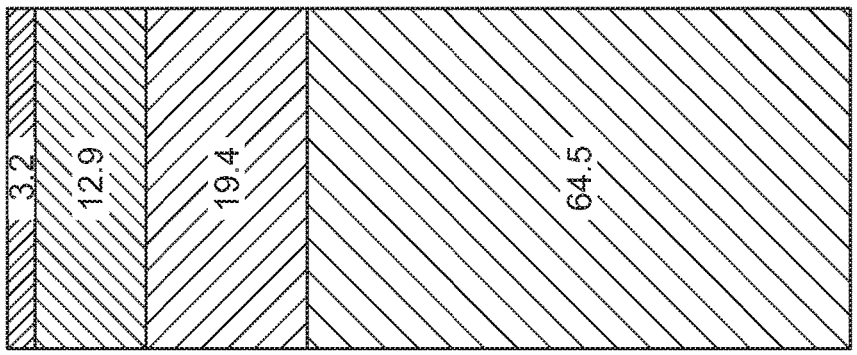
FIG. 16 shows subject's global impression at baseline and at week 16 in subjects who were given placebo or treated with the low dose (180 mg) or high dose (360 mg) of RPC4046. Statistical significance was determined at p<0.05.
Figure 16:
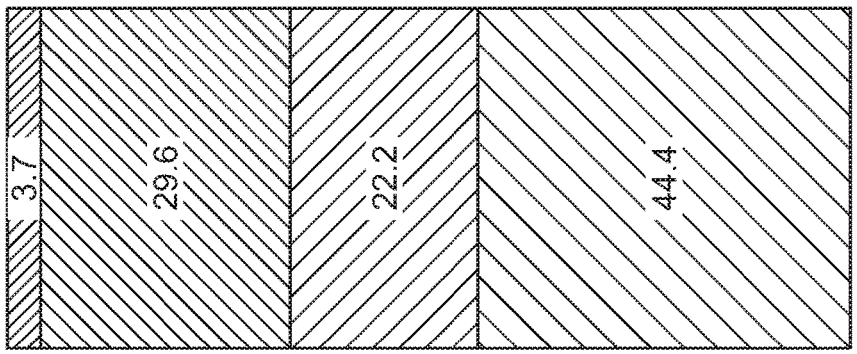
Figure 16:
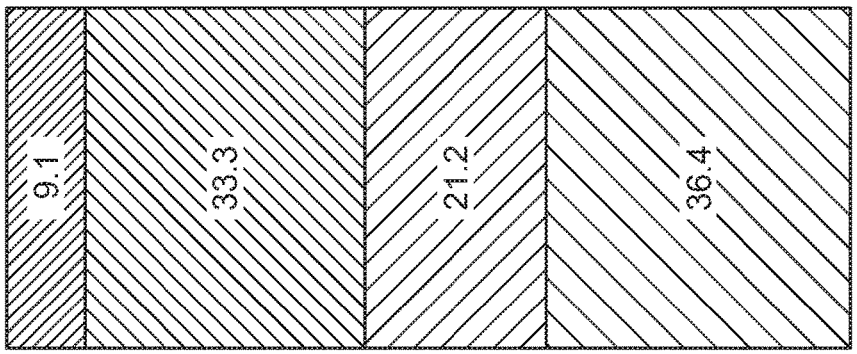

In the analysis of a subject's global impression at week 16, subjects treated with the higher dose (360 mg) of RPC4046 achieved statistical significance (p=0.0143). A larger number of subjects in the therapy arm responded as feeling "a lot better" or "a little better" compared to placebo. The results are shown in FIG. 16.

Figure 17:
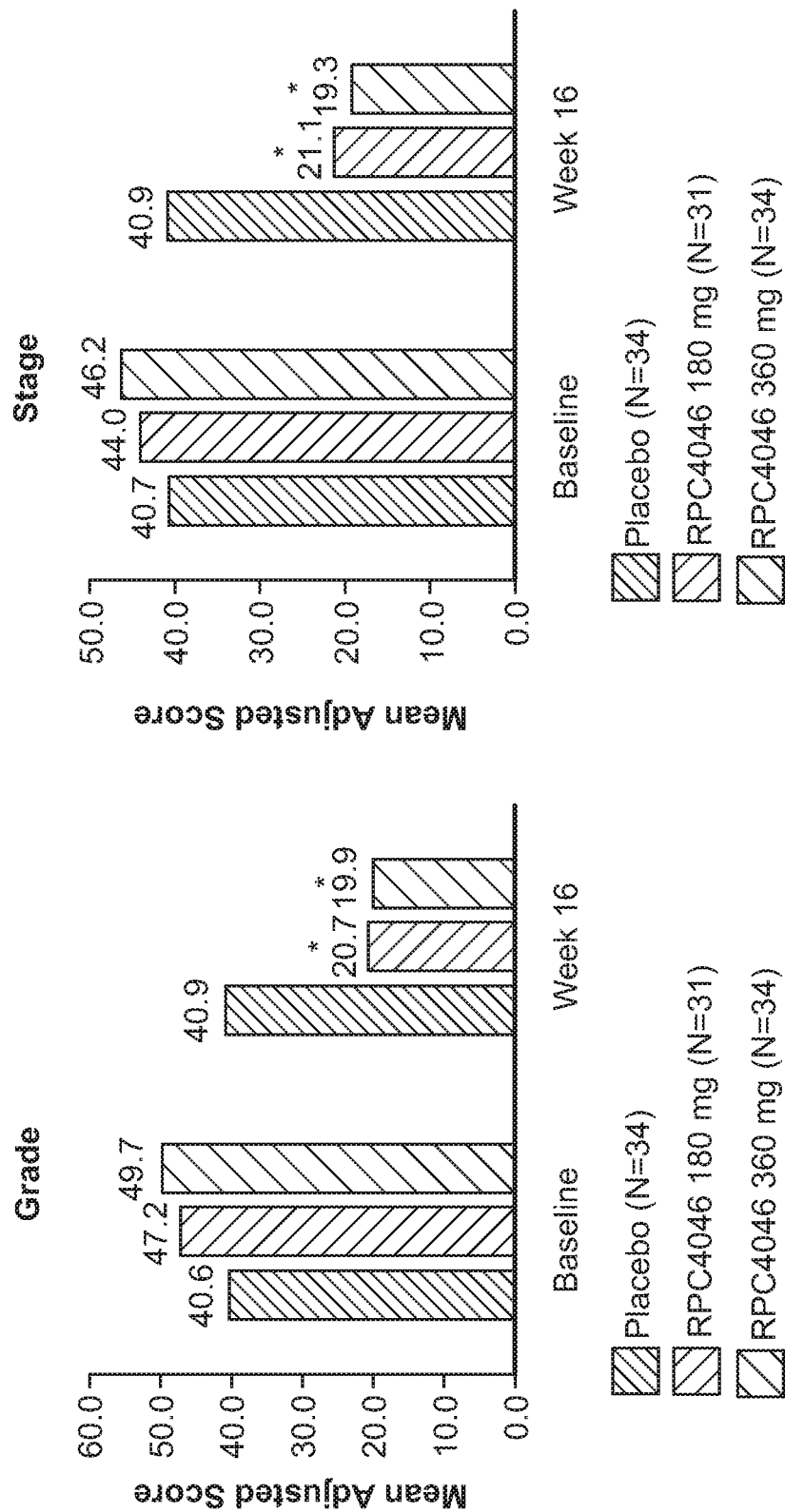
FIG. 17 shows the histology grade and mean stage-adjusted scores at baseline and at week 16 in subjects who were given placebo or treated with the low dose (180 mg) or high dose (360 mg) of RPC4046. Statistical significance was determined at p<0.05. * indicates p<0.0001.

Lastly, in the histology grade and mean stage-adjusted scores of esophageal biopsies were analyzed for the placebo group and the treatment arms at week 16. The results are shown in FIG. 17. Both the lower as well as the high dose arms in the therapeutic group achieved statistical significance (* indicates p<0.0001).

CONCLUSIONS

Treatment with RPC4046 reduces mean esophageal eosinophil count, which was statistically significant over placebo in both active treatment arms. With regard to key secondary endpoint of improvement in dysphagia score, a positive numeric trend was observed with the higher dose (360 mg) of RPC4046 over placebo (nearing statistical significance). With respect to the effect of RPC4046 on various subgroups of patients, greater treatment effect was observed in the steroid refractory subgroup compared to the non-steroid-refractory subgroup. With respect to dosing,

TABLE 12

Summary of treatment-emergent adverse events (TEAE) in the safety population of subjects who were given placebo or treated with the low dose (180 mg) or high dose (360 mg) of RPC4046. Treatment emergent adverse events were monitored for frequency, severity, relation to the condition and treatment. TEAE leading to study drug discontinuation (d/c) was not observed in the placebo group. In both the placebo group and the treatment group of subjects reporting ≥1 serious TEAE, it was determined that the adverse events were unrelated to the placebo or the drug.

| Number of subjects experiencing | Placebo (N = 34) n (%) | RPC4046 180 mg (N = 31) n (%) | RPC4046 360 mg (N = 34) n (%) |
|---|---|---|---|
| ≥1 TEAE | 22 (64.7) | 20 (64.5) | 29 (85.3) |
| ≥1 moderate or severe TEAE | 15 (44.1) | 7 (22.6) | 11 (32.4) |
| ≥1 severe TEAE | 2 (5.9) | 2 (6.5) | 2 (5.9) |
| ≥1 possible, probable, or related TEAE | 13 (38.2) | 11 (35.5) | 18 (52.9) |
| ≥1 related TEAE | 4 (11.8) | 3 (9.7) | 5 (14.7) |
| ≥1 serious TEAE | 2 (5.9) | 0 | 1 (2.9) |
| ≥1 related serious TEAE | 0 | 0 | 0 |
| ≥1 TEAE with fatal outcome | 0 | 0 | 0 |
| ≥1 TEAE leading to study drug d/c | 0 | 1 (3.2) | 3 (8.8) |
| Death related to study drug | 0 | 0 | 0 | numerically greater improvements were observed with the RPC 360 mg dose (as measured by the DSD and EEsAI). With respect to global assessment of disease severity (both subject's and clinician's), treatment with RPC4046 resulted in a statistically significant improvement over placebo. Overall RPC4046 appeared to be generally safe and well-tolerated by subjects. The most-frequently reported adverse events were headache, URI, arthralgia, nasopharyngitis, sinusitis, abdominal pain and oropharyngeal pain. There were no reported instances of infusional hypersensitivity events within the treatment groups.

EQUIVALENTS

Those skilled in the art will recognize, or be able to ascertain using no more than routine experimentation, many equivalents to the specific embodiments and methods described herein. Such equivalents are intended to be encompassed by the scope of the following claims.

---

We claim:

1. A method of treating eosinophilic esophagitis (EoE) in a subject, comprising subcutaneously administering about 180 mg to about 360 mg of an anti-IL-13 antibody, or antigen binding fragment thereof, to the subject weekly, thereby treating EoE in the subject, wherein the anti-IL-13 antibody, or antigen binding fragment thereof, comprises six CDRs:
   CDR-H1—residues 31-37 of SEQ ID NO:2,
   CDR-H2—residues 52-67 of SEQ ID NO:2,
   CDR-H3—residues 100-112 of SEQ ID NO:2;
   CDR-L1—residues 24-34 of SEQ ID NO:3,
   CDR-L2—residues 50-56 of SEQ ID NO:3, and
   CDR-L3—residues 89-97 of SEQ ID NO:3.

2. The method of claim 1, wherein the anti-IL-13 antibody, or antigen-binding fragment thereof, binds to IL-13 and prevents interaction between IL-13 and an IL-13 receptor.

3. The method of claim 1, wherein the anti-IL-13 antibody, or antigen-binding fragment thereof, comprises a heavy chain variable region comprising SEQ ID NO: 2 and a light chain variable region comprising SEQ ID NO: 3.

4. The method of claim 1, comprising subcutaneously administering about 180 mg of the anti-IL-13 antibody, or antigen binding fragment thereof, to the subject weekly.

5. The method of claim 1, comprising subcutaneously administering about 360 mg of the anti-IL-13 antibody, or antigen binding fragment thereof, to the subject weekly.

6. The method of claim 1, further comprising selecting a subject who exhibits at least one symptom associated with eosinophilic esophagitis (EoE).

7. The method of claim 6, wherein the symptom associated with EoE is selected from the group consisting of eosinophilic infiltration of the esophagus, thickening of the esophageal wall, food refusal, vomiting, abdominal pain, heartburn, regurgitation, dysphagia, and food impaction.

8. The method of claim 6, wherein the subject also has a disease or disorder selected from the group consisting of atopic dermatitis, asthma, allergic rhinitis, allergic conjunctivitis, and a combination thereof.

9. The method of claim 6, wherein the subject is selected based on an elevated level of a biomarker associated with eosinophilic esophagitis (EoE), wherein the biomarker is selected from the group consisting of esophagus eosinophils, eotaxin-3, periostin, serum IgE, IL-13, IL-5, serum thymus and activation regulated chemokine (TARC; CCL17), thymic stromal lymphopoietin (TSLP), serum ECP, eosinophil-derived neurotoxin (EDN), and a combination thereof.

10. The method of claim 6, wherein the subject is selected based on the mean esophageal eosinophil counts in a biopsy sample obtained from the subject during an esophageal endoscopy.

11. The method of claim 6, wherein the subject is selected based on peak eosinophil count of 15 per high powered field (HPF) in the esophagus.

12. The method of claim 1, wherein the subject exhibits at least 50% decrease in the number of eosinophils per HPF from the peak level after at least 16 weeks of administration of the anti-IL-13 antibody, or antigen binding fragment thereof.

13. The method of claim 1, wherein the subject is a human subject.

14. The method of claim 1, wherein the subject is a steroid naïve subject who has not previously undergone steroid therapy.

15. The method of claim 1, wherein the subject has previously undergone steroid therapy.

16. The method of claim 15, wherein the subject is non-steroid refractory.

17. The method of claim 15, wherein the subject is steroid-refractory.

18. The method of claim 1, wherein the anti-IL-13 antibody, or antigen-binding portion thereof, is administered to the subject for at least about 16 weeks.

19. The method of claim 1, wherein the anti-IL-13 antibody, or antigen-binding portion thereof, is administered to the subject for the duration of EoE disease.

20. The method of claim 1, further comprising determining
   (i) a mean esophageal eosinophil count measured in the 5 most inflamed high powered fields (HPF) in esophageal biopsies before and after administration of the anti-IL-13 antibody, or antigen-binding portion thereof, to the subject, wherein a decrease in the mean esophageal eosinophil count after administration of the anti-IL-13 antibody, or antigen-binding portion thereof, to the subject as compared to the mean esophageal eosinophil count before administration indicates that the anti-IL-13 antibody, or antigen-binding portion thereof, is effective in treating the subject;
   (ii) dysphagia clinical symptoms before and after administration of the anti-IL-13 antibody, or antigen-binding portion thereof, to the subject, wherein a decrease in the dysphagia clinical symptoms after administration of the anti-IL-13 antibody, or antigen-binding portion thereof, to the subject as compared to the dysphagia clinical symptoms before administration indicates that the anti-IL-13 antibody, or antigen-binding portion thereof, is effective in treating the subject;
   (iii) a dysphagia symptom questionnaire (DSQ) score before and after administration of the anti-IL-13 antibody, or antigen-binding portion thereof, to the subject, wherein a decrease in the DSQ score after administration of the anti-IL-13 antibody, or antigen-binding portion thereof, to the subject as compared to the DSQ score before administration indicates that the anti-IL-13 antibody, or antigen-binding portion thereof, is effective in treating the subject;
   (iv) mean eosinophilic esophagitis (EoE) endoscopic reference score (EREF) before and after administration of the anti-IL-13 antibody, or antigen-binding portion thereof, to the subject, wherein a decrease in the EREF after administration of the anti-IL-13 antibody, or antigen-binding portion thereof, to the subject as compared to the EREF before administration indicates that the anti-IL-13 antibody, or antigen-binding portion thereof, is effective in treating the subject;
   (v) a subject's global assessment of disease severity before and after administration of the anti-IL-13 antibody, or antigen-binding portion thereof, to the subject, wherein a decrease in the subject's global assessment of disease severity after administration of the anti-IL-13 antibody, or antigen-binding portion thereof, to the subject as compared to the subject's global assessment of disease severity before administration indicates that the anti-IL-13 antibody, or antigen-binding portion thereof, is effective in treating the subject;
   (vi) a clinician's global assessment of disease severity before and after administration of the anti-IL-13 antibody, or antigen-binding portion thereof, to the subject, wherein a decrease in the clinician's global assessment of disease severity after administration of the anti-IL-13 antibody, or antigen-binding portion thereof, to the subject as compared to the clinician's global assessment of disease severity before administration indicates that the anti-IL-13 antibody, or antigen-binding portion thereof, is effective in treating the subject; and/or
   (vii) a histology grade and a mean stage-adjusted score before and after administration of the anti-IL-13 antibody, or antigen-binding portion thereof, to the subject, wherein a decrease in the histology grade or the mean stage-adjusted score after administration of the anti-IL-13 antibody, or antigen-binding portion thereof, to the subject as compared to the histology grade or the mean stage-adjusted score before administration indicates that the anti-IL-13 antibody, or antigen-binding portion thereof, is effective in treating the subject.

21. The method of claim 20, wherein the dysphagia clinical symptoms of (ii) are assessed using the eosinophilic esophagitis activity index (EEsAI) and recorded as a daily symptom diary (DSD) score.

22. The method of claim 20, wherein the EREF of (iv) is determined based on the presence of inflammatory markers in the esophagus, the presence of remodeling markers in the esophagus, or a combination thereof.

23. The method of claim 20, wherein the EREF of (iv) is determined based on the presence or absence of plurality of features selected from the group consisting of edema, fixed rings, exudates, furrows and stricture, or a combination thereof.

24. The method of claim 1, further comprising administering an additional agent to the subject.

25. The method of claim 24, wherein the additional agent is a steroid.

26. The method of claim 25, wherein the steroid is budesonide.

27. The method of claim 24 wherein the additional agent is selected from the group consisting of: an imaging agent, a cytotoxic agent, an angiogenesis inhibitor, a kinase inhibitor, a co-stimulation molecule blocker, an adhesion molecule blocker, an anti-cytokine antibody or functional fragment thereof; methotrexate, a cyclosporin, a rapamycin, an FK506, a detectable label or reporter, a TNF antagonist, an anti-rheumatic, a muscle relaxant, a narcotic, a non-steroid anti-inflammatory drug (NSAID), an analgesic, an anesthetic, a sedative, a local anesthetic, a neuromuscular blocker, an antimicrobial, an antipsoriatic, a corticosteroid, an anabolic steroid, an erythropoietin, an immunization, an immunoglobulin, an immunosuppressive, a growth hormone, a hormone replacement drug, a radiopharmaceutical, an antidepressant, an antipsychotic, a stimulant, an asthma medication, a beta agonist, an inhaled steroid, an oral steroid, an epinephrine or analog, a cytokine, and a cytokine antagonist.

* * * * *